United States Patent
Huppert et al.

(10) Patent No.: US 10,258,282 B2
(45) Date of Patent: *Apr. 16, 2019

(54) CONFORMAL SENSOR SYSTEMS FOR SENSING AND ANALYSIS OF CARDIAC ACTIVITY

(71) Applicant: MC10, Inc., Lexington, MA (US)

(72) Inventors: Gilbert Lee Huppert, Stoneham, MA (US); Roozbeh Ghaffari, Cambridge, MA (US); Melissa Ceruolo, Swampscott, MA (US); Bryan Keen, Somerville, MA (US); Milan Raj, Natick, MA (US); Bryan McGrane, Cambridge, MA (US)

(73) Assignee: MC10, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/921,076

(22) Filed: Mar. 14, 2018

(65) Prior Publication Data

US 2018/0199884 A1   Jul. 19, 2018

Related U.S. Application Data

(63) Continuation of application No. 15/038,401, filed as application No. PCT/US2014/066810 on Nov. 21, 2014, now Pat. No. 9,949,691.

(Continued)

(51) Int. Cl.
*A61B 5/00* (2006.01)
*A61B 5/0205* (2006.01)
(Continued)

(52) U.S. Cl.
CPC .......... *A61B 5/6833* (2013.01); *A61B 5/0006* (2013.01); *A61B 5/0022* (2013.01);
(Continued)

(58) Field of Classification Search
CPC .................. A61B 5/6833; A61B 5/006
(Continued)

(56) References Cited

U.S. PATENT DOCUMENTS

| | | |
|---|---|---|
| 3,207,694 A | 9/1965 | Gogek |
| 3,716,861 A | 2/1973 | Root |

(Continued)

FOREIGN PATENT DOCUMENTS

| | | |
|---|---|---|
| CN | 202068986 U | 12/2011 |
| DE | 10 2006 011 596 A1 | 9/2007 |

(Continued)

OTHER PUBLICATIONS

Carvalhal et al., "Electrochemical Detection in a Paper-Based Separation Device", Analytical Chemistry, vol. 82, No. 3, (1162-1165) (4 pages) (Jan. 7, 2010).

(Continued)

*Primary Examiner* — Nadia A Mahmood
(74) *Attorney, Agent, or Firm* — Nixon Peabody LLP

(57) ABSTRACT

Systems, methods and apparatuses for monitoring cardiac activity of an individual using a conformal cardiac sensor device are presented herein. A conformal cardiac sensor device for analyzing cardiac activity includes a flexible substrate for coupling to the user, and a heart sensor component embedded on/in the substrate. The heart sensor component contacts a portion of the user's skin and measures electrical variable(s) indicative of cardiac activity. A biometric sensor component is embedded on/in the flexible substrate and measures physiological variable(s) indicative of cardiac activity of the user. A microprocessor, which is embedded on/in the flexible substrate, is communicatively coupled to the heart sensor component and biometric sensor component and operable to execute microprocessor executable instructions for controlling the measurements of elec- (Continued)

trical data and physiological data. A wireless communication component is embedded on/in the flexible substrate and is operable to transmit data indicative of the measurements obtained by the sensor components.

20 Claims, 22 Drawing Sheets

Related U.S. Application Data

(60) Provisional application No. 61/907,973, filed on Nov. 22, 2013, provisional application No. 61/907,991, filed on Nov. 22, 2013.

(51) Int. Cl.
A61B 5/024 (2006.01)
A61B 5/0408 (2006.01)
A61B 5/0476 (2006.01)
A61B 5/0488 (2006.01)
A61M 37/00 (2006.01)
A61B 5/01 (2006.01)
A61B 5/02 (2006.01)
A61B 5/08 (2006.01)

(52) U.S. Cl.
CPC ........ A61B 5/0205 (2013.01); A61B 5/02055 (2013.01); A61B 5/02444 (2013.01); A61B 5/0408 (2013.01); A61B 5/0476 (2013.01); A61B 5/04085 (2013.01); A61B 5/04087 (2013.01); A61B 5/0488 (2013.01); A61B 5/486 (2013.01); A61B 5/4839 (2013.01); A61B 5/7271 (2013.01); A61M 37/00 (2013.01); A61B 5/01 (2013.01); A61B 5/02028 (2013.01); A61B 5/08 (2013.01); A61B 5/4815 (2013.01); A61B 5/4866 (2013.01); A61B 5/4875 (2013.01); A61B 2560/0214 (2013.01); A61B 2560/0475 (2013.01); A61B 2562/0219 (2013.01); A61B 2562/08 (2013.01); A61B 2562/164 (2013.01)

(58) Field of Classification Search
USPC .................................. 600/513, 300
See application file for complete search history.

(56) References Cited

U.S. PATENT DOCUMENTS

| | | | |
|---|---|---|---|
| 3,805,427 A | 4/1974 | Epstein |
| 3,838,240 A | 9/1974 | Schelhorn |
| 3,892,905 A | 7/1975 | Albert |
| 4,136,162 A | 1/1979 | Fuchs |
| 4,278,474 A | 7/1981 | Blakeslee |
| 4,304,235 A | 12/1981 | Kaufman |
| 4,416,288 A | 11/1983 | Freeman |
| 4,658,153 A | 4/1987 | Brosh |
| 4,911,169 A | 3/1990 | Ferrari |
| 5,059,424 A | 10/1991 | Cartmell |
| 5,064,576 A | 11/1991 | Suto |
| 5,272,375 A | 12/1993 | Belopolsky |
| 5,306,917 A | 4/1994 | Black |
| 5,326,521 A | 7/1994 | East |
| 5,331,966 A | 7/1994 | Bennett |
| 5,360,987 A | 11/1994 | Shibib |
| 5,471,982 A | 5/1995 | Edwards |
| 5,454,270 A | 10/1995 | Brown |
| 5,491,651 A | 2/1996 | Janic |
| 5,567,975 A | 10/1996 | Walsh |
| 5,580,794 A | 12/1996 | Allen |
| 5,617,870 A | 4/1997 | Hastings |
| 5,811,790 A | 9/1998 | Endo |
| 5,817,008 A | 10/1998 | Rafert |
| 5,907,477 A | 5/1999 | Tuttle |
| 6,063,046 A | 5/2000 | Allum |
| 6,220,916 B1 | 4/2001 | Bart |
| 6,265,090 B1 | 7/2001 | Nishide |
| 6,270,872 B1 | 8/2001 | Cline |
| 6,282,960 B1 | 9/2001 | Samuels |
| 6,343,514 B1 | 2/2002 | Smith |
| 6,387,052 B1 | 5/2002 | Quinn |
| 6,410,971 B1 | 6/2002 | Otey |
| 6,421,016 B1 | 7/2002 | Phillips |
| 6,450,026 B1 | 9/2002 | Desarnaud |
| 6,455,931 B1 | 9/2002 | Hamilton |
| 6,567,158 B1 | 5/2003 | Falcial |
| 6,626,940 B2 | 9/2003 | Crowley |
| 6,628,987 B1 | 9/2003 | Hill |
| 6,641,860 B1 | 11/2003 | Kaiserman |
| 6,775,906 B1 | 8/2004 | Silverbrook |
| 6,784,844 B1 | 8/2004 | Boakes |
| 6,825,539 B2 | 11/2004 | Tai |
| 6,965,160 B2 | 11/2005 | Cobbley |
| 6,987,314 B1 | 1/2006 | Yoshida |
| 7,259,030 B2 | 8/2007 | Daniels |
| 7,265,298 B2 | 9/2007 | Maghribi |
| 7,302,751 B2 | 12/2007 | Hamburgen |
| 7,337,012 B2 | 2/2008 | Maghribi |
| 7,487,587 B2 | 2/2009 | Vanfleteren |
| 7,491,892 B2 | 2/2009 | Wagner |
| 7,521,292 B2 | 4/2009 | Rogers |
| 7,557,367 B2 | 7/2009 | Rogers |
| 7,618,260 B2 | 11/2009 | Daniel |
| 7,622,367 B1 | 11/2009 | Nuzzo |
| 7,727,228 B2 | 6/2010 | Abboud |
| 7,739,791 B2 | 6/2010 | Brandenburg |
| 7,759,167 B2 | 7/2010 | Vanfleteren |
| 7,815,095 B2 | 10/2010 | Fujisawa |
| 7,960,246 B2 | 6/2011 | Flamand |
| 7,982,296 B2 | 7/2011 | Nuzzo |
| 8,097,926 B2 | 1/2012 | De Graff |
| 8,198,621 B2 | 6/2012 | Rogers |
| 8,207,473 B2 | 6/2012 | Axisa |
| 8,217,381 B2 | 7/2012 | Rogers |
| 8,332,053 B1 | 12/2012 | Patterson |
| 8,372,726 B2 | 2/2013 | De Graff |
| 8,389,862 B2 | 3/2013 | Arora |
| 8,431,828 B2 | 4/2013 | Vanfleteren |
| 8,440,546 B2 | 5/2013 | Nuzzo |
| 8,536,667 B2 | 9/2013 | de Graff |
| 8,552,299 B2 | 10/2013 | Rogers |
| 8,609,471 B2 | 12/2013 | Xu |
| 8,618,656 B2 | 12/2013 | Oh |
| 8,664,699 B2 | 3/2014 | Nuzzo |
| 8,679,888 B2 | 3/2014 | Rogers |
| 8,729,524 B2 | 5/2014 | Rogers |
| 8,754,396 B2 | 6/2014 | Rogers |
| 8,865,489 B2 | 10/2014 | Rogers |
| 8,886,334 B2 | 11/2014 | Ghaffari |
| 8,905,772 B2 | 12/2014 | Rogers |
| 9,012,784 B2 | 4/2015 | Arora |
| 9,082,025 B2 | 7/2015 | Fastert |
| 9,105,555 B2 | 8/2015 | Rogers |
| 9,105,782 B2 | 8/2015 | Rogers |
| 9,107,592 B2 | 8/2015 | Litt |
| 9,119,533 B2 | 9/2015 | Ghaffari |
| 9,123,614 B2 | 9/2015 | Graff |
| 9,159,635 B2 | 10/2015 | Elolampi |
| 9,168,094 B2 | 10/2015 | Lee |
| 9,171,794 B2 | 10/2015 | Rafferty |
| 9,186,060 B2 | 11/2015 | De Graff |
| 9,226,402 B2 | 12/2015 | Hsu |
| 9,247,637 B2 | 1/2016 | Hsu |
| 9,289,132 B2 | 3/2016 | Ghaffari |
| 9,295,842 B2 | 3/2016 | Ghaffari |
| 9,320,907 B2 | 4/2016 | Bogie |
| 9,324,733 B2 | 4/2016 | Rogers |
| 9,372,123 B2 | 6/2016 | Li |
| 9,408,305 B2 | 8/2016 | Hsu |
| 9,420,953 B2 | 8/2016 | Litt |
| 9,450,043 B2 | 9/2016 | Nuzzo |

(56) References Cited

U.S. PATENT DOCUMENTS

| | | |
|---|---|---|
| 9,515,025 B2 | 12/2016 | Rogers |
| 9,516,758 B2 | 12/2016 | Arora |
| 9,545,216 B2 | 1/2017 | D'Angelo |
| 9,545,285 B2 | 1/2017 | Ghaffari |
| 9,554,850 B2 | 1/2017 | Lee |
| 9,579,040 B2 | 2/2017 | Rafferty |
| 9,583,428 B2 | 2/2017 | Rafferty |
| D781,270 S | 3/2017 | Li |
| 9,622,680 B2 | 4/2017 | Ghaffari |
| 9,629,586 B2 | 4/2017 | Ghaffari |
| 9,647,171 B2 | 5/2017 | Rogers |
| 9,655,560 B2 | 5/2017 | Ghaffari |
| 9,662,069 B2 | 5/2017 | De Graff |
| 9,702,839 B2 | 7/2017 | Ghaffari |
| 9,704,908 B2 | 7/2017 | De Graff |
| 9,706,647 B2 | 7/2017 | Hsu |
| 9,723,122 B2 | 8/2017 | Ghaffari |
| 9,723,711 B2 | 8/2017 | Elolampi |
| 9,750,421 B2 | 9/2017 | Ghaffari |
| 9,757,050 B2 | 9/2017 | Ghaffari |
| 9,761,444 B2 | 9/2017 | Nuzzo |
| 9,768,086 B2 | 9/2017 | Nuzzo |
| 9,801,557 B2 | 10/2017 | Ghaffari |
| 9,844,145 B2 | 10/2017 | Hsu |
| 9,810,623 B2 | 11/2017 | Ghaffari |
| 9,833,190 B2 | 12/2017 | Ghaffari |
| 9,839,367 B2 | 12/2017 | Litt |
| 9,846,829 B2 | 12/2017 | Fastert |
| 9,894,757 B2 | 2/2018 | Arora |
| 9,899,330 B2 | 2/2018 | Dalal |
| 2001/0012918 A1 | 8/2001 | Swanson |
| 2001/0021867 A1 | 9/2001 | Kordis |
| 2002/0000813 A1 | 1/2002 | Hirono |
| 2002/0026127 A1 | 2/2002 | Balbierz |
| 2002/0077534 A1 | 6/2002 | Durousseau |
| 2002/0079572 A1 | 6/2002 | Khan |
| 2002/0082515 A1 | 6/2002 | Campbell |
| 2002/0094701 A1 | 7/2002 | Biegelsen |
| 2002/0107436 A1 | 8/2002 | Barton |
| 2002/0113739 A1 | 8/2002 | Howard |
| 2002/0128700 A1 | 9/2002 | Cross, Jr. |
| 2002/0145467 A1 | 10/2002 | Minch |
| 2002/0151934 A1 | 10/2002 | Levine |
| 2002/0158330 A1 | 10/2002 | Moon |
| 2002/0173730 A1 | 11/2002 | Pottgen |
| 2002/0193724 A1 | 12/2002 | Stebbings |
| 2003/0017848 A1 | 1/2003 | Engstrom |
| 2003/0045025 A1 | 3/2003 | Coyle |
| 2003/0097165 A1 | 5/2003 | Krulevitch |
| 2003/0120271 A1 | 6/2003 | Burnside |
| 2003/0162507 A1 | 8/2003 | Vatt |
| 2003/0214408 A1 | 11/2003 | Grajales |
| 2003/0236455 A1 | 12/2003 | Swanson |
| 2004/0006264 A1 | 1/2004 | Mojarradi |
| 2004/0085469 A1 | 5/2004 | Johnson |
| 2004/0092806 A1 | 5/2004 | Sagon |
| 2004/0106334 A1 | 6/2004 | Suzuki |
| 2004/0118831 A1 | 6/2004 | Martin |
| 2004/0135094 A1 | 7/2004 | Niigaki |
| 2004/0138558 A1 | 7/2004 | Dunki-Jacobs |
| 2004/0149921 A1 | 8/2004 | Smyk |
| 2004/0178466 A1 | 9/2004 | Merrill |
| 2004/0192082 A1 | 9/2004 | Wagner |
| 2004/0201134 A1 | 10/2004 | Kawai |
| 2004/0203486 A1 | 10/2004 | Shepherd |
| 2004/0221370 A1 | 11/2004 | Hannula |
| 2004/0238819 A1 | 12/2004 | Maghribi |
| 2004/0243204 A1 | 12/2004 | Maghribi |
| 2005/0021103 A1 | 1/2005 | DiLorenzo |
| 2005/0029680 A1 | 2/2005 | Jung |
| 2005/0030408 A1 | 2/2005 | Ito |
| 2005/0067293 A1 | 3/2005 | Naito |
| 2005/0070778 A1 | 3/2005 | Lackey |
| 2005/0096513 A1 | 5/2005 | Ozguz |
| 2005/0113744 A1 | 5/2005 | Donoghue |
| 2005/0139683 A1 | 6/2005 | Yi |
| 2005/0171524 A1 | 8/2005 | Stern |
| 2005/0203366 A1 | 9/2005 | Donoghue |
| 2005/0204811 A1 | 9/2005 | Neff |
| 2005/0248312 A1 | 11/2005 | Cao |
| 2005/0261617 A1 | 11/2005 | Hall |
| 2005/0258050 A1 | 12/2005 | Bruce |
| 2005/0285262 A1 | 12/2005 | Knapp |
| 2006/0003709 A1 | 1/2006 | Wood |
| 2006/0038182 A1 | 2/2006 | Rogers |
| 2006/0071349 A1 | 4/2006 | Tokushige |
| 2006/0084394 A1 | 4/2006 | Engstrom |
| 2006/0106321 A1 | 5/2006 | Lewinsky |
| 2006/0122298 A1 | 6/2006 | Menon |
| 2006/0128346 A1 | 6/2006 | Yasui |
| 2006/0154398 A1 | 7/2006 | Qing |
| 2006/0160560 A1 | 7/2006 | Josenhans |
| 2006/0235314 A1 | 10/2006 | Migliuolo |
| 2006/0248946 A1 | 11/2006 | Howell |
| 2006/0257945 A1 | 11/2006 | Masters |
| 2006/0264767 A1 | 11/2006 | Shennib |
| 2006/0270135 A1 | 11/2006 | Chrysler |
| 2006/0276702 A1 | 12/2006 | McGinnis |
| 2006/0286785 A1 | 12/2006 | Rogers |
| 2007/0027514 A1 | 2/2007 | Gerber |
| 2007/0031283 A1 | 2/2007 | Davis |
| 2007/0069894 A1 | 3/2007 | Lee |
| 2007/0108389 A1 | 5/2007 | Makela |
| 2007/0113399 A1 | 5/2007 | Kumar |
| 2007/0123756 A1 | 5/2007 | Kitajima |
| 2007/0139451 A1 | 6/2007 | Somasiri |
| 2007/0151358 A1 | 7/2007 | Chien |
| 2007/0179373 A1 | 8/2007 | Pronovost |
| 2007/0190880 A1 | 8/2007 | Dubrow |
| 2007/0270672 A1 | 11/2007 | Hayter |
| 2007/0270674 A1 | 11/2007 | Kane |
| 2008/0036097 A1 | 2/2008 | Ito |
| 2008/0046080 A1 | 2/2008 | Vanden Bulcke |
| 2008/0074383 A1 | 3/2008 | Dean |
| 2008/0091089 A1 | 4/2008 | Guilloty |
| 2008/0096620 A1 | 4/2008 | Lee |
| 2008/0139894 A1 | 6/2008 | Szydlo-Moore |
| 2008/0157235 A1 | 7/2008 | Rogers |
| 2008/0185534 A1 | 8/2008 | Simon |
| 2008/0188912 A1 | 8/2008 | Stone |
| 2008/0193749 A1 | 8/2008 | Thompson |
| 2008/0200973 A1 | 8/2008 | Mallozzi |
| 2008/0204021 A1 | 8/2008 | Leussler |
| 2008/0211087 A1 | 9/2008 | Mueller-Hipper |
| 2008/0237840 A1 | 10/2008 | Alcoe |
| 2008/0259576 A1 | 10/2008 | Johnson |
| 2008/0262381 A1 | 10/2008 | Kolen |
| 2008/0275327 A1 | 11/2008 | Faarbaek |
| 2008/0287167 A1 | 11/2008 | Caine |
| 2008/0297350 A1 | 12/2008 | Iwasa |
| 2008/0309807 A1 | 12/2008 | Kinoshita |
| 2008/0313552 A1 | 12/2008 | Buehler |
| 2009/0000377 A1 | 1/2009 | Shipps |
| 2009/0001550 A1 | 1/2009 | Li |
| 2009/0015560 A1 | 1/2009 | Robinson |
| 2009/0017884 A1 | 1/2009 | Rotschild |
| 2009/0048556 A1 | 2/2009 | Durand |
| 2009/0076363 A1 | 3/2009 | Bly |
| 2009/0088750 A1 | 4/2009 | Hushka |
| 2009/0107704 A1 | 4/2009 | Vanfleteren |
| 2009/0154736 A1 | 6/2009 | Lee |
| 2009/0184254 A1 | 7/2009 | Miura |
| 2009/0204168 A1 | 8/2009 | Kallmeyer |
| 2009/0215385 A1 | 8/2009 | Waters |
| 2009/0225751 A1 | 9/2009 | Koenck |
| 2009/0261828 A1 | 10/2009 | Nordmeyer-Massner |
| 2009/0273909 A1 | 11/2009 | Shin |
| 2009/0283891 A1 | 11/2009 | Dekker |
| 2009/0291508 A1 | 11/2009 | Babu |
| 2009/0294803 A1 | 12/2009 | Nuzzo |
| 2009/0317639 A1 | 12/2009 | Axisa |
| 2009/0322480 A1 | 12/2009 | Benedict |
| 2010/0002402 A1 | 1/2010 | Rogers |
| 2010/0030167 A1 | 2/2010 | Thirstrup |

(56) References Cited

U.S. PATENT DOCUMENTS

| | | |
|---|---|---|
| 2010/0036211 A1 | 2/2010 | La Rue |
| 2010/0059863 A1 | 3/2010 | Rogers |
| 2010/0072577 A1 | 3/2010 | Nuzzo |
| 2010/0073669 A1 | 3/2010 | Colvin |
| 2010/0087782 A1 | 4/2010 | Ghaffari |
| 2010/0090781 A1 | 4/2010 | Yamamoto |
| 2010/0090824 A1 | 4/2010 | Rowell |
| 2010/0116526 A1 | 5/2010 | Arora |
| 2010/0117660 A1 | 5/2010 | Douglas |
| 2010/0178722 A1 | 7/2010 | De Graff |
| 2010/0245011 A1 | 9/2010 | Chatzopoulos |
| 2010/0254092 A1 | 10/2010 | Dong |
| 2010/0271191 A1 | 10/2010 | De Graff |
| 2010/0298895 A1 | 11/2010 | Ghaffari |
| 2010/0317132 A1 | 12/2010 | Rogers |
| 2010/0321161 A1 | 12/2010 | Isabell |
| 2010/0327387 A1 | 12/2010 | Kasai |
| 2011/0011179 A1 | 1/2011 | Gustafsson |
| 2011/0019370 A1 | 1/2011 | Koh |
| 2011/0034760 A1 | 2/2011 | Brynelsen |
| 2011/0034912 A1 | 2/2011 | De Graff |
| 2011/0051384 A1 | 3/2011 | Kriechbaum |
| 2011/0054583 A1 | 3/2011 | Litt |
| 2011/0071603 A1 | 3/2011 | Moore |
| 2011/0098583 A1 | 4/2011 | Pandia |
| 2011/0101789 A1 | 5/2011 | Salter |
| 2011/0121822 A1 | 5/2011 | Parsche |
| 2011/0136436 A1 | 6/2011 | Hoyt |
| 2011/0140856 A1 | 6/2011 | Downie |
| 2011/0140897 A1 | 6/2011 | Purks |
| 2011/0175735 A1 | 7/2011 | Forster |
| 2011/0184320 A1 | 7/2011 | Shipps |
| 2011/0185611 A1 | 8/2011 | Adams |
| 2011/0213559 A1 | 9/2011 | Pollack |
| 2011/0215931 A1 | 9/2011 | Callsen |
| 2011/0218756 A1 | 9/2011 | Calisen |
| 2011/0218757 A1 | 9/2011 | Callsen |
| 2011/0220890 A1 | 9/2011 | Nuzzo |
| 2011/0222375 A1 | 9/2011 | Tsubata |
| 2011/0263950 A1 | 10/2011 | Larson |
| 2011/0270049 A1 | 11/2011 | Katra |
| 2011/0277813 A1 | 11/2011 | Rogers |
| 2011/0284268 A1 | 11/2011 | Palaniswamy |
| 2011/0306851 A1 | 12/2011 | Wang |
| 2011/0317737 A1 | 12/2011 | Klewer |
| 2012/0016258 A1 | 1/2012 | Webster |
| 2012/0051005 A1 | 3/2012 | Vanfleteren |
| 2012/0052268 A1 | 3/2012 | Axisa |
| 2012/0065937 A1 | 3/2012 | De Graff |
| 2012/0068848 A1 | 3/2012 | Campbell |
| 2012/0074546 A1 | 3/2012 | Chong |
| 2012/0087216 A1 | 4/2012 | Keung |
| 2012/0091594 A1 | 4/2012 | Landesberger |
| 2012/0092178 A1 | 4/2012 | Calisen |
| 2012/0092222 A1 | 4/2012 | Kato |
| 2012/0101413 A1 | 4/2012 | Beetel |
| 2012/0101538 A1 | 4/2012 | Ballakur |
| 2012/0108012 A1 | 5/2012 | Yasuda |
| 2012/0126418 A1 | 5/2012 | Feng |
| 2012/0150072 A1 | 6/2012 | Revol-Cavalier |
| 2012/0150074 A1 | 6/2012 | Yanev |
| 2012/0157804 A1 | 6/2012 | Rogers |
| 2012/0165759 A1 | 6/2012 | Rogers |
| 2012/0172697 A1 | 7/2012 | Urman |
| 2012/0178367 A1 | 7/2012 | Matsumoto |
| 2012/0179075 A1 | 7/2012 | Perry |
| 2012/0206097 A1 | 8/2012 | Scar |
| 2012/0215127 A1 | 8/2012 | Shikida |
| 2012/0220835 A1 | 8/2012 | Chung |
| 2012/0226130 A1 | 9/2012 | De Graff |
| 2012/0244848 A1 | 9/2012 | Ghaffari |
| 2012/0245444 A1 | 9/2012 | Otis |
| 2012/0256308 A1 | 10/2012 | Helin |
| 2012/0256492 A1 | 10/2012 | Song |
| 2012/0314382 A1 | 12/2012 | Wesselmann |
| 2012/0316455 A1 | 12/2012 | Rahman |
| 2012/0327608 A1 | 12/2012 | Rogers |
| 2013/0035751 A1 | 2/2013 | Shalev |
| 2013/0041235 A1 | 2/2013 | Rogers |
| 2013/0044215 A1 | 2/2013 | Rothkopf |
| 2013/0066365 A1 | 3/2013 | Belson |
| 2013/0079693 A1 | 3/2013 | Ranky |
| 2013/0085552 A1 | 4/2013 | Mandel |
| 2013/0099358 A1 | 4/2013 | Elolampi |
| 2013/0100618 A1 | 4/2013 | Rogers |
| 2013/0116520 A1 | 5/2013 | Roham |
| 2013/0118255 A1 | 5/2013 | Callsen |
| 2013/0123587 A1 | 5/2013 | Sarrafzadeh |
| 2013/0131660 A1 | 5/2013 | Monson |
| 2013/0147063 A1 | 6/2013 | Park |
| 2013/0150693 A1 | 6/2013 | D'angelo |
| 2013/0185003 A1 | 7/2013 | Carbeck |
| 2013/0192356 A1 | 8/2013 | De Graff |
| 2013/0197319 A1 | 8/2013 | Monty |
| 2013/0200268 A1 | 8/2013 | Rafferty |
| 2013/0211761 A1 | 8/2013 | Brandsma |
| 2013/0214300 A1 | 8/2013 | Lerman |
| 2013/0215467 A1 | 8/2013 | Fein |
| 2013/0225965 A1 | 8/2013 | Ghaffari |
| 2013/0237150 A1 | 9/2013 | Royston |
| 2013/0245387 A1 | 9/2013 | Patel |
| 2013/0245388 A1 | 9/2013 | Rafferty |
| 2013/0253285 A1 | 9/2013 | Bly |
| 2013/0261415 A1 | 10/2013 | Ashe |
| 2013/0261464 A1 | 10/2013 | Singh |
| 2013/0274562 A1 | 10/2013 | Ghaffari |
| 2013/0285836 A1 | 10/2013 | Proud |
| 2013/0313713 A1 | 11/2013 | Arora |
| 2013/0316442 A1 | 11/2013 | Meurville |
| 2013/0316487 A1 | 11/2013 | De Graff |
| 2013/0316645 A1 | 11/2013 | Li |
| 2013/0320503 A1 | 12/2013 | Nuzzo |
| 2013/0321373 A1 | 12/2013 | Yoshizumi |
| 2013/0325357 A1 | 12/2013 | Walerow |
| 2013/0328219 A1 | 12/2013 | Chau |
| 2013/0331914 A1 | 12/2013 | Lee |
| 2014/0001058 A1 | 1/2014 | Ghaffari |
| 2014/0002242 A1 | 1/2014 | Fenkanyn |
| 2014/0012160 A1 | 1/2014 | Ghaffari |
| 2014/0012242 A1 | 1/2014 | Lee |
| 2014/0022746 A1 | 1/2014 | Hsu |
| 2014/0039290 A1 | 2/2014 | De Graff |
| 2014/0097944 A1 | 4/2014 | Fastert |
| 2014/0110859 A1 | 4/2014 | Rafferty |
| 2014/0125458 A1 | 5/2014 | Bachman |
| 2014/0140020 A1 | 5/2014 | Rogers |
| 2014/0188426 A1 | 7/2014 | Fastert |
| 2014/0191236 A1 | 7/2014 | Nuzzo |
| 2014/0206976 A1 | 7/2014 | Thompson |
| 2014/0216524 A1 | 8/2014 | Rogers |
| 2014/0240932 A1 | 8/2014 | Hsu |
| 2014/0249520 A1 | 9/2014 | Ghaffari |
| 2014/0275835 A1 | 9/2014 | Lamego |
| 2014/0303452 A1 | 10/2014 | Ghaffari |
| 2014/0303520 A1 | 10/2014 | Telfort |
| 2014/0303680 A1 | 10/2014 | Donnelly |
| 2014/0308930 A1 | 10/2014 | Tran |
| 2014/0340857 A1 | 11/2014 | Hsu |
| 2014/0342174 A1 | 11/2014 | Tominaga |
| 2014/0350883 A1 | 11/2014 | Carter |
| 2014/0371547 A1 | 12/2014 | Gartenberg |
| 2014/0371823 A1 | 12/2014 | Mashiach |
| 2014/0374872 A1 | 12/2014 | Rogers |
| 2014/0375465 A1 | 12/2014 | Fenuccio |
| 2015/0001462 A1 | 1/2015 | Rogers |
| 2015/0019135 A1 | 1/2015 | Kacyvenski |
| 2015/0025394 A1 | 1/2015 | Hong |
| 2015/0035680 A1 | 2/2015 | Li |
| 2015/0035743 A1 | 2/2015 | Rosener |
| 2015/0069617 A1 | 3/2015 | Arora |
| 2015/0099976 A1 | 4/2015 | Ghaffari |
| 2015/0100135 A1 | 4/2015 | Ives |
| 2015/0126878 A1 | 5/2015 | An |
| 2015/0150505 A1 | 6/2015 | Kaskoun |

(56) References Cited

U.S. PATENT DOCUMENTS

| | | |
|---|---|---|
| 2015/0164377 A1 | 6/2015 | Nathan |
| 2015/0178806 A1 | 6/2015 | Nuzzo |
| 2015/0181700 A1 | 6/2015 | Rogers |
| 2015/0194817 A1 | 7/2015 | Lee |
| 2015/0237711 A1 | 8/2015 | Rogers |
| 2015/0241288 A1 | 8/2015 | Keen |
| 2015/0248833 A1 | 9/2015 | Arne |
| 2015/0260713 A1 | 9/2015 | Ghaffari |
| 2015/0272652 A1 | 10/2015 | Ghaffari |
| 2015/0286913 A1 | 10/2015 | Fastert |
| 2015/0320472 A1 | 11/2015 | Ghaffari |
| 2015/0335254 A1 | 11/2015 | Fastert |
| 2015/0342036 A1 | 11/2015 | Elolampi |
| 2015/0371511 A1 | 12/2015 | Miller |
| 2015/0373487 A1 | 12/2015 | Miller |
| 2016/0006123 A1 | 1/2016 | Li |
| 2016/0015962 A1 | 1/2016 | Shokoueinejad Maragheh |
| 2016/0027834 A1 | 1/2016 | de Graff |
| 2016/0037478 A1 | 2/2016 | Skaaksrud |
| 2016/0045162 A1 | 2/2016 | De Graff |
| 2016/0058380 A1 | 3/2016 | Lee |
| 2016/0066854 A1 | 3/2016 | Mei |
| 2016/0081192 A1 | 3/2016 | Hsu |
| 2016/0086909 A1 | 3/2016 | Garlock |
| 2016/0095652 A1 | 4/2016 | Lee |
| 2016/0099214 A1 | 4/2016 | Dalal |
| 2016/0099227 A1 | 4/2016 | Dalal |
| 2016/0111353 A1 | 4/2016 | Rafferty |
| 2016/0135740 A1 | 5/2016 | Ghaffari |
| 2016/0178251 A1 | 6/2016 | Johnson |
| 2016/0213262 A1 | 7/2016 | Ghaffari |
| 2016/0213424 A1 | 7/2016 | Ghaffari |
| 2016/0228640 A1 | 8/2016 | Pindado |
| 2016/0232807 A1 | 8/2016 | Ghaffari |
| 2016/0240061 A1 | 8/2016 | Li |
| 2016/0249174 A1 | 8/2016 | Patel |
| 2016/0256070 A1 | 9/2016 | Murphy |
| 2016/0271290 A1 | 9/2016 | Humayun |
| 2016/0284544 A1 | 9/2016 | Nuzzo |
| 2016/0287177 A1 | 10/2016 | Huppert |
| 2016/0293794 A1 | 10/2016 | Nuzzo |
| 2016/0309594 A1 | 10/2016 | Hsu |
| 2016/0322283 A1 | 11/2016 | McMahon |
| 2016/0338646 A1 | 11/2016 | Lee |
| 2016/0361015 A1 | 12/2016 | Wang |
| 2016/0371957 A1 | 12/2016 | Ghaffari |
| 2016/0381789 A1 | 12/2016 | Rogers |
| 2017/0019988 A1 | 1/2017 | McGrane |
| 2017/0049397 A1 | 2/2017 | Sun |
| 2017/0071491 A1 | 3/2017 | Litt |
| 2017/0079588 A1 | 3/2017 | Ghaffari |
| 2017/0079589 A1 | 3/2017 | Ghaffari |
| 2017/0083312 A1 | 3/2017 | Pindado |
| 2017/0086747 A1 | 3/2017 | Ghaffari |
| 2017/0086748 A1 | 3/2017 | Ghaffari |
| 2017/0086749 A1 | 3/2017 | Ghaffari |
| 2017/0095670 A1 | 4/2017 | Ghaffari |
| 2017/0095732 A1 | 4/2017 | Ghaffari |
| 2017/0105795 A1 | 4/2017 | Lee |
| 2017/0110417 A1 | 4/2017 | Arora |
| 2017/0164865 A1 | 6/2017 | Rafferty |
| 2017/0164866 A1 | 6/2017 | Rafferty |
| 2017/0181659 A1 | 6/2017 | Rafferty |
| 2017/0186727 A1 | 6/2017 | Dalal |
| 2017/0188942 A1 | 7/2017 | Ghaffari |
| 2017/0200670 A1 | 7/2017 | Rafferty |
| 2017/0200679 A1 | 7/2017 | Rogers |
| 2017/0200707 A1 | 7/2017 | Rogers |
| 2017/0223846 A1 | 8/2017 | Elolampi |
| 2017/0244285 A1 | 8/2017 | Raj |
| 2017/0244543 A1 | 8/2017 | Raj |
| 2017/0296114 A1 | 10/2017 | Ghaffari |
| 2017/0331524 A1 | 11/2017 | Aranyosi |
| 2017/0340236 A1 | 11/2017 | Ghaffari |
| 2018/0076336 A1 | 3/2018 | de Graff |
| 2018/0111353 A1 | 4/2018 | Huppert |

FOREIGN PATENT DOCUMENTS

| | | |
|---|---|---|
| DE | 10 2007 046 886 A1 | 4/2009 |
| DE | 10 2008 044 902 A1 | 3/2010 |
| EP | 0526855 A1 | 2/1993 |
| EP | 0585670 A2 | 3/1994 |
| EP | 0779059 A1 | 6/1997 |
| EP | 0952542 A1 | 10/1999 |
| EP | 1808124 A2 | 7/2007 |
| EP | 2259062 A2 | 12/2010 |
| EP | 2498196 A2 | 9/2012 |
| EP | 2541995 A1 | 1/2013 |
| JP | H 04-290489 A | 10/1992 |
| JP | 05-087511 A | 4/1993 |
| JP | 2002-263185 A | 9/2002 |
| JP | 2005-052212 A | 3/2005 |
| JP | 2009-170173 A | 7/2009 |
| WO | WO 1999/038211 A2 | 7/1999 |
| WO | WO 2002/047162 A2 | 6/2002 |
| WO | WO 2003/021679 A2 | 3/2003 |
| WO | WO 2004/084720 A2 | 10/2004 |
| WO | WO 2005/083546 A1 | 9/2005 |
| WO | WO 2005/122285 A2 | 12/2005 |
| WO | WO 2006/013573 A2 | 2/2006 |
| WO | WO 2007/003019 A2 | 1/2007 |
| WO | WO 2007/024983 A2 | 3/2007 |
| WO | WO 2007/116344 A1 | 10/2007 |
| WO | WO 2007/136726 A2 | 11/2007 |
| WO | WO 2008/030960 A2 | 3/2008 |
| WO | WO 2008/055212 A2 | 5/2008 |
| WO | WO 2009/036260 A1 | 3/2009 |
| WO | WO 2009/111641 A1 | 9/2009 |
| WO | WO 2009/114689 A1 | 9/2009 |
| WO | WO 2010/036807 A1 | 4/2010 |
| WO | WO 2010/042653 A1 | 4/2010 |
| WO | WO 2010/042957 A2 | 4/2010 |
| WO | WO 2010/046883 A1 | 4/2010 |
| WO | WO 2010/056857 A2 | 5/2010 |
| WO | WO 2010/081137 A2 | 7/2010 |
| WO | WO 2010/082993 A2 | 7/2010 |
| WO | WO 2010/102310 A2 | 9/2010 |
| WO | WO 2010/132552 A1 | 11/2010 |
| WO | WO 2011/003181 A1 | 1/2011 |
| WO | WO 2011/041727 A1 | 4/2011 |
| WO | WO 2011/084450 A1 | 7/2011 |
| WO | WO 2011/084709 A2 | 7/2011 |
| WO | WO 2011/124898 A1 | 10/2011 |
| WO | WO 2011/127331 A2 | 10/2011 |
| WO | WO 2012/094264 A2 | 7/2012 |
| WO | WO 2012/125494 A2 | 9/2012 |
| WO | WO 2012/166686 A2 | 12/2012 |
| WO | WO 2013/010171 A1 | 1/2013 |
| WO | WO 2013/022853 A1 | 2/2013 |
| WO | WO 2013/033724 A1 | 3/2013 |
| WO | WO 2013/034987 A3 | 3/2013 |
| WO | WO 2013/049716 A1 | 4/2013 |
| WO | WO 2013/052919 A2 | 4/2013 |
| WO | WO 2013/144738 A2 | 10/2013 |
| WO | WO 2013/144866 A1 | 10/2013 |
| WO | WO 2013/170032 A2 | 11/2013 |
| WO | WO 2014/007871 A1 | 1/2014 |
| WO | WO 2014/058473 A1 | 4/2014 |
| WO | WO 2014/059032 A1 | 4/2014 |
| WO | WO 2014/106041 A1 | 7/2014 |
| WO | WO 2014/110176 A1 | 7/2014 |
| WO | WO 2014/124044 A1 | 8/2014 |
| WO | WO 2014/124049 A2 | 8/2014 |
| WO | WO 2014/130928 A2 | 8/2014 |
| WO | WO 2014/130931 A1 | 8/2014 |
| WO | WO 2014/186467 A2 | 11/2014 |
| WO | WO 2014/197443 A1 | 12/2014 |
| WO | WO 2014/205434 A2 | 12/2014 |
| WO | WO 2015/021039 A1 | 2/2015 |
| WO | WO 2015/054312 A1 | 4/2015 |
| WO | WO 2015/077559 A1 | 5/2015 |

(56) References Cited

FOREIGN PATENT DOCUMENTS

| | | |
|---|---|---|
| WO | WO 2015/080991 A1 | 6/2015 |
| WO | WO 2015/102951 A2 | 7/2015 |
| WO | WO 2015/103483 A1 | 7/2015 |
| WO | WO 2015/103580 A2 | 7/2015 |
| WO | WO 2015/127458 A1 | 8/2015 |
| WO | WO 2015/134588 A1 | 9/2015 |
| WO | WO 2015/138712 A1 | 9/2015 |
| WO | WO 2015/145471 A1 | 10/2015 |
| WO | WO 2016/010983 A1 | 1/2016 |
| WO | WO 2016/048888 A1 | 3/2016 |
| WO | WO 2016/054512 A1 | 4/2016 |
| WO | WO 2016/057318 A1 | 4/2016 |
| WO | WO 2016/081244 A1 | 5/2016 |
| WO | WO 2016/0127050 A1 | 8/2016 |
| WO | WO 2016/134306 A1 | 8/2016 |
| WO | WO 2016-140961 A1 | 9/2016 |
| WO | WO 2016/205385 A1 | 12/2016 |
| WO | WO 2017/015000 A1 | 1/2017 |
| WO | WO 2017/059215 A1 | 4/2017 |
| WO | WO 2017/062508 A1 | 4/2017 |
| WO | WO 2017/184705 A1 | 10/2017 |
| WO | WO 2018/013569 A1 | 1/2018 |
| WO | WO 2018/013656 A1 | 1/2018 |
| WO | WO 2018/057911 A1 | 3/2018 |
| WO | WO 2018/081778 A1 | 5/2018 |
| WO | WO 2018/085336 A1 | 5/2018 |

OTHER PUBLICATIONS

Demura et al., "Immobilization of Glucose Oxidase with *Bombyx mori* Silk Fibroin by Only Stretching Treatment and its Application to Glucose Sensor," Biotechnology and Bioengineering, vol. 33, 598-603 (6 pages) (1989).
Ellerbee et al., "Quantifying Colorimetric Assays in Paper-Based Microfluidic Devices by Measuring the Transmission of Light through Paper," Analytical Chemistry, vol. 81, No. 20 8447-8452, (6 pages) (Oct. 15, 2009).
Halsted, "Ligature and Suture Material," Journal of the American Medical Association, vol. LX, No. 15, 1119-1126, (8 pages) (Apr. 12, 1913).
Kim et al., "Complementary Metal Oxide Silicon Integrated Circuits Incorporating Monolithically Integrated Stretchable Wavy Interconnects," Applied Physics Letters, vol. 93, 044102-044102.3 (3 pages) (Jul. 31, 2008).
Kim et al., "Dissolvable Films of Silk Fibroin for Ultrathin Conformal Bio-Integrated Electronics," Nature, 1-8 (8 pages) (Apr. 18, 2010).
Kim et al., "Materials and Noncoplanar Mesh Designs for Integrated Circuits with Linear Elastic Responses to Extreme Mechanical Deformations," PNAS, vol. 105, No. 48, 18675-18680 (6 pages) (Dec. 2, 2008).
Kim et al., "Stretchable and Foldable Silicon Integrated Circuits," Science, vol. 320, 507-511 (5 pages) (Apr. 25, 2008).
Kim et al., "Electrowetting on Paper for Electronic Paper Display," ACS Applied Materials & Interfaces, vol. 2, No. 11, (3318-3323) (6 pages) (Nov. 24, 2010).
Ko et al., "A Hemispherical Electronic Eye Camera Based on Compressible Silicon Optoelectronics," Nature, vol. 454, 748-753 (6 pages) (Aug. 7, 2008).
Lawrence et al., "Bioactive Silk Protein Biomaterial Systems for Optical Devices," Biomacromolecules, vol. 9, 1214-1220 (7 pages) (Nov. 4, 2008).
Meitl et al., "Transfer Printing by Kinetic Control of Adhesion to an Elastomeric Stamp," Nature, vol. 5, 33-38 (6 pages) (Jan. 2006).
Omenetto et al., "A New Route for Silk," Nature Photonics, vol. 2, 641-643 (3 pages) (Nov. 2008).
Omenetto et al., "New Opportunities for an Ancient Material," Science, vol. 329, 528-531 (5 pages) (Jul. 30, 2010).
Siegel et al., "Foldable Printed Circuit Boards on Paper Substrates," Advanced Functional Materials, vol. 20, No. 1, 28-35, (8 pages) (Jan. 8, 2010).
Tsukada et al., "Structural Changes of Silk Fibroin Membranes Induced by Immersion in Methanol Aqueous Solutions," Journal of Polymer Science, vol. 32, 961-968 (8 pages) (1994).
Wang et al., "Controlled Release From Multilayer Silk Biomaterial Coatings to Modulate Vascular Cell Responses" Biomaterials, 29, 894-903 (10 pages) (Nov. 28, 2008).
Wikipedia, "Ball bonding" article [online]. Cited in PCT/US2015/051210 search report dated Mar. 1, 2016 with the following information "Jun. 15, 2011 [retrieved on Nov. 15, 2015}. Retrieved Dec. 18, 29 from the Internet: <URL: http://web.archive.org/web/20110615221003/hltp://en.wikipedia.org/wiki/Ball_bonding>., entire document, especially para 1, 4, 5, 6," 2 pages, last page says ("last modified on May 11, 2011").
Bossuyt et al., "Stretchable Electronics Technology for Large Area Applications: Fabrication and Mechanical Characterizations", vol. 3, pp. 229-235 (7 pages) (Feb. 2013).
Jones et al., "Stretchable Interconnects for Elastic Electronic Surfaces". vol. 93, pp. 1459-1467 (9 pages) (Aug. 2005).
Lin et al., "Design and Fabrication of Large-Area, Redundant, Stretchable Interconnect Meshes Using Excimer Laser Photoablation and in Situ Masking", (10 pages) (Aug. 2010).
Kim et al., "A Biaxial Stretchable Interconnect With Liquid-Alloy-Covered Joints on Elastomeric Substrate", vol. 18, pp. 138-146 (9 pages) (Feb. 2009).
Kinkeldi et al., "Encapsulation for Flexible Electronic Devices", IEE Electron Device Letters, 32(12):1743-5 (2011).
Hsu et al., "Epidermal electronics: Skin sweat patch", Microsystems, Packaging, Assembly and Circuits Technology Conference (IMPACT), 2012 7th International. IEEE, 2012.
Siegel et al., "Foldable printed circuit boards on paper substrates", Advanced Functional Materials, 20:28-35 (2010).
Ellerbee et al., "Quantifying colorimetric assays in paper-based microfluidic devices by measuring the transmission of light through paper", Anal. Chem.,81(20):8447-52 (2009).
Wehner et al.; "A Lightweight Soft Exosuit for Gait Assistance"; IEEE International Conference on Robotics and Automation (ICRA), May 6-10, 2013. Retrieved from https://micro.seas.harvard.edu/papers/Wehner_ICRA13.pdf (8 pages).
Cauwe et al., "Flexible and Stretchable Circuit Technologies for Space Applications," 5th Electronic Materials, Processes and Packaging for Space, May 20-22, 2014 (18 pages).
Hild, "Surface Energy of Plastics," Dec. 16, 2009. Retrieved from https://www.tstar.com/blog/bid/33845/surface-energy-of-plastics (3 pages).
Hodge et al., "A Microcolorimetric Method for the Determination of Chloride," Microchemical Journal, vol. 7, Issue 3, Sep. 30, 1963, pp. 326-330 (5 pages).
Bonifácio et al., "An improved flow system for chloride determination in natural waters exploiting solid-phase reactor and long pathlength spectrophotometry," Talanta, vol. 72, Issue 2, Apr. 30, 2007, pp. 663-667 (5 pages).
Meyer et al., "The Effect of Gelatin Cross-Linking on the Bioequivalence of Hard and Soft Gelatin Acetaminophen Capsules," Pharmaceutical Research, vol. 17, No. 8, Aug. 31, 2000, pp. 962-966 (5 pages).
Extended European Search Report for Application No. EP 14863481.9 dated Jul. 6, 2017 (8 pages).
International Search Report for PCT/US2014/066810 dated Apr. 13, 2015 (4 pages).
Written Opinion of International Searching Authority for PCT/US2014/066810 dated Apr. 13, 2015 (8 pages).
U.S. Appl. No. 14/588,765, filed Jan. 2, 2015, S. Lee et al., Integrated Devices for Low Power Quantitative Measurements.
U.S. Appl. No. 14/859,680, filed Sep. 21, 2015, D. Garlock, Methods and Apparatuses for Shaping and Looping Bonding Wires That Serve as Stretchable and Bendable Interconnects.
U.S. Appl. No. 14/870,802, filed Sep. 30, 2015, M. Dalal et al., Flexible Interconnects for Modules of Integrated Circuits and Methods of Making and Using the Same.
U.S. Appl. No. 15/016,937, filed Feb. 5, 2016, Jesus Pindado et al., Method and System for Interacting with an Environment.
U.S. Appl. No. 15/048,576, filed Feb. 19, 2016, Shyamal Patel et al., Automated Detection and Configuration of Wearable Devices Based on-Body Status, Location, and/or Orientation.

(56) References Cited

OTHER PUBLICATIONS

U.S. Appl. No. 15/057,762, filed Mar. 1, 2016, Brian Murphy et al., Perspiration Sensor.
U.S. Appl. No. 15/023,556, filed Mar. 21, 2016, Roozbeh Ghaffari, Conformal Sensor Systems for Sensing and Analysis.
U.S. Appl. No. 15/139,256, filed Apr. 26, 2016, Xia Li et al., Flexible Temperature Sensor Including Conformable Electronics.
U.S. Appl. No. 15/038,401, filed May 20, 2016, Huppert et al., Conformal Sensor Systems for Sensing and Analysis of Cardiac Activity.
U.S. Appl. No. 15/160,631, filed May 20, 2016, Lee et al., Ultra-Thin Wearable Sensing Device.
U.S. Appl. No. 15/183,513, filed Jun. 15, 2016, Wang et al., Moisture Wicking Adhesives for Skin Mounted Devices.
U.S. Appl. No. 15/189,461, filed Jun. 22, 2016, Ghaffari et al., Method and System for Structural Health Monitoring.
U.S. Appl. No. 15/208,444, filed Jul. 12, 2016, McGrane et al., Conductive Stiffener, Method of Making a Conductive Stiffener, and Conductive Adhesive and Encapsulation Layers.
U.S. Appl. No. 15/238,488, filed Aug. 16, 2016, Sun et al., Wearable Heat Flux Devices and Methods of Use.
U.S. Appl. No. 15/119,559, filed Aug. 17, 2016, Elolampi et al., Multi-Part Flexible Encapsulation Housing for Electronic Devices.
U.S. Appl. No. 15/272,816, filed Sep. 22, 2016, Pindado et al., Method and System for Crowd-Sourced Algorithm Development.
U.S. Appl. No. 15/284,960, filed Sep. 30, 2016, Ghaffari et al., Method and System for Interacting with a Virtual Environment.
U.S. Appl. No. 15/286,129, filed Oct. 5, 2016, Ghaffari et al., Method and System for Neuromodulation and Stimulation.
U.S. Appl. No. 15/108,861, filed Jun. 29, 2016, McMahon et al, Encapsulated Conformal Electronic Systems and Devices, and Methods of Making and Using the Same.
U.S. Appl. No. 15/369,627, filed Dec. 5, 2016, Ghaffari et al., Cardiac Catheter Employing Conformal Electronics for Mapping.
U.S. Appl. No. 15/369,668, filed Dec. 5, 2016, Ghaffari et al., Cardiac Catheter Employing Conformal Electronics for Mapping.
U.S. Appl. No. 15/373,159, filed Dec. 8, 2016, Ghaffari et al., Catheter Balloon Methods and Apparatus Employing Sensing Elements.
U.S. Appl. No. 15/373,162, filed Dec. 8, 2016, Ghaffari et al., Catheter Balloon Methods and Apparatus Employing Sensing Elements.
U.S. Appl. No. 15/373,165, filed Dec. 8, 2016, Ghaffari et al., Catheter Balloon Methods and Apparatus Employing Sensing Elements.
U.S. Appl. No. 15/405,166, filed Jan. 12, 2017, Rafferty et al., Electronics for Detection of a Condition of Tissue.
U.S. Appl. No. 15/413,218, filed Jan. 23, 2017, Rafferty et al, Electronics for Detection of a Condition of Tissue.
U.S. Appl. No. 15/412,993, filed Jan. 23, 2017, Rafferty et al., Embedding Thin Chips in Polymer.
U.S. Appl. No. 29/592,481, filed Jan. 31, 2017, Li et al., Electronic Device Having Antenna.
U.S. Appl. No. 15/433,873, filed Feb. 15, 2017, Rafferty et al., Electronics for Detection of a Condition of Tissue.
U.S. Appl. No. 15/437,964, filed Feb. 21, 2017, Raj et al., System, Devices, and Method for On-Body Data and Power Transmission.
U.S. Appl. No. 15/437,967, filed Feb. 21, 2017, Raj et al., System, Device, and Method for Coupled Hub and Sensor Node On-Body Acquisition of Sensor Information.
U.S. Appl. No. 15/457,852, filed Mar. 13, 2017, Dalal et al., Discrete Flexible Interconnects for Modules of Integrated Circuits.
U.S. Appl. No. 15/464,006, filed Mar. 20, 2017, Ghaffari et al., Systems, Methods, and Devices Using Stretchable or Flexible Electronics for Medical Applications.
U.S. Appl. No. 15/491,379, filed Apr. 19, 2017, Ghaffari et al., Method and System for Measuring Perspiration.
U.S. Appl. No. 15/498,941, filed Apr. 27, 2017, De Graff et al., Systems, Methods, and Devices Having Stretchable Integrated Circuitry for Sensing and Delivering Therapy.
U.S. Appl. No. 15/526,375, filed May 12, 2017, Aranyosi et al., System, Device, and Method for Electronic Device Activation.
U.S. Appl. No. 15/614,469, filed Jun. 5, 2017, Hsu et al., Conformal Electronics Including Nested Serpentine Interconnects.
U.S. Appl. No. 15/661,172, filed Jul. 27, 2017, Ghaffari et al., Catheter Balloon Employing Force Sensing Elements.
U.S. Appl. No. 15/806,162, filed Nov. 7, 2017, Hsu et al., Strain Isolation Structures for Stretchable Electronics.
U.S. Appl. No. 15/812,880, filed Nov. 14, 2017, Fastert et al., Conformal Electronics Integrated With Apparel.
U.S. Appl. No. 15/850,129, filed Dec. 21, 2017, Arora et al., Extremely Stretchable Electronics.
U.S. Appl. No. 15/850,523, dated Dec. 21, 2017, Huppert et al., Buffered Adhesive Structures for Wearable Patches.
U.S. Appl. No. 15/869,371, dated Jan. 12, 2018, Ives, Utility Gear Including Conformal Sensors.
U.S. Appl. No. 15/875,556, filed Jan. 19, 2018, Kacyvenski et al., Motion Sensor and Analysis.
U.S. Appl. No. 15/889,009, filed Feb. 5, 2018, Dalal et al., Flexible Electronic Circuits With Embedded Integrated Circuit Die and Methods of Making and Using the Same.
U.S. Appl. No. 15/921,076, filed Mar. 14, 2018, Huppert et al., Conformal Sensor Systems for Sensing and Analysis of Cardiac Activity.
U.S. Appl. No. 12/968,637, filed Dec. 15, 2010, J. Rogers, High-Speed, High-Resolution Electrophysiology In-Vivo Using Conformal Electronics.
U.S. Appl. No. 13/492,636, filed Jun. 8, 2012, J. Rogers, Flexible and Stretchable Electronic Systems for Epidermal Electronics.
U.S. Appl. No. 14/521,319, filed Oct. 22, 2014, J. Rogers, Stretchable and Foldable Electronic Devices.
U.S. Appl. No. 14/706,733, filed May 7, 2015, J. Rogers, Stretchable and Foldable Electronic Devices.
U.S. Appl. No. 15/084,112, filed Mar. 29, 2016, J. Rogers, Controlled Buckling Structures in Semiconductor Interconnects and Nanomembranes for Stretchable Electronics.
U.S. Appl. No. 15/339,338, filed Oct. 31, 2016, J. Rogers, A Stretchable Form of Single Crystal Silicon for High Performance Electronics on Rubber.
U.S. Appl. No. 15/470,780, filed Mar. 27, 2017, J. Rogers, Printed Assemblies of Ultrathin, Microscale Inorganic Light Emitting Diodes for Deformable and Semitransparent Displays.
U.S. Appl. No. 14/640,206, filed Jun. 30, 2017, R. Nuzzo, Methods and Devices for Fabricating and Assembling Printable Semiconductor Elements.
U.S. Appl. No. 15/805,674, filed Nov. 7, 2017, Litt et al., Flexible and Scalable Arrays for Recording and Modulating Physiologic Activity.

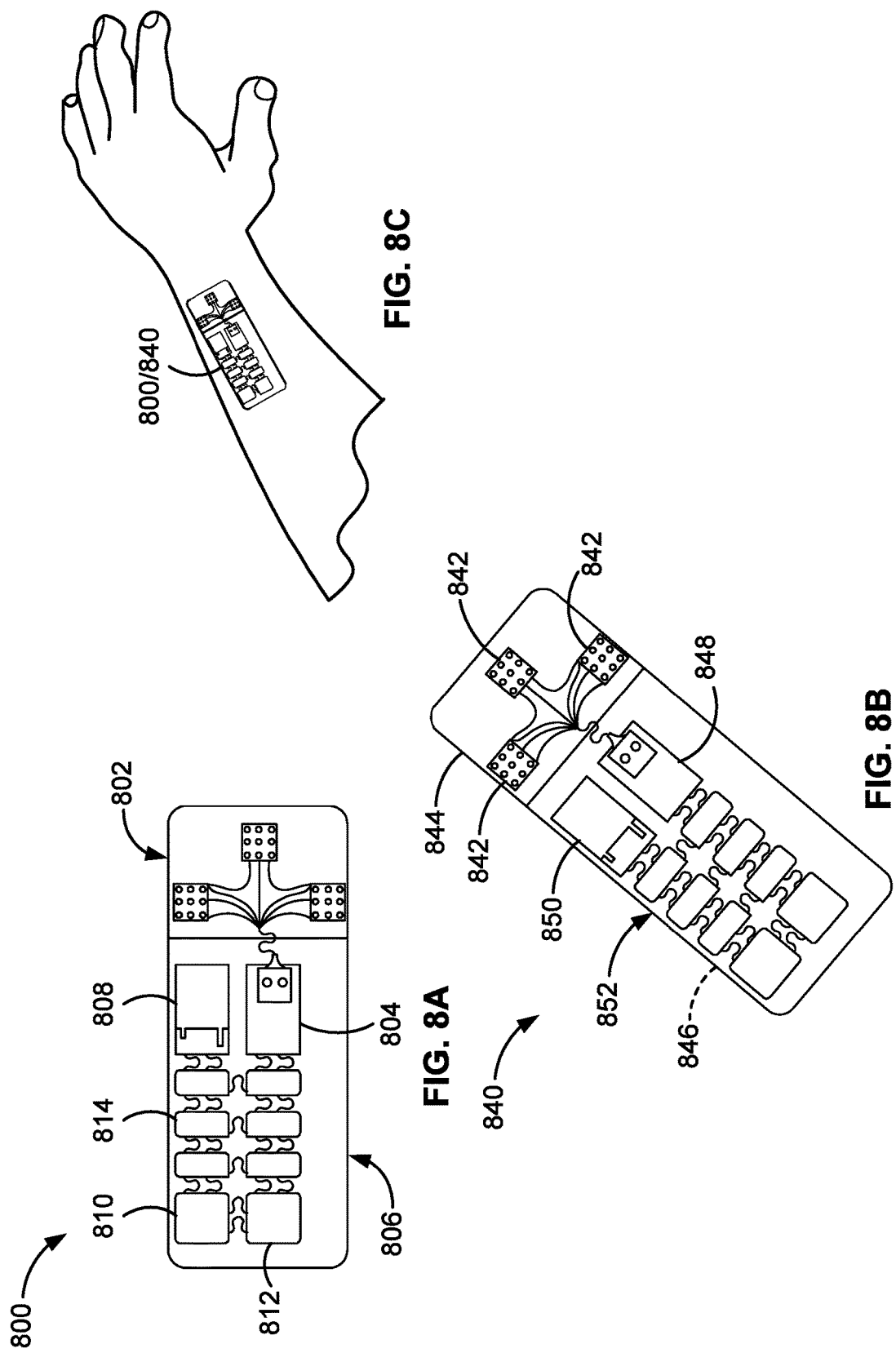

CONFORMAL SENSOR SYSTEMS FOR SENSING AND ANALYSIS OF CARDIAC ACTIVITY

CROSS-REFERENCE TO RELATED APPLICATIONS

This application is a continuation of U.S. patent application Ser. No. 15/038,401, filed on May 20, 2016, now allowed, which is the U.S. national stage of International Application No. PCT/US2014/066810, filed on Nov. 21, 2014, which claims the benefit of and priority to U.S. Provisional Patent Application No. 61/907,973, filed on Nov. 22, 2013, and U.S. Provisional Patent Application No. 61/907,991, filed on Nov. 22, 2013, each of which is incorporated herein by reference in its entirety and for all purposes.

TECHNICAL FIELD

The present disclosure relates generally to integrated circuits (IC) and IC sensor systems. More particularly, aspects of this disclosure relate to systems, methods and devices utilizing flexible and stretchable electronics for sensing and analysis.

BACKGROUND

Integrated circuits (IC) are the cornerstone of the information age and the foundation of today's information technology industries. The integrated circuit, a.k.a. "microchip," is a set of interconnected electronic components, such as transistors, capacitors, and resistors, which are etched or imprinted onto a tiny wafer of semiconducting material, such as silicon or germanium. Integrated circuits take on various forms including, as some non-limiting examples, microprocessors, amplifiers, Flash memories, application specific integrated circuits (ASICs), static random access memories (SRAMs), digital signal processors (DSPs), dynamic random access memories (DRAMs), erasable programmable read only memories (EPROMs), and programmable logic. Integrated circuits are used in innumerable products, including personal computers, laptop and tablet computers, smartphones, flat-screen televisions, medical instruments, telecommunication equipment, networking equipment, airplanes, watercraft and automobiles.

Advances in integrated circuit technology and microchip manufacturing have led to a steady decrease in chip size and an increase in circuit density and circuit performance. The scale of semiconductor integration has advanced to the point where a single semiconductor chip can hold tens of millions to over a billion devices in a space smaller than a U.S. penny. Moreover, the width of each conducting line in a modern microchip can be made as small as a fraction of a nanometer. The operating speed and overall performance of a semiconductor chip (e.g., clock speed and signal net switching speeds) has concomitantly increased with the level of integration. To keep pace with increases in on-chip circuit switching frequency and circuit density, semiconductor packages currently offer higher pin counts, greater power dissipation, more protection, and higher speeds than packages of just a few years ago.

Conventional microchips are generally rigid structures that are not designed to be bent or stretched during normal operating conditions. Likewise, most microchips and other integrated circuit modules are typically mounted on a printed circuit board (PCB) that is similarly rigid. Processes using rigid IC's and rigid PCB's are generally incompatible for applications requiring stretchable or bendable electronics. Consequently, many schemes have been proposed for embedding microchips on or in a flexible polymeric substrate to create a flexible electronic circuit system. To ensure constant and reliable electrical connections between individual IC modules, many flexible circuits employ stretchable and bendable interconnects that remain intact while the system stretches and bends. This, in turn, enables many useful device configurations not otherwise possible with rigid silicon-based electronic devices.

High quality medical sensing and analysis has become important in the diagnoses and treatment of a variety of medical conditions, including conditions related to the digestive system (e.g., liver and stomach), the cardiovascular system (e.g., heart and arteries), the nervous system (e.g., brain and spinal cord), and the like. Current medical sensing devices suffer from various disadvantages due to a lack of sophistication in sensing, analysis and therapeutic technology. One disadvantage is that many contemporary sensing and analysis devices are unable to achieve direct and conformal contact with the body of the patient. The inability to achieve direct or conformal contact is typically attributable to the rigid nature of the devices and accompanying circuitry. Such rigidity prevents these devices from coming into conforming and direct contact with human tissue, which may change shape, size, and/or orientation, and may be soft, pliable, curved, and/or irregularly shaped. This, in turn, can compromise the accuracy of measurements and the effectiveness of treatment. Thus, devices, systems and methods that employ flexible and/or stretchable systems for medical sensing, analysis and diagnostics would be desirable.

SUMMARY

Systems, apparatuses and methods are provided for monitoring an individual using one or more conformal sensor device. Disclosed herein, for example, are systems, methods, and apparatuses utilizing flexible electronics technology that is configured as conformal sensors for sensing, measuring, or otherwise quantifying cardiac activity. The conformal sensors also can be configured for detecting and/or quantifying motion of a body part (or other object) that is related to cardiac activity. In an example, the conformal sensors can be configured as conformal cardiac sensors. Conformal cardiac sensors can be used for sensing, measuring, or otherwise quantifying, cardiac activity and/or the motion of at least one body part and/or muscle activity that is related to cardiac activity. The example conformal cardiac sensors provide conformal sensing capabilities, providing mechanically transparent close contact with a surface (such as the skin or other portion of the body) to improve measurement and/or analysis of physiological information. For at least some implementations, the conformal cardiac sensors are formed as patches which couple directly to the patient. Specific implementations may employ multiple cardiac sensor devices (e.g., a variety of conformal sensor patches) to simultaneously or substantially simultaneously take measurements from multiple locations on the body. These patches can be flexible and stretchable, and can be formed from flexible electronics and conformal electrodes disposed in or on a flexible and/or stretchable substrate. In various examples, conformal electrodes are formed integral with a conformal cardiac sensor or are made separate/separable from a conformal cardiac sensor. The systems, methods and apparatuses described herein can be configured for use with human subjects and non-human subjects. Moreover, at least some of the disclosed conformal cardiac sensors can be mounted directly to and caused to conform with a portion of the skin or other portion of the body.

Aspects of the present disclosure are directed to conformal cardiac sensor devices for analyzing cardiac activity of a user. In one embodiment, the conformal cardiac sensor device includes at least one flexible substrate that is configured to couple to the user. At least one heart sensor component is embedded on or within the at least one flexible substrate. The heart sensor component(s) is configured to directly contact a portion of skin of the user, measure electrical activity that is indicative of cardiac activity of the user and output a signal indicative thereof. At least one biometric sensor component is embedded on or within the at least one flexible substrate. The biometric sensor component(s) is configured to measure physiological activity that is indicative of cardiac activity of the user. At least one microprocessor is embedded on or within the at least one flexible substrate. The at least one microprocessor is communicatively coupled to the at least one heart sensor component and the at least one biometric sensor component and operable to execute microprocessor executable instructions for controlling the measurement of electrical and physiological activity indicative of cardiac activity of the user. The conformal cardiac sensor device also includes at least one wireless communication component that is embedded on or within the at least one flexible substrate. The wireless communication component(s) is operable to transmit data indicative of the measurements obtained by the heart sensor component and the biometric sensor component.

According to other aspects of the present disclosure, conformal cardiac sensor assemblies for analyzing cardiac activity of an individual are presented. In one embodiment, the conformal cardiac sensor assembly includes a flexible substrate that is operable to attach to a portion of the individual, and a power supply that is attached or coupled to the flexible substrate. A microprocessor is attached or coupled to the flexible substrate and operable to execute microprocessor executable instructions. The conformal cardiac sensor assembly also includes a sensor component that is attached or coupled to the flexible substrate and configured to measure an electrical variable or a physiological variable, or both, indicative of cardiac activity of the individual. A therapeutic component is attached or coupled to the flexible substrate and configured to provide medicinal treatment to the individual based, at least in part, on the measurements obtained by the sensor component. The therapeutic component can trigger other forms of therapy based on cardiac activity of the user (e.g., initiate a soothing environment with calming music and lighting responsive to a conformal cardiac sensor sensing rapid or inordinate cardiac activity (tachycardia)).

Other aspects of the present disclosure are directed to conformal cardiac sensor systems for monitoring cardiac activity a user. In one embodiment, the conformal cardiac sensor system includes one or more memory devices storing microprocessor executable instructions, and one or more microprocessors electrically coupled to the one or more memory devices and operable to execute the microprocessor executable instructions. The conformal cardiac sensor system also includes one or more first sensor devices electrically coupled to the one or more microprocessors and operable to obtain one or more first measurements indicative of cardiac activity of the user. In addition, one or more second sensor devices are electrically coupled to the one or more microprocessors and operable to obtain one or more second measurements indicative of cardiac activity of the user. One or more wireless communication components are electrically coupled to the one or more microprocessors and operable to transmit data indicative of the measurements obtained by the one or more first and second sensor devices. One or more power supplies are electrically coupled to and operable to power the one or more memory devices, the one or more microprocessors, the one or more first and second sensor devices, and the one or more wireless communication components.

Any of the disclosed configurations, including those described in the preceding paragraphs, may include any of the following options (singly or in any combination): at least one therapeutic component embedded on or within the at least one flexible substrate, the at least one therapeutic component being configured to provide medicinal treatment to the user based, at least in part, on the measurements obtained by the at least one heart sensor component and the at least one biometric sensor component; at least one therapeutic component configured to administer to the user an emollient, a pharmaceutical drug or other drug, a biologic material, or other therapeutic material, or any combination thereof; an emollient, pharmaceutical drug or other drug, biologic material, or other therapeutic material delivered to the user in response to a detected occurrence of a predetermined triggering event; an emollient, pharmaceutical drug or other drug, biologic material, or other therapeutic material delivered to the user transdermally; an amount of emollient, pharmaceutical drug or other drug, biologic material, or other therapeutic material delivered to the user that is calibrated, correlated or otherwise modified based on a magnitude of the detected occurrence of the predetermined triggering event; at least one feedback component embedded on or within the at least one flexible substrate, the at least one feedback component being configured to analyze the measurements obtained by the at least one heart sensor component and the at least one biometric sensor component and provide diagnostic information or other physiological information to the user based on the analyzed measurements; at least one feedback component configured to display to the user an indication of the user's overall fitness, VO2 max, cardiovascular demand, energy expenditure, activity level, quality of sleep, stress level, heart plasticity or abnormality, or disordered breathing, or any combination thereof.

Any of the disclosed configurations, including those described in the preceding paragraphs, may include any of the following options (singly or in any combination): the least one first/heart sensor component including an electromyography (EMG) component, an electrocardiogram (EKG) component, or an electroencephalogram (EEG) component, or any combination thereof; the least one second/biometric sensor component including an accelerometer module, a gyroscope module, a muscle activation measurement module, or any combination thereof; at least one power supply embedded on or within the at least one flexible substrate and operable to power the heart sensor component, the biometric sensor component, the microprocessor and the wireless communication component; at least one memory device embedded on or within the at least one flexible substrate and storing the microprocessor executable instructions; the heart sensor component including a plurality of conformal electrodes embedded on or within the at least one flexible substrate, wherein the plurality of conformal electrodes is configured to directly contact the portion of skin of the user; the at least one flexible substrate is a stretchable polymeric patch surrounding the at least one heart sensor component, the at least one biometric sensor component, the at least one microprocessor, and the at least one wireless communication component.

The above summary is not intended to represent each embodiment or every aspect of the present disclosure. Rather, the foregoing summary merely provides an exemplification of some of the novel aspects and features set forth herein. The above features and advantages, and other features and advantages of the present disclosure, will be readily apparent from the following detailed description of representative embodiments and modes for carrying out the present invention when taken in connection with the accompanying drawings and the appended claims.

BRIEF DESCRIPTION OF THE DRAWINGS

FIGS. 8A and 8B are illustrations of representative conformal sensor patches for monitoring cardiac activity in accord with aspects of the present disclosure.

FIG. 8C shows an example implementation of the conformal sensor patches of FIGS. 8A and 8B.

DETAILED DESCRIPTION OF THE ILLUSTRATED EMBODIMENTS

Figure 1A:
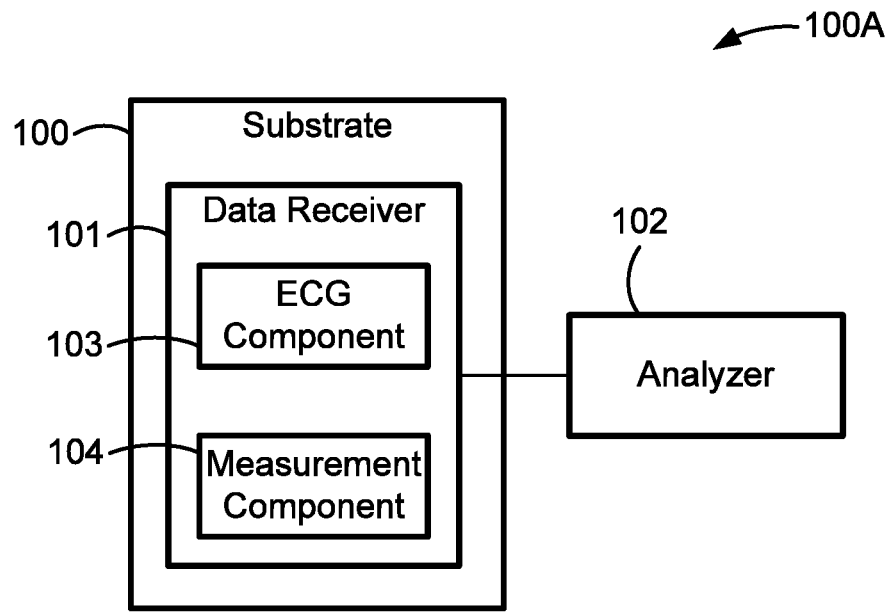
FIGS. 1A-1D are block diagrams illustrating examples of systems and devices for monitoring the cardiac activity of an individual in accord with aspects of the present disclosure.

This disclosure is susceptible of embodiment in many different forms. There are shown in the drawings, and will herein be described in detail, representative embodiments with the understanding that the present disclosure is to be considered as an exemplification of the principles of the present disclosure and is not intended to limit the broad aspects of the disclosure to the embodiments illustrated. To that extent, elements and limitations that are disclosed, for example, in the Abstract, Summary, and Detailed Description sections, but not explicitly set forth in the claims, should not be incorporated into the claims, singly or collectively, by implication, inference or otherwise. For purposes of the present detailed description, unless specifically disclaimed or logically prohibited: the singular includes the plural and vice versa; and the words "including" or "comprising" or "having" mean "including without limitation." Moreover, words of approximation, such as "about," "almost," "substantially," "approximately," and the like, can be used herein in the sense of "at, near, or nearly at," or "within 3-5% of," or "within acceptable manufacturing tolerances," or any logical combination thereof, for example.

It should be understood that any and all combinations of the features, functions and concepts discussed in detail herein are contemplated as being part of the inventive subject matter (provided such concepts are not mutually inconsistent). For example, although differing in appearance, the individual systems and devices and functional componentry depicted and discussed herein can each take on any of the various forms, optional configurations, and functional alternatives described above and below with respect to the other disclosed embodiments, unless explicitly disclaimed or otherwise logically prohibited. Following below are more detailed descriptions of various concepts related to, and embodiments of, inventive methods, apparatuses and systems for analysis of data indicative of cardiac activity, as non-limiting examples, for such applications as diagnosis, treatment, training and/or clinical purposes. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

The terms "flexible" and "stretchable" and "bendable," including roots and derivatives thereof, when used as an adjective to modify electrical circuitry, electrical systems, and electrical devices or apparatuses, are meant to encompass electronics that comprise at least some components having pliant or elastic properties such that the circuit is capable of being flexed, stretched and/or bent, respectively, without tearing or breaking or compromising their electrical characteristics. These terms are also meant to encompass circuitry having components (whether or not the components themselves are individually stretchable, flexible or bendable) that are configured in such a way so as to accommodate and remain functional when applied to a stretchable, bendable, inflatable, or otherwise pliant surface. In configurations deemed "extremely stretchable," the circuitry is capable of stretching and/or compressing and/or bending while withstanding high translational strains, such as in the range of −100% to 100%, −1000% to 1000%, and, in some embodiments, up to −100,000% to +100,000%, and/or high rotational strains, such as to an extent of 180° or greater, without fracturing or breaking and while substantially maintaining electrical performance found in an unstrained state.

Disclosed herein are systems, methods, and apparatuses utilizing conformal electronics technology that is configured as conformal sensors for sensing, measuring, or otherwise quantifying cardiac activity. In an example, a conformal cardiac sensor can be used for sensing, measuring and/or otherwise quantifying specific movement events of portions of the body. In another example, one or more of the systems, methods, and apparatuses described herein can be configured to use the results of analysis of data indicative of cardiac activity, or the motion of at least one body part and/or muscle activity that is related to cardiac activity, for such applications as medical diagnosis, medical treatment, physical activity, sports, physical therapy and/or clinical purposes. Data gathered using disclosed conformal cardiac sensors based on sensing the cardiac activity, or the motion of at least one body part and/or muscle activity that is related to cardiac activity, along with data gathered by sensing other physiological measures of the body, can be analyzed to provide useful information related to medical diagnosis, medical treatment, physical state, physical activity, sports, physical therapy, and/or clinical purposes. When sensing is performed using a thin, conformal, and wearable cardiac sensor, such as those described herein, and measurement devices including such sensors, these measures and metrics can be unimpeded by the size, weight or placement of the measurement devices.

At least some of the systems, methods, and devices described herein provide for creating, building, and deploying thin and conformal electronics that are useful in a wide variety of applications both inside the body and outside the body, through detection of cardiac activity, or the motion of at least one body part and/or muscle activity that is related to cardiac activity. At least some of the example conformal cardiac sensors include silicon-based and other electronics in new form factors allowing for the creation of very thin and conformal devices.

Systems, methods, and apparatuses described herein, including conformal cardiac sensors, can be configured to monitor cardiac activity, or motion of at least one body part and/or muscle activity that is related to cardiac activity, and to gather measured data values indicative of the monitoring. The monitoring can be performed in real-time, at different time intervals, randomly, continuously, and/or when requested. In addition, the example systems, methods, and apparatuses described herein can be configured to store the measured data values to a memory of the system and/or communicate (transmit) the measured data values to an external memory or other storage device, a network, and/or an off-board computing device. In any example herein, the external storage device can be a server, including a server in a data center. Non-limiting examples of a computing device applicable to any of the example systems, apparatus or methods according to the principles herein include smartphones, tablet computers, laptop computers, personal computers, personal digital assistants, slates, e-readers or other electronic reader, an Xbox®, a Wii®, or other game system(s), or other hand-held or worn computing device.

At least some of the disclosed systems, methods, and apparatuses can be used to provide ultra-thin and conformal electrodes that, when combined with cardiac activity measurements, facilitate monitoring and diagnosis of subjects. This in turn, can better facilitate the diagnosis and treatment of such ailments as cardiac disease (more commonly referred to as "heart disease"), vascular diseases of the brain and kidney, and peripheral arterial disease, as some non-limiting examples. In combination with pharmaceuticals, this information can be used to monitor and/or determine subject issues including compliance and effects.

For some embodiments, the conformal cardiac sensors are configured to provide a variety of sensing modalities. As an example, conformal cardiac sensors can be configured with sub-systems such as telemetry, power, power management, processing, as well as construction and materials. A wide variety of multi-modal sensing systems that share similar design and deployment can be fabricated based on the example conformal electronics. An example conformal cardiac sensor system includes electronics for performing at least one measurement related to cardiac activity, including an electrical activity measurement, an accelerometry measurement, or a muscle activation measurement, or any combination of the three. Additionally or alternatively, a conformal cardiac sensor system can include electronics for performing at least one other measurement, such as but not limited to heart rate measurements, temperature measurements, hydration level measurements, neural activity measurements, conductance measurements, environmental measurements, and/or pressure measurements. For instance, disclosed conformal sensors are configured to perform one or more or all of these different types of measurements.

An example cardiac sensor system includes an accelerometer, such as but not limited to a single-axis accelerometer and/or a 3-axis accelerometer, for providing accelerometry measurements. As another non-limiting example, the accelerometry component may be a 3-D accelerometer. Optionally or alternatively, the example cardiac sensor system includes one or more gyroscopes. The example cardiac sensor system can be disposed proximate to a body part or other object, and data collected based on the cardiac activity and/or the motion of at least one body part and/or muscle activity that is related to cardiac activity is analyzed. In a non-limiting example, a cardiac sensor system is configured to combine cardiac activity sensing in the form of a heart rate monitor and electrocardiogram (ECG) for a variety of applications. In an example implementation, the cardiac sensor may also include components for measuring motion and/or muscle activity, such as an accelerometry component and/or an electromyography component. Other sensors that can be employed for monitoring cardiac activity include triboelectric sensors, ultrasonic sensors, acoustoelectric sensors and transducers, endocardial sensors, piezoelectric activity sensors, thoracic impedance sensors, and the like. A controller communicatively coupled with one or more or all of the disclosed sensors can be employed to sense a cardiac event or a precursor to a cardiac event (e.g., heart failure, a decompensation episode of ventricular dysfunction, cardiovascular collapse, etc.).

For ECG measurements, the electrical activity of a portion of cardiac tissue or any other tissue in communication with the heart, or other portion of the body related to cardiac activity, is measured and quantified. In some implementations, the ECG measurements are performed using electrodes mounted on, disposed proximate to, or placed in communication with a portion of cardiac tissue or any other tissue in communication with the heart, or other portion of the body related to cardiac activity. Electrical activity is monitored, for example, based on such features as spikes and/or dips in a wave pattern or patterns of an electrical signal. For instance, with each heartbeat, an electrical signal can spread from one portion of cardiac tissue to another. The traveling electrical signal can cause cardiac tissue to contract. As a result, the heart pumps blood. The process, and associated electrical signals, repeats with each new heartbeat. Analysis of the data indicative of the electrical signal from the ECG measurements can be used to provide information indicative of the state of cardiac activity. For example, the analysis of the data is used to provide information about at least one of: the regularity or pace of the cardiac activity (including the heart beats), the rhythm of cardiac activity (including whether it is steady or irregular), the strength, timing and/or pathway of the electrical signals related to cardiac activity as the electrical signal passes through portions of cardiac tissue. As non-limiting examples, the data indicative of cardiac activity is analyzed to provide information related to a condition of the heart, including information related to a heart attack, a stroke, an arrhythmia, heart failure, and/or any other condition or disorder affecting heart function.

Electronics for muscle activation monitoring can be configured, for example, to perform electromyography (EMG) measurements. The electronics for EMG can be implemented to provide a measure of muscle response or electrical activity in response to a stimulation of the muscle. In a non-limiting example, the EMG measurements are used to detect neuromuscular abnormalities. For EMG measurements, electrodes coupled to the example conformal cardiac sensors are disposed on, proximate to, or in communication with a portion of cardiac tissue or any other tissue in communication with the heart, or other portion of the body related to cardiac activity, and the electrical signals indicative of an EMG measurement is detected or otherwise quantified by the electrodes. The EMG can be performed to measure the electrical activity of muscle related to cardiac activity during rest, or during muscle activity, including a slight contraction and/or a forceful contraction. Muscle tissue may not produce electrical signals during rest, however, a brief period of activity can be observed when a discrete electrical stimulation is applied using an electrode disposed proximate to the cardiac tissue and/or other muscle related to cardiac activity. Conformal cardiac sensors can be configured to measure, via the EMG electrodes, an action potential. In an example, the action potential is the electrical potential generated when muscle cells are electrically or neurologically stimulated or otherwise activated. As muscle is contracted more forcefully, more and more muscle fibers are activated, producing varying action potentials. Analysis of the magnitude and/or shape of the waveform(s) of the action potentials measured can be used to provide information about cardiac activity (including a body part and/or a muscle involved in cardiac activity), including the number of muscle fibers involved. In an example, the analysis of the magnitude and/or shape of the waveforms measured using the conformal sensors are used to provide an indication of the ability of the cardiac tissue and/or other muscle related to cardiac activity to respond, e.g., to movement and/or to stimuli (including electrical stimuli). Analysis of spectral or frequency content of such signals can be further used to provide an indication of muscle activation and/or other tissue activity, and associated cardiac activity. This data or any other data described herein can be further filtered and/or compressed to reduce the amount of information to be stored.

For some embodiments, data indicative of the conformal sensor measurements, including the measured action potentials, can be stored in a resident memory device of the conformal sensor system and/or communicated or otherwise transmitted, e.g., wirelessly, to an external memory or other storage device, network, and/or off-board computing device. Conformal cardiac sensor systems disclosed herein can include one or more processing units that are configured to analyze the data indicative of the conformal sensor measurements, including the measured action potentials.

According to other aspects of the disclosed concepts, a conformal cardiac sensor system comprises electronics coupled to recording and stimulating electrodes for performing a nerve conduction study (NCS) measurement. An NCS measurement can be used to provide data indicative of the amount and speed of conduction of an electrical impulse through a nerve. Analysis of a NCS measurement can be used to determine nerve damage or destruction related to cardiac activity. In a NCS measurement, an impulse monitoring "recording" electrode can be coupled to a body part, or other object proximate to a nerve (or nerve bundle) of interest, or other tissue related to cardiac activity, and a pulse emitting "stimulating" electrode can be disposed at a known distance away from the recording electrode. The conformal sensor system can be configured to apply a mild and brief electrical stimulation to stimulate a nerve (or nerve bundle) of interest via the stimulating electrode(s). Measurement of the response of the nerve (or nerve bundle) of interest can be made via the recording electrode(s). The stimulation of the nerve (or nerve bundle) of interest and/or the detected response can be stored to a memory of the conformal sensor system and/or communicated (transmitted), e.g., to an external memory or other storage device, a network, and/or an off-board computing device.

The architecture of a conformal cardiac sensor system can include, for example, one or more sensor devices, power and/or power circuitry, wired and/or wireless communication devices, and at least one processing unit. In some examples, the power source can be a wireless power source. Non-limiting examples of other components of the conformal cardiac sensor system include at least one battery, a regulator, a memory (such as but not limited to a read-only memory, a flash memory, and/or a random-access memory), an input interface, an output interface, a communication module, a passive circuit component, an active circuit component, etc. One or more or all of the disclosed conformal cardiac sensor systems include at least one microcontroller and/or other integrated circuit component. In an example, the conformal cardiac sensor system comprises at least one coil, such as but not limited to a near-field communication (NFC) enabled coil. In another example, the conformal cardiac sensor system includes a radio-frequency identification (RFID) component. In an example, the conformal cardiac sensor system can include a dynamic NFC/RFID tag integrated circuit with a dual-interface, electrically erasable programmable memory (EEPROM).

FIGS. 1A through 1D of the drawings show non-limiting examples of cardiac sensor device and system configurations. As indicated above, each of the systems and devices depicted and discussed with respect to FIGS. 1A-1D can take on any of the other various forms, optional configurations, and functional alternatives described with respect to the other disclosed embodiments, unless explicitly disclaimed or otherwise logically prohibited. An example cardiac sensor device, designated generally at 100A in FIG. 1A, includes a data receiver 101 disposed on or in a substrate 100. The substrate 100 and/or the data receiver 101 can be configured to conform to a portion of cardiac tissue, an object proximate to cardiac tissue, or any other tissue in communication with the heart, or other portion of the body related to cardiac activity, to which the data receiver 101 and the substrate 100 are coupled. The object is a body part, a secondary object, and/or a muscle group, for example. Data receiver 101 can include one or more of any conformal sensor component according to the principles of any of the examples and/or figures described herein. In an example, the data receiver 101 includes a ECG component 103 and at least one other measurement component 104. Measurement component 104 comprises, in at least some implementations, at least one an accelerometer, at least one heart rate monitor (including a muscle activation monitor), and/or at least one of any other sensor disclosed herein. The at least one ECG component 103 and/or at least one measurement component 104 can be used to measure data indicative of a cardiac activity (including at a portion of cardiac tissue or any other tissue in communication with the heart, or other portion of the body related to cardiac activity).

The example device of FIG. 1A also includes an analyzer 102. As illustrated, the analyzer 102 is configured to quantify the data indicative of cardiac activity, other physiological data, and/or analysis of such data indicative of cardiac activity, and/or physiological data, according to the principles described herein. In one example, the analyzer 102 is disposed on or in the substrate 100 with the data receiver 101, while in another example the analyzer 102 is disposed proximate to or remote from the substrate 100 and data receiver 101. In the representative implementation of the device in FIG. 1A, the analyzer 102 is configured to quantify or otherwise analyze the data indicative of the ECG measurement and/or the other component measurement (such as an accelerometry measurement, a heart rate measurement, and/or muscle activation monitoring) to provide an indication of cardiac activity. Analyzer 102 of FIGS. 1A-1D includes, as some non-limiting examples, a central processing unit (CPU), one or more microprocessors (e.g., a master processor, a slave processor, and a secondary or parallel processor), and/or any combination of hardware, software, or firmware disposed resident to or remote from the sensor device.

Figure 1B:
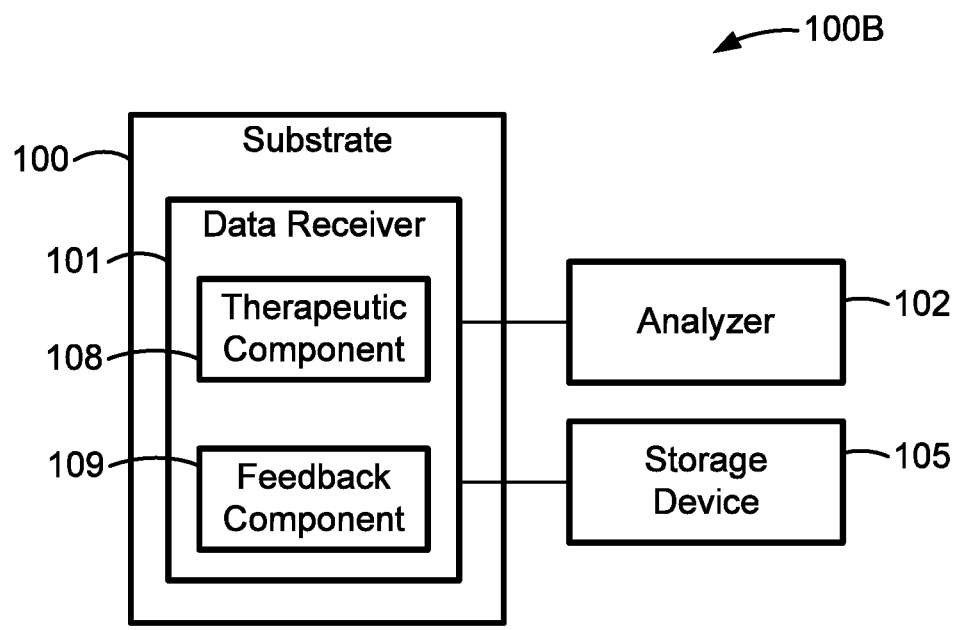

FIG. 1B shows another representative cardiac sensor device 100B, which includes a substrate 100, a data receiver 101, an analyzer 102, and a storage module 105. Optionally, the device 100B may further comprise a therapeutic component 108 and/or a feedback component 109. Therapeutic component 108 may utilize the data received by data receiver 101 and analyzed by the data analyzer 102 to provide therapeutic, pharmacological or other medicinal treatment to the user as described in further detail below (e.g., to administer or deliver an emollient, a pharmaceutical drug or other drug, a biologic material, or other therapeutic material). Conversely, feedback component 109 may utilize the data received by data receiver 101 and analyzed by the data analyzer 102 to provide diagnostic information, physiological information and/or other feedback on cardiac activity and/or other electrophysiological measurements to the user regarding, e.g., any of the characteristics identified in FIGS. 12-26. The storage module 105 illustrated in FIG. 1B is configured, for example, to include a memory to save data from the data receiver 101 and/or the analyzer 102. In some implementations, the storage device 105 is any type of non-volatile memory. Any of the storage devices 105 illustrated in the drawings can include flash memory, solid state drives, removable memory cards, erasable programmable read only memory (EEPROM), random access memory (RAM), or any other type of computer-readable medium, or any combination thereof. In certain examples, the storage device 105 is removable from the device. In some implementations, the storage device 105 is local to the device while in other examples it is remote. For example, the storage device 105 can be the internal memory of a computing device. In the various examples herein, the computing device may be a smartphone, a personal computer, a tablet computer, a slate computer, a personal digital assistant (PDA), an e-reader or other electronic reader, an Xbox®, a Wii®, or other game system(s), or other hand-held or worn computing device. In this example, the device may communicate with the external computing device via an application executing on the external computing device. In some implementations, the sensor data can be stored on the storage device 105 for processing at a later time. In some examples, the storage device 105 can include space to store processor-executable instructions that are executed any of the disclosed methods, functions, and operations, including to analyze data from the data receiver 101. In other examples, the memory of the storage device 105 can be used to store the measured data indicative of cardiac activity, other physiological data, or analysis of such data indicative of cardiac activity, or physiological data, according to the principles described herein.

Figure 1C:
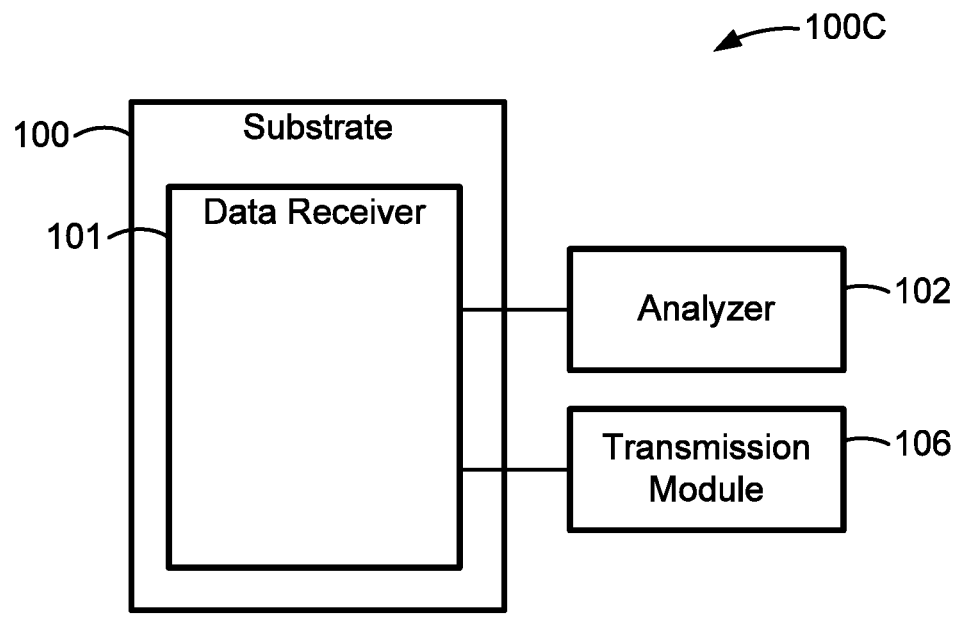

FIG. 1C shows yet another example of a cardiac sensor device 100C according to the principles disclosed herein. Sensor device 100C includes, for example, a substrate 100, a data receiver 101, an analyzer 102, and a transmission module 106. The transmission module 106 is configured to transmit data from the data receiver 101, the analyzer 102, and/or stored in a storage device (such as the storage device 105 of FIG. 1B), to an external memory or other storage device, a network, and/or an off-board computing device. In an example, the transmission module 106 can be a wireless transmission module. For such configurations, the transmission module 106 transmits data via wireless networks, radio frequency communication protocols, Bluetooth®, near-field communication (NFC), and/or optically using infrared or non-infrared LEDs. The data can be transmitted to an external memory or other storage device, a network, and/or an off-board computing device.

Figure 1D:
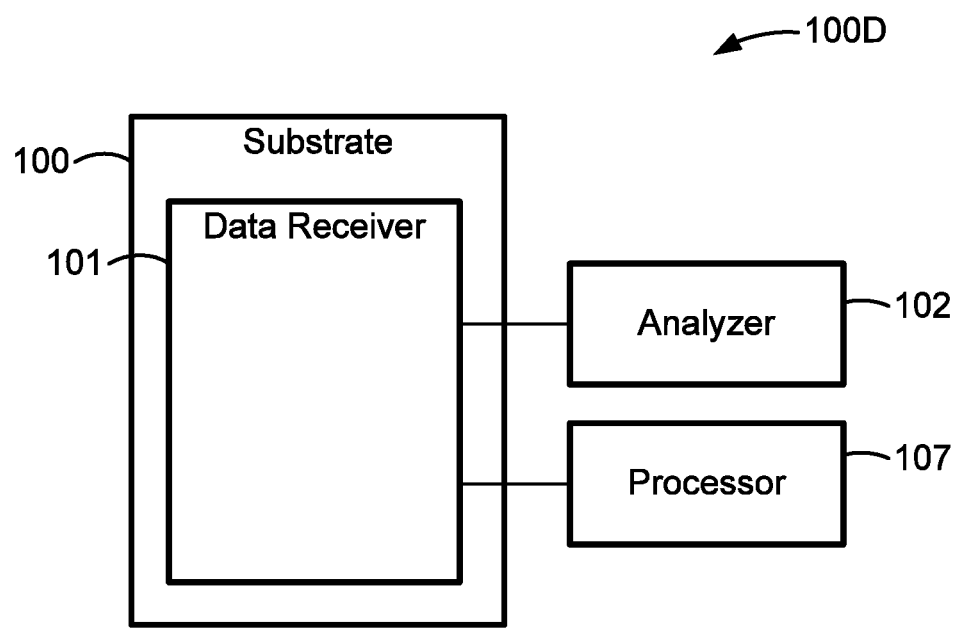

FIG. 1D shows yet another example system 100D that includes a substrate 100, a data receiver 101, an analyzer 102, and a processor 107. The data receiver 101 can receive data related to sensor measurement(s) from a sensor. In an example, the sensor is a conformal sensor. The processor 107 is configured, for example, to execute processor-executable instructions stored in a storage device 107 and/or within the processor 107 to analyze data indicative of cardiac activity, other physiological data, or analysis of such data indicative of cardiac activity, or other physiological data according to the principles described herein. In some implementations, the data can be directly received from the data receiver 101 or retrieved from a storage device (such as the storage device 105 of FIG. 1B). In one example, the processor is a component of the analyzer 102 and/or disposed proximate to the data receiver 101. In another example, the processor 107 is external to the system, such as in a computing device that downloads and analyzes data retrieved from the system. The processor 107 can execute processor-executable instructions that quantify the data received by the data receiver 101.

Figure 2A:
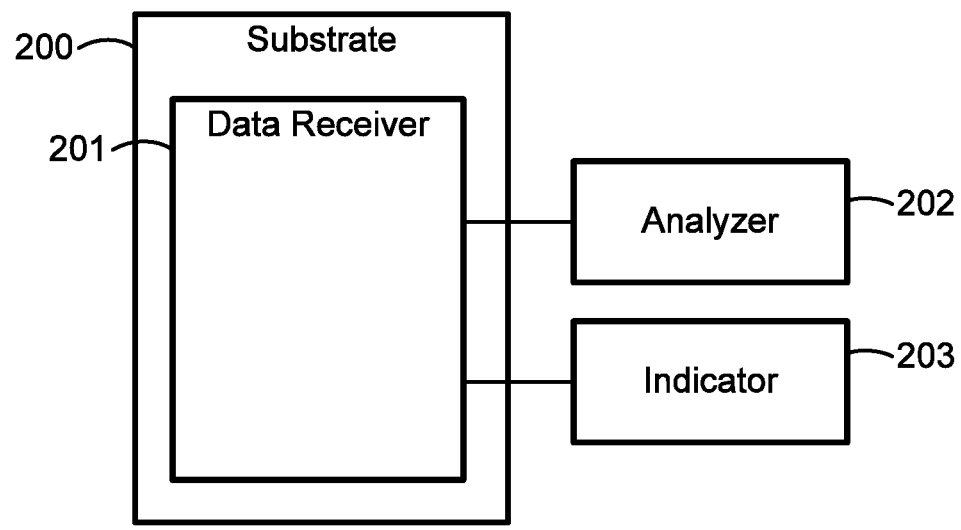
FIGS. 2A-2C are block diagrams illustrating examples of systems and devices for monitoring the cardiac activity of an individual and displaying data indicative of such cardiac activity in accord with aspects of the present disclosure.
Figure 2B:
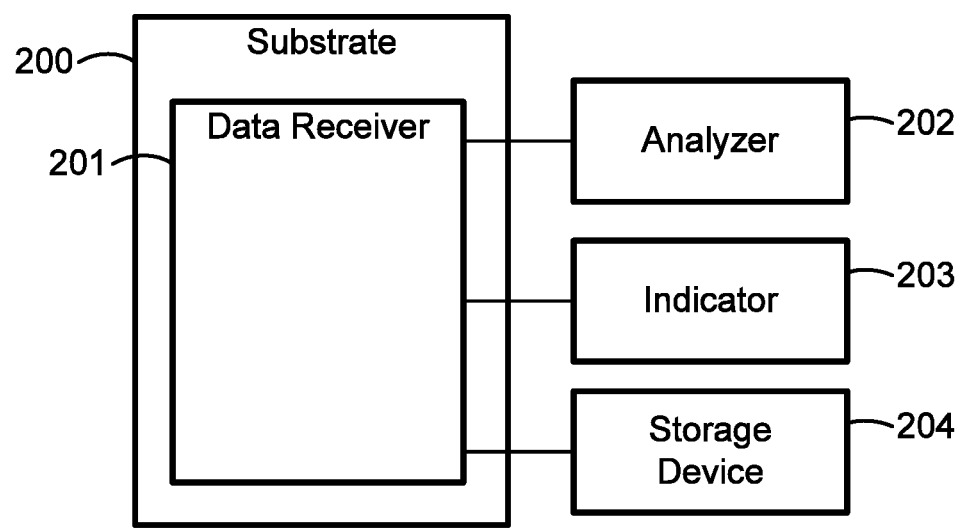
Figure 2C:
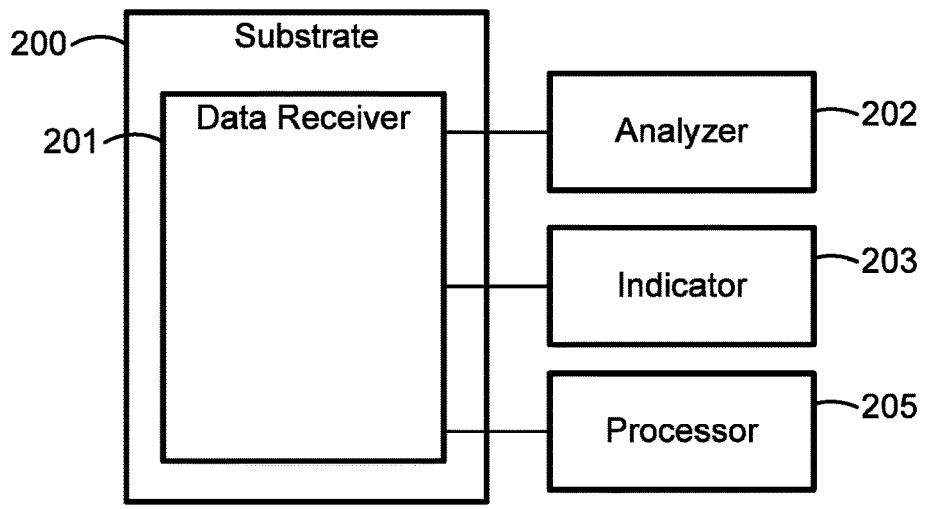

FIGS. 2A-2C show non-limiting examples of cardiac sensor system configurations that include an electronic display or other output device for displaying or otherwise outputting the data or analysis results from analysis of the data. The example systems of FIGS. 2A-2C include a substrate 200, a data receiver 201, an analyzer 202, and an indicator 203. As shown in the examples of FIGS. 2B-2C, the system can further include a processor 205 (see FIG. 2C), to execute the processor-executable instructions described herein, and/or a storage device 204 (see FIG. 2B), for storing processor-executable instructions and/or data from the analyzer 202 and/or one or more conformal sensors of the system.

The indicator 203 of the example systems of FIGS. 2A-2C can be used for displaying and/or transmitting data indicative of cardiac activity, other physiological data, and/or analysis of such data indicative of cardiac activity, or other physiological data, according to the principles described herein, and/or user information. In one example, the indicator 203 can comprise a liquid crystal display (LCD) device, a light emitting diode (LED) display device, or an electrophoretic display (such as e-ink), and/or a plurality of indicator lights. For example, the indicator 203 can include a series of LEDs. In some implementations, the LEDs range in color, such as from green to red. In this example, if performance does not meet a pre-determined threshold measure, a red indicator light can be activated and if the performance meets the pre-determined threshold measure, the green indicator light can be activated. In another example, indicator 203 may include a screen or other display that can be used to display graphs, plots, icons, or other graphic or visual representations indicative of the data or analysis results from analysis of the data.

In some implementations, as described above, the signaling of the indicator 203 is detectable to the human eye; in other implementations, it is not detectable by the human eye but can be detected using an image sensor. The indicator 203 may be configured to emit light outside the visible spectrum of the human eye (e.g., infrared) or to emit light that is too dim to be detected, as examples of indication methods substantially not detectable by the human eye. In these examples, the image sensor can be configured to detect such signals outside the viewing capabilities of a human eye. In various examples, the image sensor may be a component of a smartphone, a tablet computer, a slate computer, an e-reader or other electronic reader or hand-held or wearable computing device, a laptop, an Xbox®, a Wii®, or other game system(s).

Figure 3:
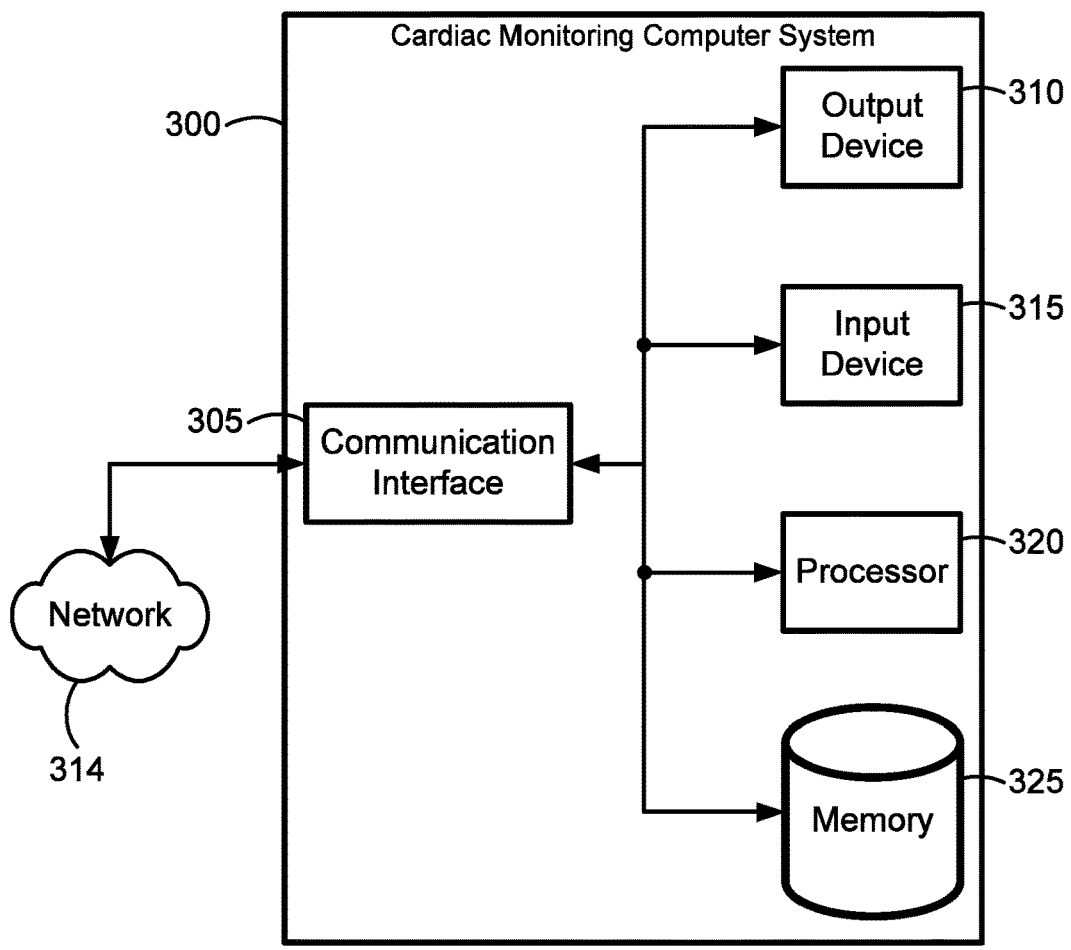
FIG. 3 is a diagrammatic illustration of a representative cardiac monitoring computer system for assisting in monitoring the cardiac activity of an individual with one more conformal cardiac sensors in accord with aspects of the present disclosure.

FIG. 3 shows the architecture of an example cardiac monitoring computer system 300 that may be employed to implement any of the example methods, computer systems, and apparatuses discussed herein. The computer system 300 of FIG. 3 includes one or more processors 320 communicatively coupled to one or more memory devices 325, one or more communications interfaces 305, one or more output devices 310 (e.g., one or more display units), and one or more input devices 315. In the computer system 300 of FIG. 3, the memory 325 may include any computer-readable storage media, and may store computer instructions such as processor-executable instructions for implementing the various functionalities described herein for respective systems, as well as any data relating thereto, generated thereby, or received via the communications interface(s) or input device(s). The processor(s) 320 shown in FIG. 3 may be used to execute instructions stored in the memory device(s) 325 and, in so doing, also may read from or write to the memory various information processed and/or generated pursuant to execution of the instructions.

The processor 320 of the computer system 300 shown in FIG. 3 also may be communicatively coupled to or control the communications interface(s) 305 to transmit and/or receive various information pursuant to execution of instructions. For some implementations, the communications interface(s) 305 is communicatively coupled to a network 314 to thereby allow the computer system 300 to transmit information to and/or receive information from other devices (e.g., other computers/computer systems). Network 314 can be a wired or wireless network, bus, or other data transmission means or communication means. The system of FIG. 3 may further include one or more communications interfaces to facilitate information flow between the components of the system 300. In some implementations, the communications interface(s) is configured (e.g., via various hardware components or software components) to provide a website as an access portal to at least some aspects of the computer system 300.

Output devices 310 of cardiac monitoring computer system 300 shown in FIG. 3 may be provided, for example, to allow information to be viewed or otherwise perceived in connection with execution of the instructions. The input device(s) 315 may be provided, for example, to allow a user to make manual adjustments, make selections, enter data or various other information, or interact in any of a variety of manners with the processor during execution of the instructions. The input device(s) 315 may take the form of, but is not limited to, switches, contacts, capacitive or mechanical components. In other examples, input device(s) 315 may use the measures from sensors to actuate controls of the system.

Figure 4:
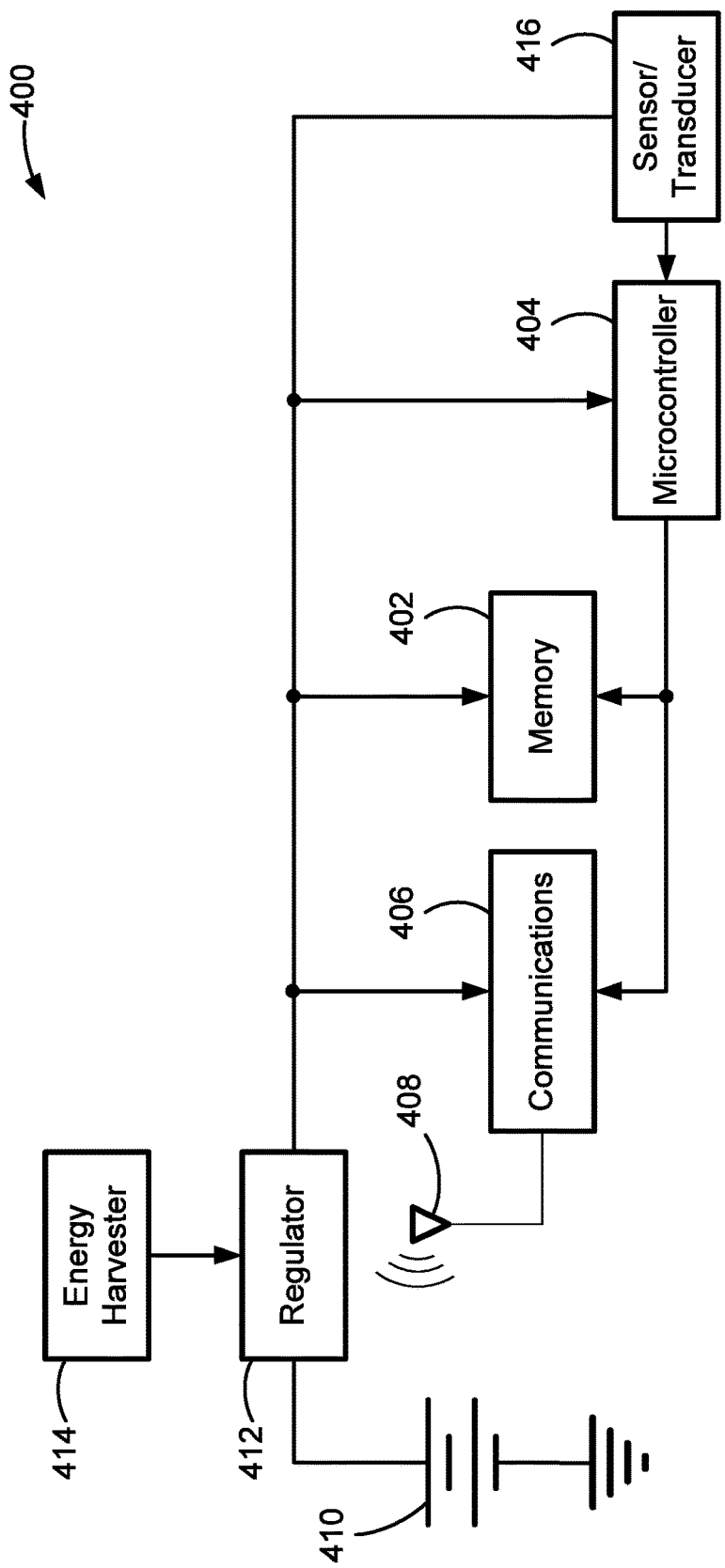
FIG. 4 is a diagrammatic illustration of a representative architecture of a conformal sensor system in accord with aspects of the present disclosure.

FIG. 4 shows a block diagram of a representative system-level architecture of an example cardiac sensor system 400 according to the principles herein. The example system 400 includes a memory 402, a microcontroller 404 (including at least one processing unit), a communications component 406 (including an antenna 408), a power supply 410 (i.e., a battery unit), a charge regulator 412 coupled with an energy harvester 414, and a sensor/transducer component 416. In a non-limiting example, the sensor/transducer component 416 includes cardiac sensor platform electronics for performing electrocardiogram (ECG) measurements, accelerometry measurements, and/or muscle activation measurements. Sensor/transducer component 416 may comprise at least one heart sensor component configured to measure electrical data indicative of cardiac activity of the user, and at least one biometric sensor component configured to measure physiological data indicative of cardiac activity of the user. For some configurations, the cardiac sensor system 400 includes at least one of the other types of sensor components disclosed herein or otherwise configured to perform any of the measurements disclosed herein. In the example of FIG. 4, the communications component 406 can include Bluetooth® communication or other wireless communication protocols and standards, at least one low-power microcontroller unit for controlling the recording of the ECG measurement(s), the accelerometry measurement(s), and/or the muscle activation measurement(s), and any other data associated with any other physiological parameter measured. In an example, there can be a respective microcontroller for controlling each different type of measurement.

Figure 5:
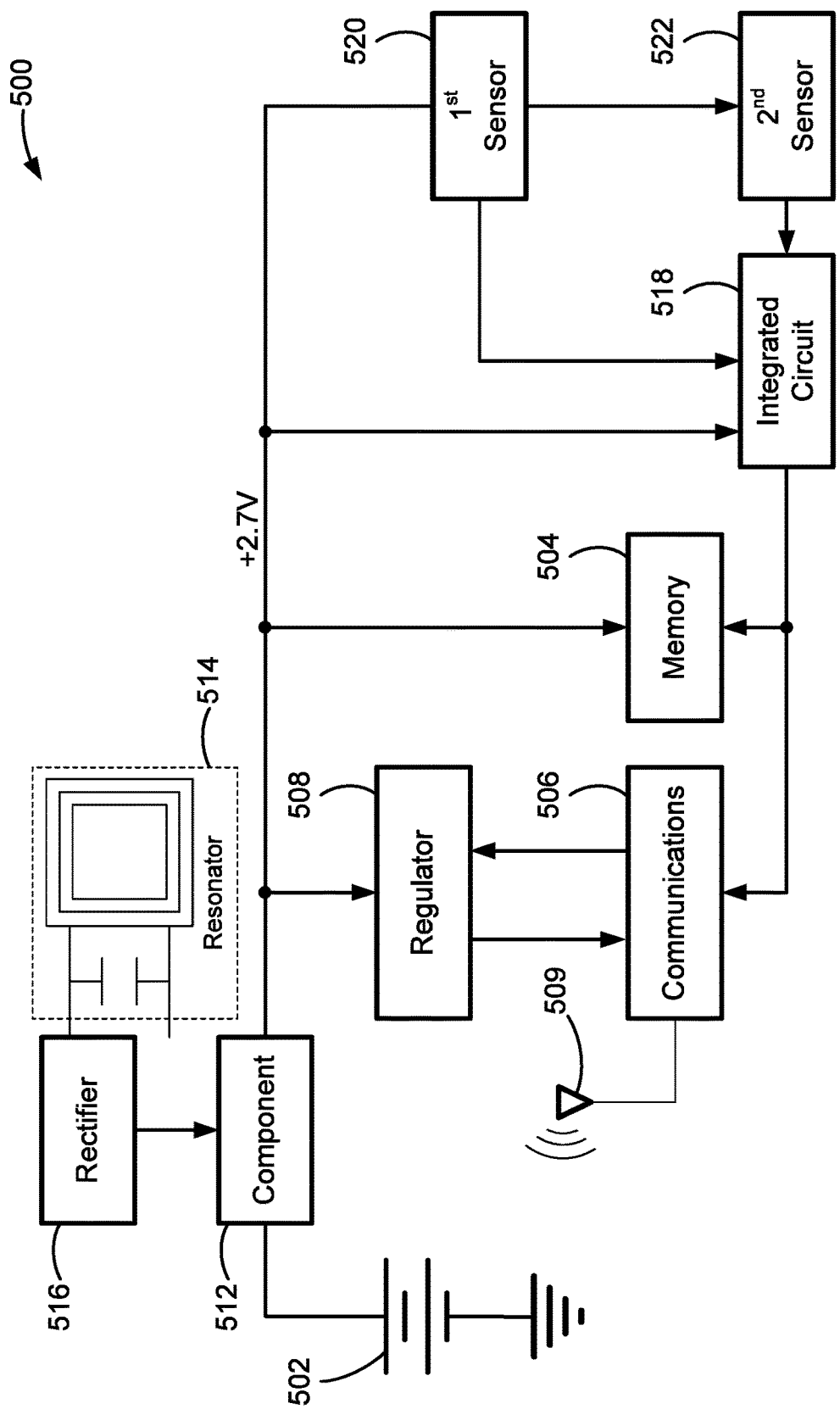
FIG. 5 is a diagrammatic illustration showing the components of a representative conformal cardiac sensor platform in accord with aspects of the present disclosure.

FIG. 5 shows non-limiting examples of the various components of a representative conformal cardiac sensor platform 500 for sensing, monitoring or otherwise determining indications of cardiac activity. In the example of FIG. 5, the cardiac sensor platform 500 incorporates an onboard battery unit 502 (e.g., supplying approximately 2.7V) coupled with, among other things, a memory 504 (e.g., a 32 megabyte (MB) flash memory), and a communication component 506 (e.g., a Bluetooth®/Bluetooth® Low Energy (BTLE) communication unit) that is coupled with an output regulator 508 and an antenna 509. Battery unit 502 may optionally be coupled to an energy harvester, battery charger, regulator, or the like, which are represented, singly and collectively, by component 512 in FIG. 5. The cardiac sensor platform 500 is shown coupled with a resonator 514 (such as, but not limited to, a 13.56 MHz resonator) and a full-wave rectifier 516. The cardiac sensor platform 500 further includes an integrated circuit component 518, which may be in the nature of or comprise a microcontroller, a Bluetooth®/BTLE stack on-chip, and firmware storing processor-executable instructions for implementation of conformal cardiac sensor measurements.

The example conformal cardiac sensor platform 500 of FIG. 5 employs a first sensor component 520 and, optionally, a second sensor component 522. In an example, first sensor component 520 comprises a 3-axis accelerometer with at least 3 sensitivity settings and a digital output. In this same example, second sensor component 522 comprises EMG sensing, EMG electrodes, and a digital output. Platform 500 may also include a low-power microcontroller unit for ECG measurements, a low-power microcontroller for EMG measurements, a low-power microcontroller unit for accelerometry measurements, and/or a low-power microcontroller for electrophysiological measurements. In some examples, the functions of a given component of the system, such as but not limited to the ECG, accelerometry, EMG, or other physiological measuring component, may be divided across one or more microcontrollers. The lines leading from the energy harvester/battery charger/regulator to the other components highlight modular design where different sensors (such as but not limited to EMG electrodes, EEG electrodes, electroencephalography (EEG) electrodes) can be used with similar set of microcontrollers, communications, and/or memory modules.

Figure 6:
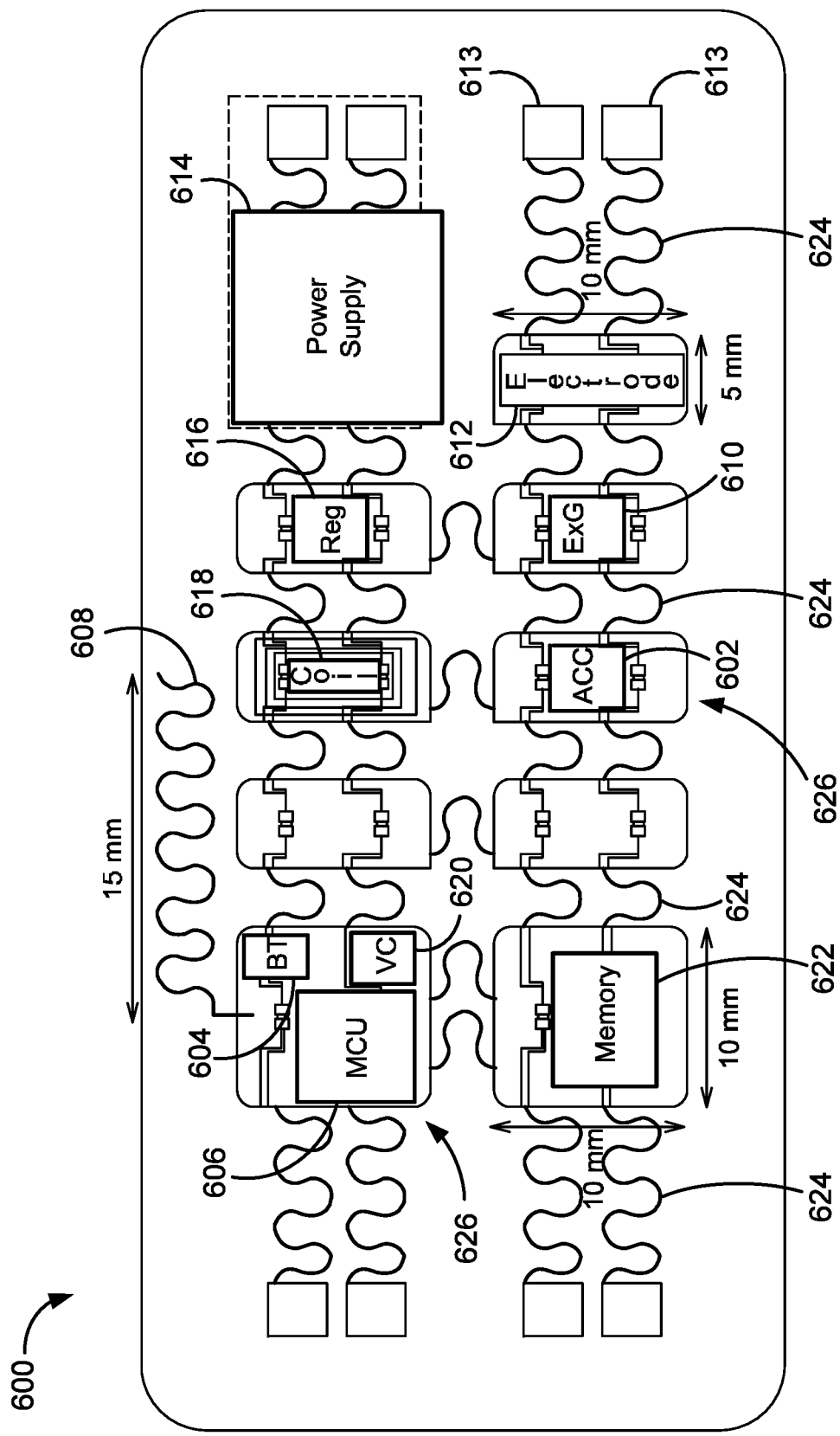
FIG. 6 is a schematic illustration of a representative architecture of a conformal sensor device in accord with aspects of the present disclosure.

FIG. 6 presents a schematic drawing of the mechanical layout and system-level architecture of an example conformal cardiac sensor device, designated generally as 600, that is configured as a rechargeable patch. The conformal cardiac sensor electronics technology disclosed herein can be designed and implemented with various mechanical and electrical layouts for multifunctional platforms and, thus, is not per se limited to the layout presented in FIG. 6. Examples of some such conformal electronics layouts and configurations are presented, for example, in commonly owned U.S. patent application Ser. No. 13/844,767, to Roozbeh Ghaffari et al. and entitled "Catheter Balloon Employing Force Sensing Elements," and commonly owned U.S. patent application Ser. No. 12/575,008, to Roozbeh Ghaffari et al. and entitled "Catheter Balloon Having Stretchable Integrated Circuitry and Sensor Array," both of which are incorporated herein by reference in their respective entireties and for all purposes. Conformal devices including flexible electronics technology typically integrate stretchable/bendable form factors using IC designs embedded in or on flexible polymeric substrates/layers. These substrates/layers are formulated to protect the circuits from strain and to achieve mechanical flexibility in an ultra-thin cross-section. For example, the device can be configured with thicknesses on the order of about 1 mm or less on average. In other examples, the patch can be configured with thinner or thicker cross-sectional dimensions.

The device architecture of FIG. 6 employs one or more reusable modules containing electronic surface-mount technology (SMT) components, including a biometric sensor component 602 (e.g., an accelerometer module and/or a gyroscope module), a wireless communication module 604, a microcontroller 606, an antenna 608 (such as, but not limited to, a stretchable monopole antenna), conformal electrode arrays 610 and 612 for sensing, e.g., EMG, EEG and EKG signals, and a pair of electrode connectors 613. The conformal electrode arrays 610 and 612 (also referred to herein as "heart sensor components") can be reusable or disposable. The representative rechargeable patch 600 also includes a power supply module 614, such as but not limited to a LiPo Battery of approximately 2 mA-Hr or approximately 10 mA-Hr), a regulator module 616, a power transfer coil (such as but not limited to a 0.125 oz Cu coil with 1.5/2 mil trace/space ratio), a voltage controller module 620, and a memory module 622.

As shown in the example of FIG. 6, the components of the conformal cardiac sensor device are assembled in a "device island" arrangement, interconnected by stretchable interconnects 624. The stretchable interconnect can be configured, singly or collectively, as serpentine interconnects, zig-zag interconnects, rippled interconnects, buckled interconnects, helical interconnects, boustrophedonic interconnects, meander-shaped interconnects, or any other configuration that facilitates flexability. In any of the examples described herein, electrically conductive material (such as but not limited to the material of an electrical interconnect and/or an electrical contact) can be, but is not limited to, a metal, a metal alloy, a conductive polymer, or other conductive material. In any of the example structures described herein, the stretchable interconnects can have a thickness of about 0.1 µm, about 0.3 µm, about 0.5 µm, about 0.8 µm, about 1 µm, about 1.5 µm, about 2 µm, about 5 µm, about 9 µm, about 12 µm, about 25 µm, about 50 µm, about 75 µm, about 100 µm, or greater.

These components, in addition to comprising the aforementioned sensor, power, communication and other components, may include additional and alternative components, such as additional electrodes, additional electrode connectors, or any other example component according to the principles described herein. Stretchable interconnects 624 are electrically conductive to facilitate electrical communication between the various components of FIG. 6, or are electrically non-conductive to assist in maintaining a desired overall form factor or relative aspect ratio of the overall conformation of the conformal sensor device during or after being subjected to deformation forces, such as extension, compressive and/or torsional forces. The example of FIG. 6 also shows the differing shapes and aspect ratios of the island bases 626 that the components of the example conformal sensor can be disposed on, or otherwise coupled to, to provide the device islands.

For at least some desired applications, an encapsulant material can be introduced locally to any region or portion or component of the conformal sensor device 500, such as proximate to a portion of an electronic component or an interconnect of the conformal device. The encapsulant helps, for example, to protect the component from an applied stress or strain in the event of a deformation force being applied to the overall conformal device. For example, the encapsulant material can aid in adjusting a location of a neutral mechanical plane locally in the region of the component. Controlled placement of the neutral mechanical plane relative to a functional component can result in little to no stress or strain being exerted in the region of the component, when the overall conformal device is subjected to the deformation force.

As a non-limiting example, a portion of the conformal cardiac sensor device proximate to an electronic component may be encapsulated in a polyimide (PI), or other polymer or polymeric material, that can cause the neutral mechanical plane to coincide with the more fragile portions of the component. Non-limiting examples of applicable polymers or polymeric materials include a polyimide (PI), a polyethylene terephthalate (PET), a silicone, or a polyurethane. Other non-limiting examples of applicable polymers or polymeric materials include plastics, elastomers, thermoplastic elastomers, elastoplastics, thermostats, thermoplastics, acrylates, acetal polymers, biodegradable polymers, cellulosic polymers, fluoropolymers, nylons, polyacrylonitrile polymers, polyamide-imide polymers, polyarylates, polybenzimidazole, polybutylene, polycarbonate, polyesters, polyetherimide, polyethylene, polyethylene copolymers and modified polyethylenes, polyketones, poly(methyl methacrylate, polymethylpentene, polyphenylene oxides and polyphenylene sulfides, polyphthalamide, polypropylene, polyurethanes, styrenic resins, sulphone based resins, vinyl-based resins, or any combinations of these materials. In an example, a polymer or polymeric material herein can be a UV curable polymer or a silicone.

In determining the configuration of the overall conformal device, the dimensions of the components, the stiffness of the materials of the component, the dimensions and/or the stiffness of one or more interconnects, the stiffness properties of the encapsulant material, and/or location of placement of the encapsulant material, can be controlled to strategically cause the neutral mechanical plane to fall in a region of one or more components or interconnect(s) of the overall conformal device to prevent a stress or strain concentration near the fragile regions of the component(s) and/or the interconnects. In a non-limiting example, the fragile region is junction between an interconnect and an electronic component.

In any example implementation, the positioning of the neutral mechanical plane in any given region of the overall conformal device can be controlled to protect one or more of the electronically functional components of the overall conformal device structure from an applied stress or strain. The positioning of the neutral mechanical plane can be controlled locally at any electronic component of the overall conformal device by controlling parameters locally such as, but not limited to, at least one of: (a) type of material (stiffness) of an electronic component and/or dimensions of the electronic component; (b) type of material (stiffness) of the interconnect and/or shape of the interconnect; and (c) the use of an encapsulant, including choice of type of encapsulant material (stiffness) and/or choice of local placement of the encapsulant in the overall conformal device.

Figure 7B:
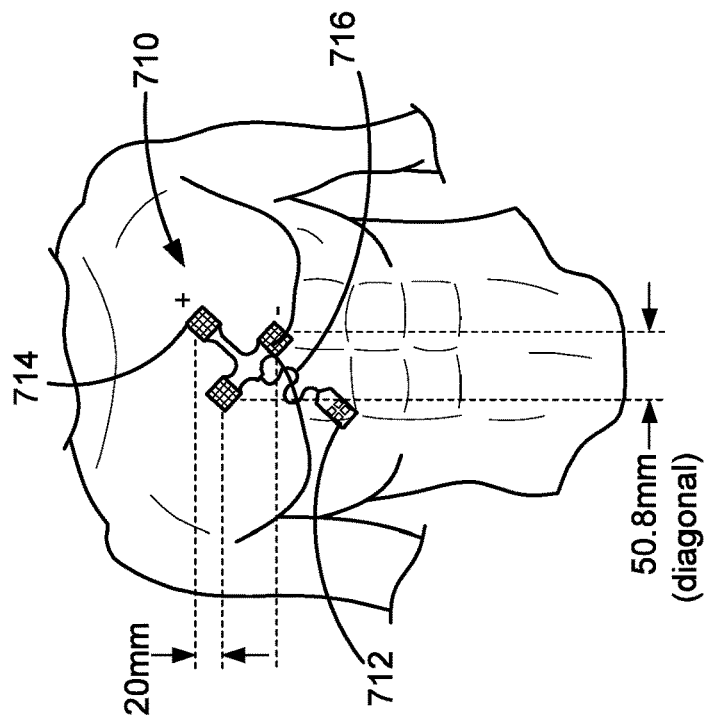
FIGS. 7A and 7B show some example implementations of conformal sensor systems in accord with aspects of the present disclosure.
Figure 7A:
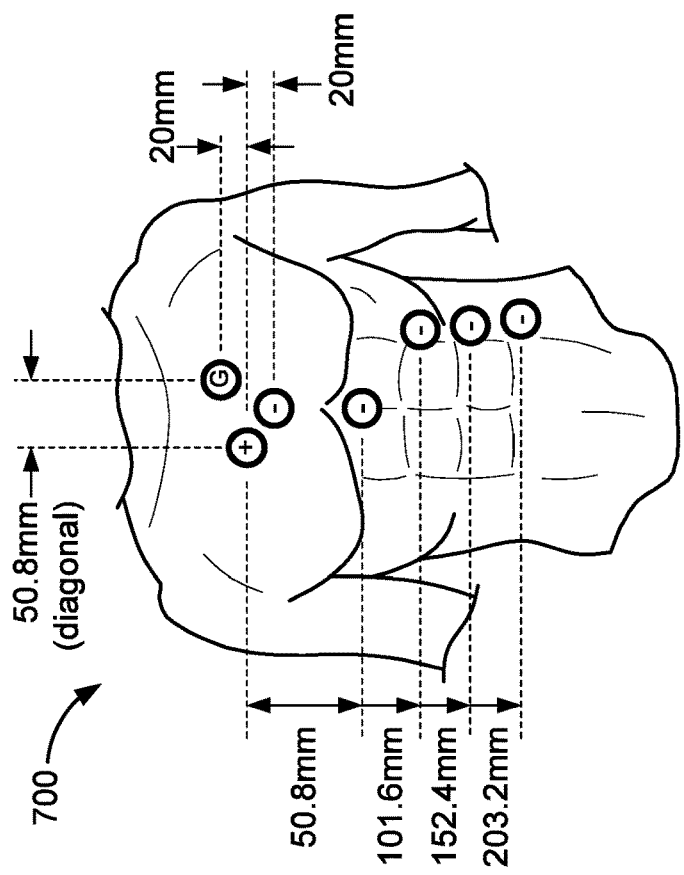
Figure 7C:
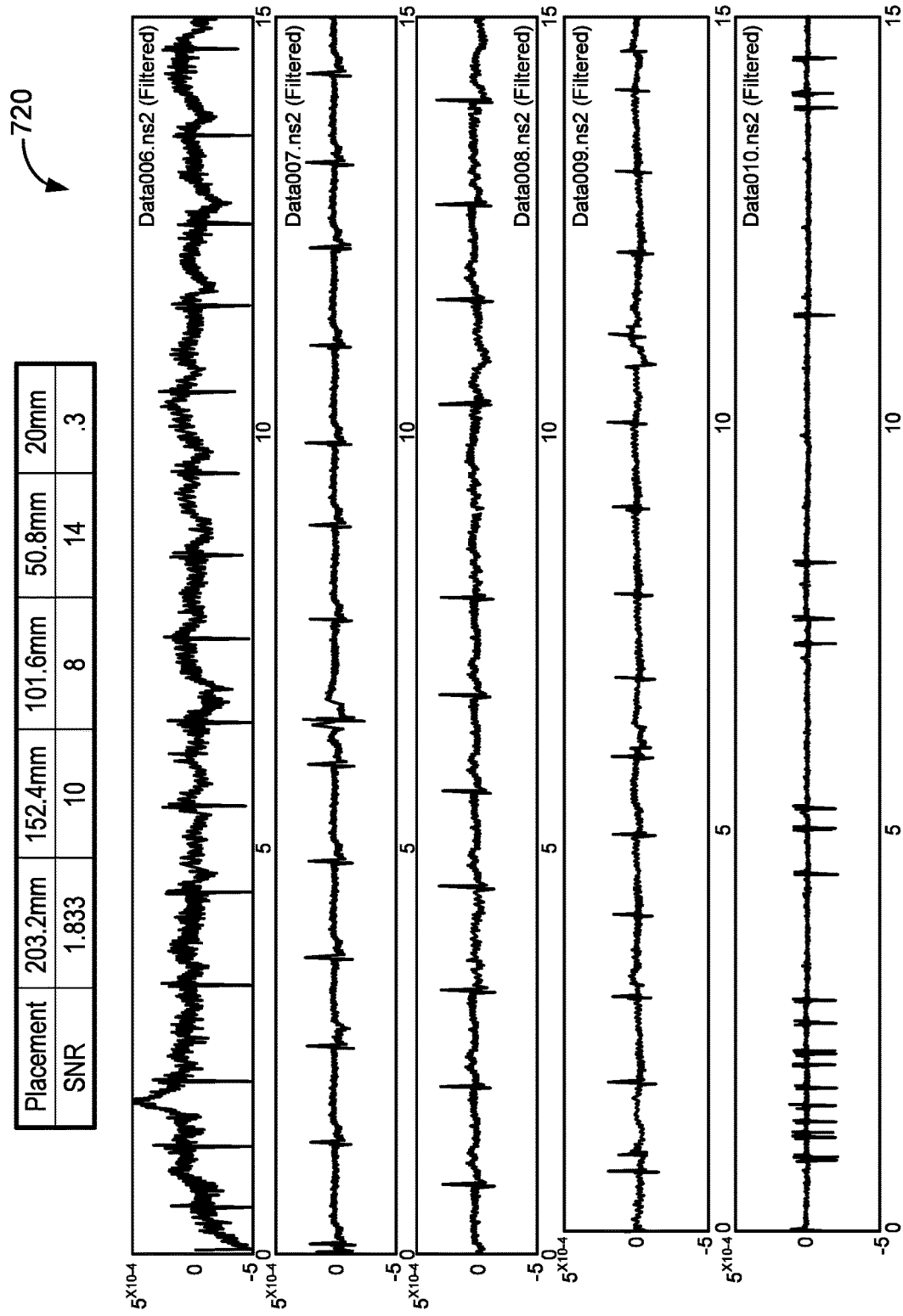
FIG. 7C presents a chart and graphs illustrating representative data taken by the conformal sensor systems of FIGS. 7A and 7B.
Figure 9A:
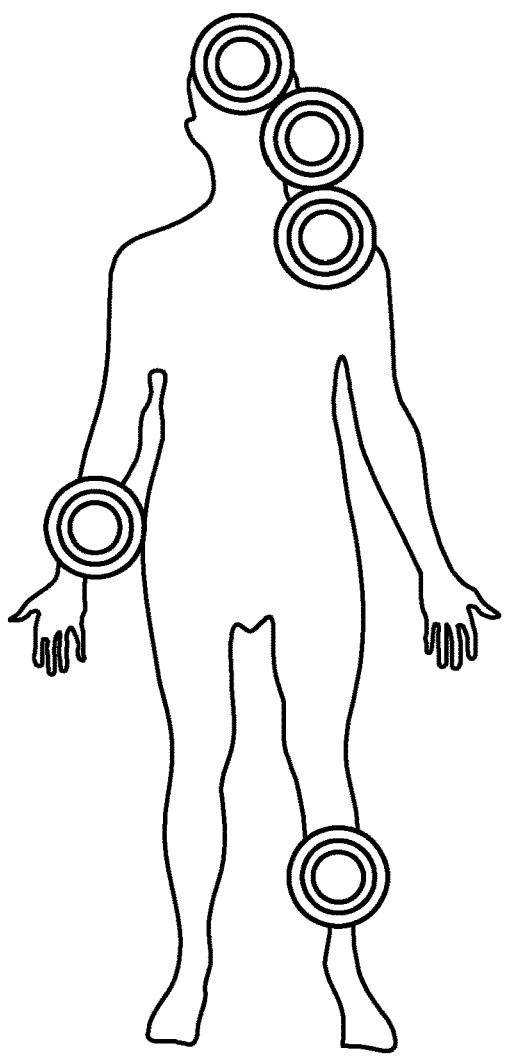
FIGS. 9A and 9B illustrate examples of placement of an example conformal sensor patch on a human body in accord with aspects of the present disclosure.
Figure 9B:
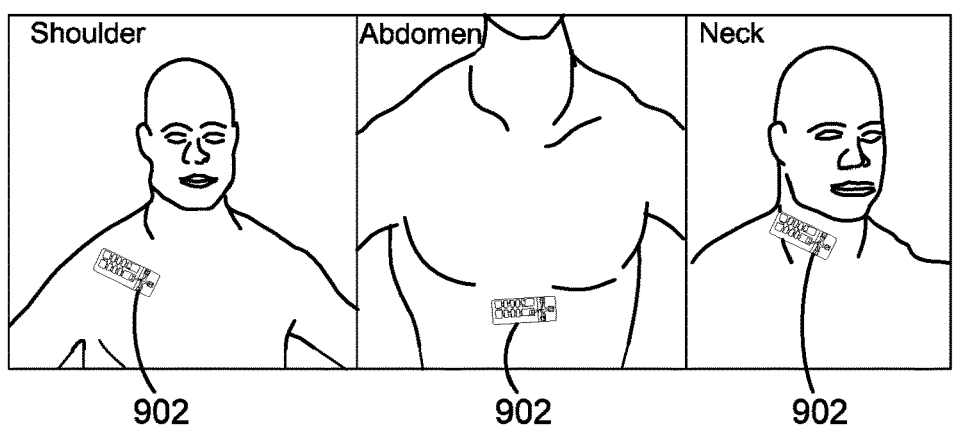

FIGS. 7A-7C show some example implementations of a conformal cardiac sensor system 700, including example placement of a conformal cardiac sensor patch 710 on a portion of the body and representative data 720 taken by the conformal sensor system. FIG. 7A shows how one can determine the placement/positioning of sensing electrodes on the body based, at least in part, on the relative distances between portions of the body. FIG. 7B shows an example conformal cardiac sensor patch 710, which includes a plurality of electrodes (e.g., three electrocardiogram (ECG) electrodes) disposed at defined positions on the upper torso (e.g., front thorax) of a human subject. The placement is determined, for example, based on measurements performed similarly to those depicted in FIG. 7A (e.g., at placement intervals based on similar ratios of positions) or according to any other technique in the art. FIG. 7B also shows examples of the placement of the ECG electrodes on the body. FIG. 7C shows non-limiting example measurements taken using the ECG electrodes relative to various positions on a body (e.g., as depicted in FIG. 7A). Because of the size and conformability of the patch, as well as the compact spacing of the sensor nodes within the patch, it is contemplated that the cardiac sensor patch be placed anywhere on the patient's chest or body, as indicated in the discussion of FIGS. 9A and 9B below.

The example conformal cardiac sensor device 710 can include disposable ECG electrodes 714, a re-usable connector 716 to mechanically and electrically couple the ECG electrodes with a main portion/body of the conformal cardiac sensor device 716, and a cardiac sensor unit 712 forming the main portion of the cardiac sensor device. In the example of FIG. 7B, the main portion 712 of the cardiac sensor unit is formed as a conformal patch. Similar to the architecture 600 of FIG. 6 described above, the example cardiac sensor unit 710 can be configured to include at least one battery, at least one microprocessor, at least one memory, at least one wireless communication device, and passive circuitry. In an example, the battery may be rechargeable, thereby causing the cardiac sensor unit 710 to be rechargeable. As a non-limiting example, the average thickness of the reusable patch can be about 1 mm thick and the lateral dimensions can be about 2 cm by about 10 cm. In other examples, the patch can be configured to have other dimensions, form factors, and/or aspect ratios (e.g., thinner, thicker, wider, narrower, or many other variations).

Turning next to FIGS. 8A-8C, there are shown example implementations of conformal cardiac sensor systems and conformal cardiac sensor patches. FIG. 8A shows one representative implementation of a cardiac sensor system formed, at least in part, as a conformal cardiac sensor patch 800 with selectively removable and disposable electrodes 802, a reusable connector 804 for electrically coupling the electrodes to a reusable and rechargeable conformal sensor unit 806 formed as a conformal patch. The rechargeable conformal sensor unit 806 can further include numerous additional and alternative components, including those described above with respect to FIGS. 1A-1D, 2A-2C and 4-6. For example, the unit 806 is shown comprising a battery 808, a microprocessor 810, a memory 812, wireless communication module 814, and/or other active and passive circuitry. According to the illustrated example, the average thickness of the reusable patch can be about 1 mm thick with lateral dimensions of about 2 cm (wide) by about 10 cm (long). In other examples, the patch can be configured to have other dimensions, form factors, and/or aspect ratios (e.g., thinner, thicker, wider, narrower, or many other variations).

FIG. 8B shows another example of a cardiac sensor system formed, at least in part as a bipartite conformal cardiac sensor bandage 840 with at least two separable sub-components. The exemplar system of FIG. 8B employs a conformal cardiac sensor bandage 840 that includes example EMG electrodes 842 disposed on or in an ultrathin sticker 844. A conformal cardiac sensor unit 852 is disposed on or in a skin adhesive 846. The EMG electrodes 842 are communicatively coupled to the conformal cardiac sensor unit 852 via an electrode connector 848. Similar to the configuration presented in FIG. 8A, the rechargeable cardiac sensor unit 852 of FIG. 8B can include at least one battery 850, at least one microprocessor, at least one memory, at least one wireless communication module, and/or passive or active circuitry. In this example, the average thickness of the reusable patch is about 1 mm thick with lateral dimensions of about 2 cm (wide) by about 10 cm (long). In other examples, the patch can be configured to have other dimensions, form factors, and/or aspect ratios (e.g., thinner, thicker, wider, narrower, or many other variations).

FIG. 8C presents a possible location for placement for a conformal cardiac sensor patch 800/bandage 840 on a portion of a subject's body (e.g., on the left forearm of a human patient). The data gathered using placement of the cardiac sensor system in this manner may be used to provide cardiovascular data, physiological data, muscle activity data, or other data that can be used alone or in combination with other data to assess cardiac activity and conditions associated therewith. As described in greater detail below, the conformal cardiac sensor patch can be used to provide intermittent, systematic, real-time and/or continuous feedback on cardiac activity and/or other electrophysiological measurements related to cardiac activity.

Turning next to FIG. 9A, there are shown some other example placements of example conformal cardiac sensor devices 902 and systems on the body of a human. As shown in the example of FIG. 9A, a conformal cardiac sensor patch/bandage/device can be placed at various locations on the body. In various example implementations, the conformal cardiac sensor systems can be placed at various locations on the body to measure the signal to noise ratio associated with each sensor/location combination. The results of analysis of the data obtained from the measurements at each placement position can be used to determine an optimal location for obtaining a desirable signal to noise ratio. FIG. 9B shows various illustrations of a human torso (abdomen, thorax and shoulders), neck and chin with different anatomical locations where the example conformal cardiac sensor devices/systems can be deployed for measurements.

The example conformal electronics technology herein can be designed and implemented with various mechanical and electrical layouts for multifunctional platforms. The example devices including the conformal electronics technology can be integrated with various stretchable form factors using designs embedded in polymeric layers. These can be formulated to protect the circuits from strain and to achieve mechanical flexibility with ultra-thin profiles, such as but not limited to thicknesses of about 1 mm on average. In other examples, the patch can be configured with thinner or thicker cross-sectional dimensions. The example architecture can include a reusable module containing surface-mount technology (SMT) components, including ECG measuring components, accelerometer, wireless communication, microcontroller, antenna, coupled with disposable conformal electrode arrays for sensing EMG or other electrical measurements (such as but not limited to NCS and electroencephalogram (EEG) signals).

Processor-executable instructions development (including software, algorithms, firmware, etc.) can be configured to be specific for each platform using predicate algorithms as the basis of signal processing. Filters and sampling rates can be tuned and tested on rigid evaluation boards and then implemented with flexible designs. The example conformal cardiac sensors and conformal electrodes according to the principles described herein can be used, based on implementation of the processor-executable instructions, for monitoring, e.g., cardiac activity at various locations on the body, and/or analysis of data indicative of measurements from the monitoring.

There a various example parameters that can be taken by the conformal cardiac sensor devices, methods and systems disclosed herein. Standard reference measurements can be taken while one or more conformal cardiac sensors is/are mounted to a subject. Each condition can be repeated to generate reproducibility data. Precision and reproducibility of sensor measurement output can be determined based on, for example: (a) Pre-determined relative displacement of ECG electrodes on body and strength of ECG signal; (b) Body motion—X, Y, Z axis acceleration waveform in G's; (c) Muscle activity—muscle motion ON/OFF and ON-to-ON time. Optimal placement for each sensor can be determined, for example, for maximum signal detection. Optimal co-location placement for two or more of the sensors can be determined, for example, in a similar manner.

The example conformal cardiac sensors and conformal electrodes according to the principles described herein can be used to measure ECG and other metrics of cardiac activity (including a measure of heart rate and/or other electrical activity related to cardiac activity), other electrical activity, temperature, hydration level, neural activity, conductance, and/or pressure, with acceptable precision. Acceptable precision can be defined as operationalized as a high correlation (such as but not limited to $r \geq 0.8$) of these sensors with standard reference measurements of: electrocardiogram—a MAC 3500 12 Lead ECG Analysis System (GE Healthcare, AZ, USA)1, or similar; accelerometry—such as, but not limited to, a Shimmer3® base module (http://www.shimmersensing.com/) or similar or an external image-based body monitoring; electromyogram—a Grass P511AC, Amplifier (Grass Technologies, West Warwick, R.I., USA), or similar.

An optimal placement for each conformal cardiac sensor, including ECG electrodes, can be determined, for example, to yield high-quality, precise and reliable measurements. There can be at least one placement in which the example conformal cardiac sensors and conformal electrodes can be placed to yield precise and reliable measurements.

For cardiac activity, subjects can be measured while wearing one or more conformal cardiac sensors on standard references (ECG electrodes). The system may include a 3-axis accelerometer and/or EMG electrodes. The conformal cardiac sensor can be placed at selected locations on the body of the subject or other object to measure cardiac activity of the subject. Standard reference measurements can be taken while the conformal cardiac sensor is mounted. Conformal cardiac sensor patches/bandages/devices can be placed at selected body placement locations, including: chest or other portion of torso, inside wrist, calf, front left shoulder, rear left shoulder, left neck below the ear, and forehead (e.g., as shown in FIGS. 7A, 7B, 9A and 9B). Each condition can be repeated to generate reproducible data. Subjects can be measured for a period of time. In an example, the subject can be measured while performing a sequence of activities/movements, e.g., sit down, walk, hand movements, athletic activity, physical therapy movements, or any other movement described below. Conformal cardiac sensor and reference measurements can be analyzed to provide information indicative of the desired result, including the physical condition of the subject, the efficacy of a treatment or therapy being performed on the subject, the subject's readiness for physical activity or exertion, or proper cardiac condition for a sport or other exercise.

Example system, methods and devices are provided herein that can be used to estimate the sensitivity, specificity, and/or positive and/or negative predictive values of algorithm(s) from the conformal cardiac sensors to predict, for example but not limited to selected metrics of the efficacy of a treatment or therapy being performed on the subject. The feasibility or acceptability of subjects wearing the conformal cardiac sensors can be monitored. Subjects' cardiac activity can be monitored while wearing the conformal cardiac sensors disposed on a body part or other object for a period of time (e.g., time on the order of minutes, an hour, or a number of hours, while at rest or while carrying out a series of motions, activities and/or tasks.

Figure 10B:
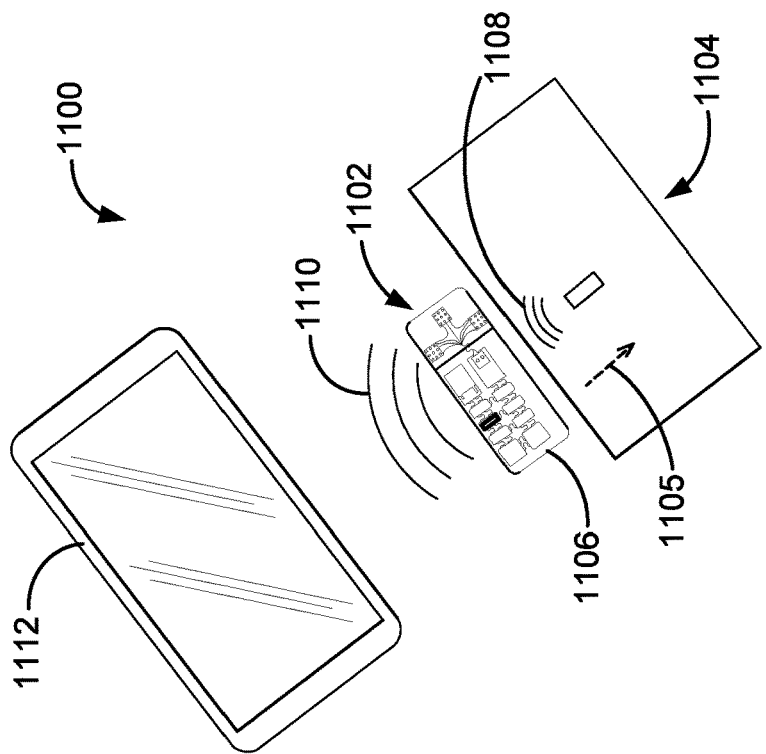
FIGS. 10A and 10B illustrate examples of conformal sensor systems with representative communication protocols in accord with aspects of the present disclosure.
Figure 10A:
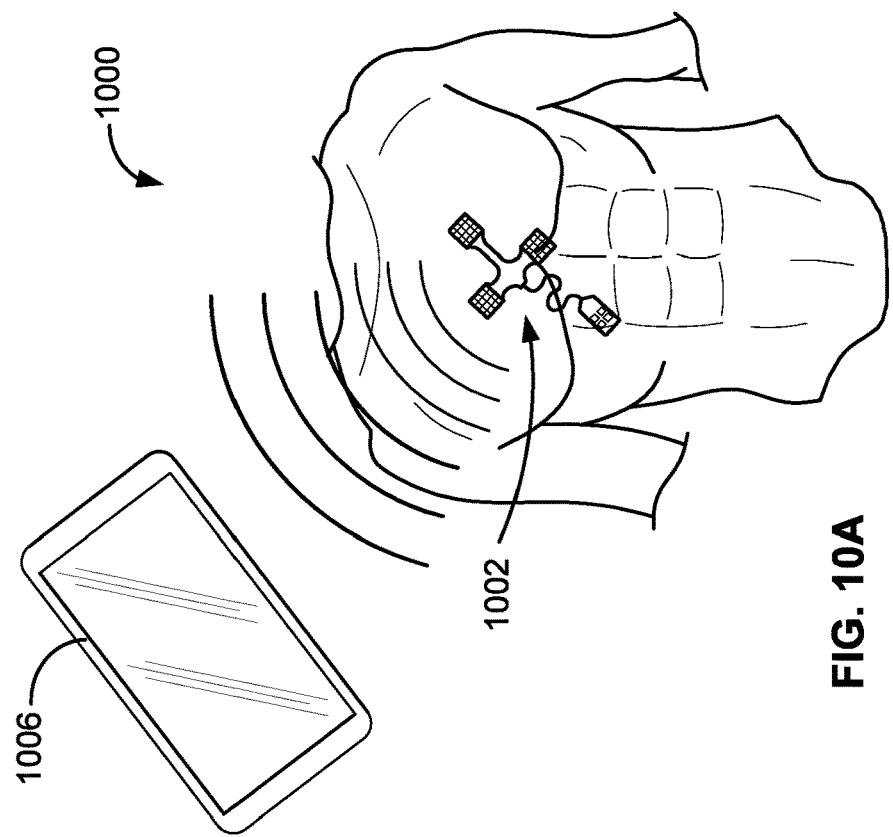

Presented in FIGS. 10A and 10B are examples of different communication protocols that can be applied to any or all of the conformal sensor devices, systems and methods described herein. In the example of FIG. 10A, a signal from a conformal cardiac sensor patch 1002 of a cardiac monitoring system 1000 can be transmitted to an external memory or other storage device, a network, and/or an off-board computing device. The signal can include an amount of data indicative of one or more measurements performed by the example conformal sensor system and/or analysis results from an analysis of the data. According to the example of FIG. 10A, the conformal sensor system 1000 uses a Bluetooth® low energy (BLTE) communications link for on-body or on-object transmission to a Bluetooth®/BLTE-enabled device 1006. In some implementations, small amounts of data are transferred at low data rates, including ECG measurements with timestamp information (or other metadata). The data transmitted may also include current peak accelerometry measurements (e.g., g value) with timestamp information (or other metadata) and/or EMG activity (either turned ON or OFF) with timestamp information (or other metadata). Non-limiting examples of the other metadata include location (e.g., using GPS), ambient air temperature, wind speed, or other environmental or weather condition. In another example accelerometer data can be used to determine values of energy over time. In other examples, data representative of physiological parameters or other measures can be transferred with timestamp or other metadata.

FIG. 10B shows another representative implementation and communication protocol where the signal is transmitted with the conformal cardiac sensor patch 1102 of the sensor system 1100 coupled to a charging platform 1104 at a designated location 1105. The conformal cardiac sensor patch 1102 is fabricated with a power transfer coil 1906 to facilitate charging with a charging coil and field 1108. Bluetooth® low energy (BLTE) communications link 1110 provides for on-body or on-object transmission to a Bluetooth®/BLTE-enabled device 1112. The signal can be transmitted to an external memory or other storage device, a network, and/or an off-board computing device. In the example of FIG. 10B, the conformal sensor system 1100 is configured to use Bluetooth® enhanced data rate (BT EDR) transmissions, at much higher data rates than BTLE, to transmit the data signal. For example, the data signal can include ECG data with timestamp information and/or other metadata. Data signals may include raw accelerometery data (X, Y, Z) with timestamp and/or EMG filtered waveform data with timestamp information. In an example, the conformal cardiac sensor system can be maintain disposed on or otherwise coupled to a charging platform while performing the BT EDR transmissions, based on the high power requirements.

Following are non-limiting example implementations of conformal cardiac sensor systems, methods and devices described herein. The example conformal sensor system can be configured to include at least one sensor component for performing the type of measurements described, including at least one conformal sensor component for measuring cardiac activity. The example conformal sensor system can be configured to include at least one sensor component for performing at least one other measurements, including measurements of motion and/or muscle activity, or other physiological measures of the body. The example conformal sensor system can include any other component described hereinabove, including at least one of a battery, a microcontroller, a microprocessor, a memory, wireless communication, active circuitry and passive circuitry. The example systems, methods and apparatus described herein can be implemented in various example implementations based on use of conformal cardiac sensors for detection and/or analysis of cardiac activity.

In any example implementation, a system, a method, or an apparatus can be configured to receive data indicative of a measurement of the conformal cardiac sensor, analyzing the data to provide information indicative of the desired result, and store to a memory and/or transmit the data and/or the information. The desired result can be information indicative of cardiac activity according to the principles of any of the examples described herein. In some examples according to the principles described herein, a procedure may involve at least a portion of the data gathered, or information related to analysis of the data, being provided to a third party, i.e., to any person or entity other than the subject wearing the sensor system. In these examples, the example cardiac sensor system may be configured to provide the data gathered, or information related to analysis of the data, to the third party only with the prior consent of the subject. Non-limiting examples of third parties include a coach, a member of a coaching staff, a physical therapist, a medical practitioner (including a doctor or other sports medicine practitioner), a physical trainer, a sports health practitioner, and the liked.

FIGS. 11-20 show non-limiting examples of implementations for any of the conformal cardiac sensor systems, methods and devices disclosed herein. Turning to FIG. 11A, for example, a conformal cardiac sensor system is configured to track the degree of fatigue and/or readiness of a subject. In this example, the conformal cardiac sensor system can be used to measure heart rate variability (HRV). HRV may be obtained by comparing different measures of heart rate and determining the range of change in values (e.g., as percentages or delta values). Any of the disclosed conformal cardiac sensor devices/systems can be placed on a portion of a subject, such as on a subject's upper back or front torso. In an example, the conformal cardiac sensor system can be implemented to collect measurements of heart rates during times of activity and during times of inactivity. For example, as shown in FIG. 11A, the conformal cardiac sensor system may include components for performing measurements of resting, active and current heart rate and movement/acceleration (activity). As shown in FIG. 11A, the cardiac sensor system may be used to determine the activity status of the subject (e.g., at rest, low-level activity, moderate-level activity, high-level activity, etc.), the HRV of the subject, and/or classify the state of readiness of the subject, e.g., fatigued, ready for low-level activity, ready for moderate-level activity, ready for high-level activity, full readiness, etc., or in any other applicable classification. For example, ECG data may be used to provide an indication of heart rate, and accelerometer data may be used to provide an indication of activity level. In an example, the conformal cardiac sensor system can include a processing unit to execute processor-executable instructions for comparing data indicative of the heart rates during times of activity with data indicative of the heart rates collected during times of inactivity, or any other analysis described herein. The processing unit may be used to execute processor-executable instructions, including instructions stored in a memory, for analysis of the comparison data. Measurements of the example conformal cardiac sensor system can be used to indicate the degree of fatigue or readiness of the subject. For example, if the comparison data indicates a low HRV, the analysis results may be used to indicate that the subject is in a state of fatigue; if the comparison data indicates a high HRV, the analysis results may be used to indicate that the subject is in a state of readiness.

Figure 11A:
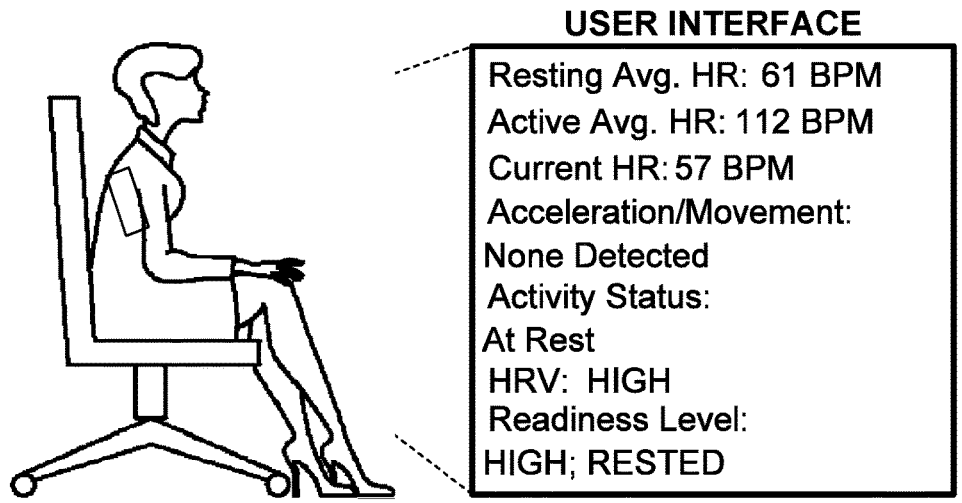
FIGS. 11A and 11B illustrate examples of conformal sensor systems with representative graphical user interfaces in accord with aspects of the present disclosure.

As shown in FIG. 11A, a conformal cardiac sensor device can be intimately coupled to the subject's torso, proximate to cardiac tissue. The example conformal cardiac sensor system can be coupled to a display (such as a video graphical user interface (GUI)) to show output indications of data collected and/or analysis results. For example, as shown in FIG. 11A, a user interface of the cardiac sensor system may be used to display an indication of the data gathered, the activity status of the subject, the HRV of the subject, and/or the readiness level classification of the subject. As a non-limiting example, the results of FIG. 11A may be used by a user preparing for a specific event or activity, such as but not limited to an athletic event. For example, the example cardiac sensor system may be used by, e.g., a coach, a physical therapist, a medical practitioner, including a sports medicine practitioner), a physical trainer, a sports health practitioner, and/or a subject (including a professional athlete, an amateur athlete, a hobbyist or other person about to engage in an activity.

Figure 11B:
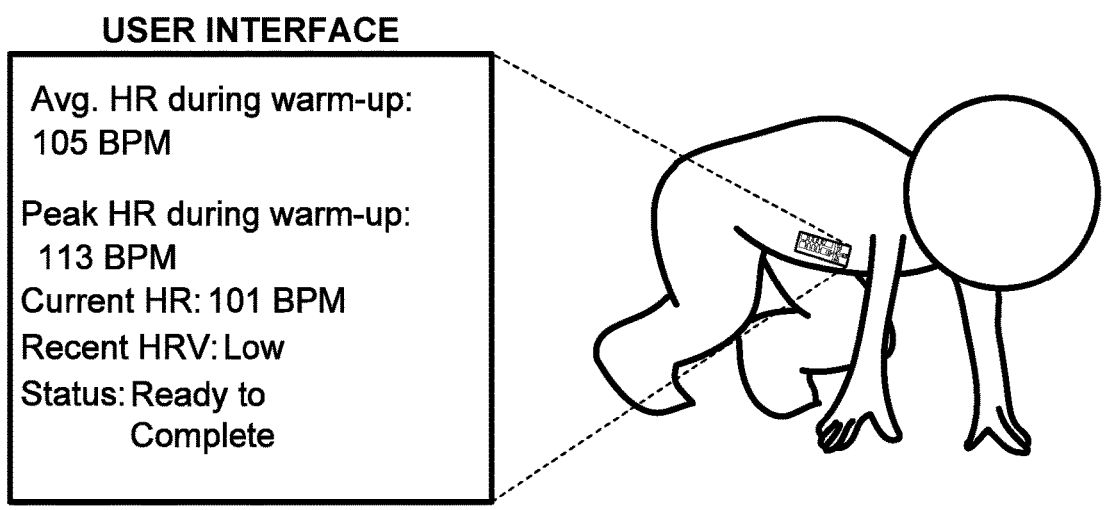

In the non-limiting example of FIG. 11B, the subject is shown to be a sprinter at the starting blocks before the start of a race or other athletic event. As shown in FIG. 11B, a user interface or other display of the cardiac sensor system (e.g., of FIG. 11A) may be consulted to provide HRV data or other analysis (or readiness classification) to determine the subject's readiness for the event. For example, the cardiac sensor system may be configured to compare HRV values for maximum heart rate recorded during warm-ups to heart rate measured immediately prior to the event. If the comparison shows a difference that is larger than a certain percentage range, then this may indicate that the subject's heart rate has slowed too much prior to the event. For example, it may be preferable that a sprinter's heart rate is kept high between warm-up and start of the athletic event. For example, maintaining a higher heart rate can ensure rapid transport of blood throughout the body during the event.

Figure 12A:
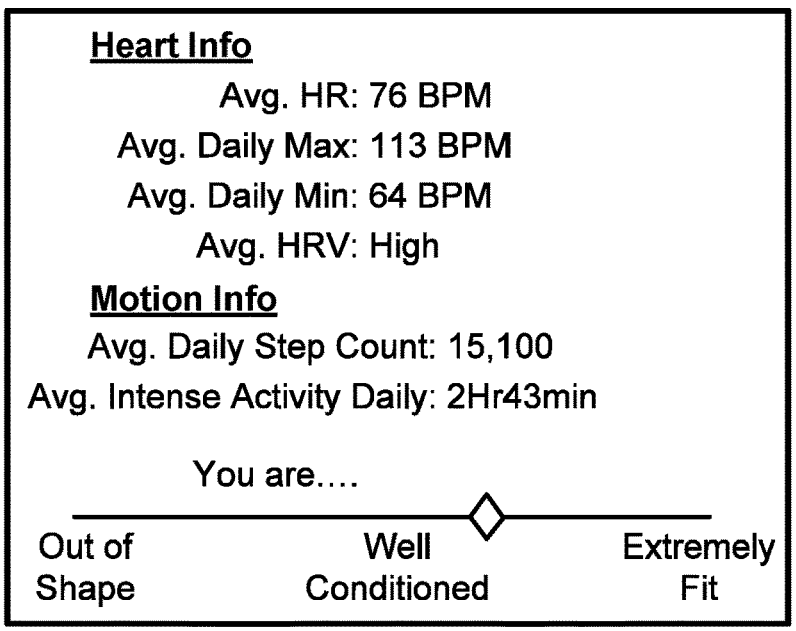
FIG. 12A illustrates a representative conformal cardiac sensor system configured for tracking a subject's overall fitness in accord with aspects of the present disclosure.

FIG. 12A shows another representative conformal cardiac sensor system, method, or device that is configured to track the overall fitness of a subject and, optionally, output an indication thereof (e.g., via feedback component 109 of FIG. 1B). For example, the subject's fitness may be indicated by a measure of conditioning and/or endurance. In this instance, a conformal cardiac sensor system/device can be used to measure heart rate variability (HRV) and/or motion (as indicator of activity). The example conformal cardiac sensor system can be placed on a portion of a subject, such as a portion of the torso or other body part. In an example, a conformal cardiac sensor can be implemented to collect measurements of heart rates during times of activity and during times of inactivity, such as described above-in connection with FIG. 11A. As shown in FIG. 12A, the cardiac sensor system may be used to determine the activity level of the subject (e.g., daily step count, or activity level (low, moderate, high), the heart rate (e.g., daily maximum, minimum or average), and/or HRV of the subject. The result of the analysis can be a classification of the physical fitness of the subject. For example, as shown in FIG. 12A, the cardiac sensor system may provide an indication of classification of the subject as out of shape (poor physical fitness), well-conditioned, or extremely fit, or in any other applicable classification. For example, ECG data may be used to provide an indication of heart rate, and accelerometer data may be used to provide an indication of activity level, including step count. In an example, the conformal cardiac sensor system can include a processing unit to execute processor-executable instructions, e.g., for comparing data indicative of the heart rates during times of activity with data indicative of the heart rates collected during times of inactivity, for determining the averaged heart rates and/or average activity frequency, average HRV, average step count, or any other analysis described herein. The processing unit may be used to execute processor-executable instructions, including instructions stored in a memory, for analysis of the comparison data. FIG. 12A shows an example user interface, which can be implemented an electronic video display device, of the data gathered and/or the results of the analysis described herein.

Figure 12B:
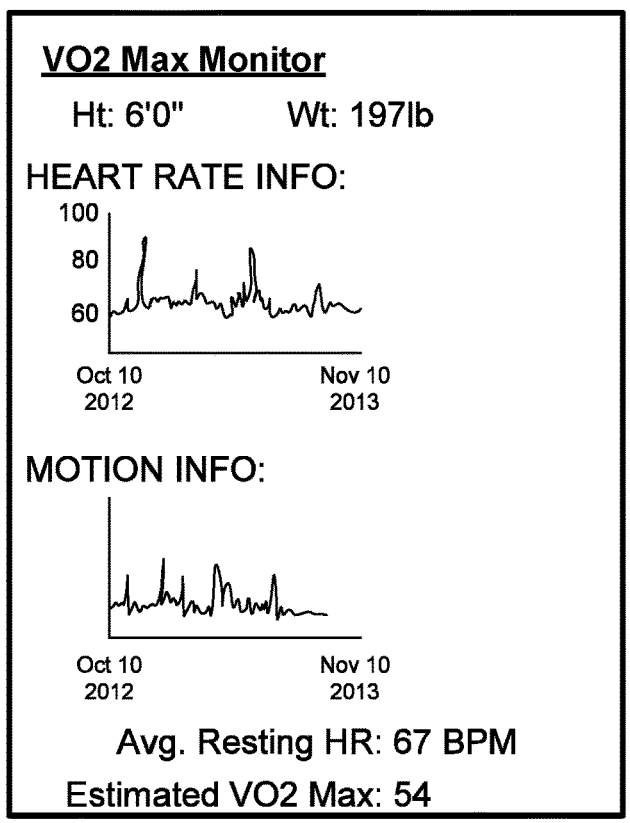
FIG. 12B illustrates a representative conformal cardiac sensor system configured to estimate a subject's VO2 max in accord with aspects of the present disclosure.

FIG. 12B shows an example a conformal cardiac sensor system operable to determine an estimate of a subject's VO2 max (also referred to as maximal oxygen consumption, maximal oxygen uptake, peak oxygen uptake, or maximal aerobic capacity) and, optionally, output an indication thereof (e.g., via feedback component 109 of FIG. 1B). For example, the cardiac sensor system can be configured to determine values for VO2 max based on the cardiac sensor measurements. The VO2 max provides an indication of the maximum capacity of a subject's body to transport and use oxygen during incremental exercise, and can be used as a measure of the physical fitness of the subject. For example, ECG data may be used to provide an indication of heart rate, and accelerometer data may be used to provide an indication of activity level. At least one processing unit of the example the conformal cardiac sensor system can be configured to execute processor-executable instructions, including instructions stored in a memory, for determining the VO2 max, or for any other analysis of the data. FIG. 12B shows an example graphical interface for displaying data gathered using a conformal cardiac sensor, the VO2 max, and/or any other information from the analysis. In this non-limiting example, the data or other information is displayed as a graphical plot.

Figure 13:
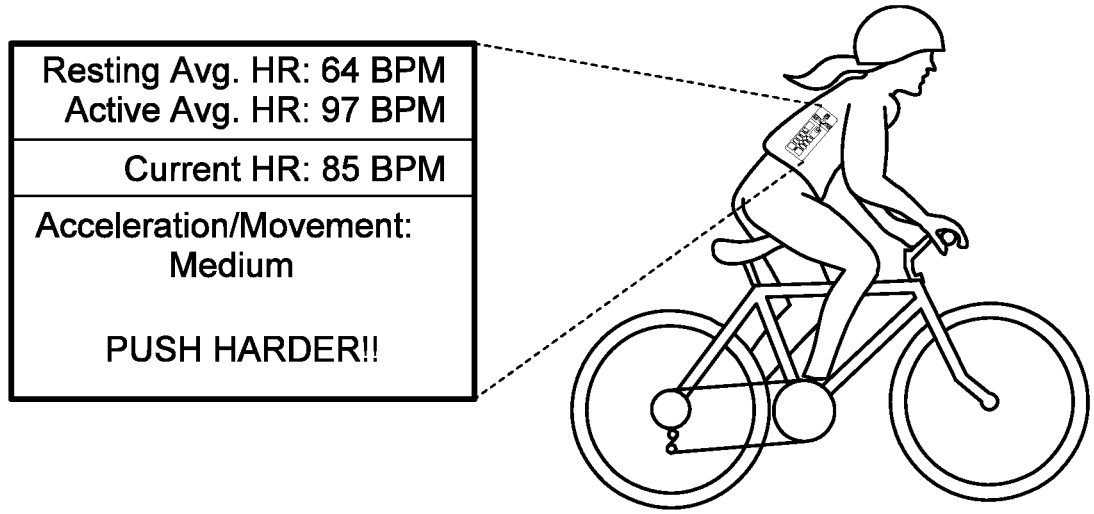
FIG. 13 illustrates a representative conformal cardiac sensor system configured to estimate a subject's cardiovascular demand in accord with aspects of the present disclosure.

FIG. 13 shows yet anther example of a conformal cardiac sensor systems that is designed to determine an estimate of cardiovascular demand for an activity/subject and, optionally, output an indication thereof (e.g., via feedback component 109 of FIG. 1B). The cardiac sensor system may be configured to measure heart rate and motion data. The cardiac sensor system may be configured to analyze the data to determine a baseline for cardiovascular fitness of the subject. For example, data analysis information can indicate a subject's cardiovascular capabilities, or degree of exertion or intensity. For example, FIG. 13 illustrates a user interface or other display device of a conformal cardiac sensor system that is operable to indicate analysis information related to resting average heart rate, active average heart rate, current heart rate, and/or indications of activity level (movement). As also shown in FIG. 13, the example conformal cardiac sensor system can provide a recommendation of change in activity level to a subject or a third party. For example, during activity, the cardiac sensor system may be used to instruct a subject to decrease a level of activity, or to maintain or increase intensity of activity based upon their cardiovascular fitness level. The cardiac sensor system may be configured to analyze the data to determine to adjust the baseline of cardiovascular fitness for the subject based on performance.

Figure 14:
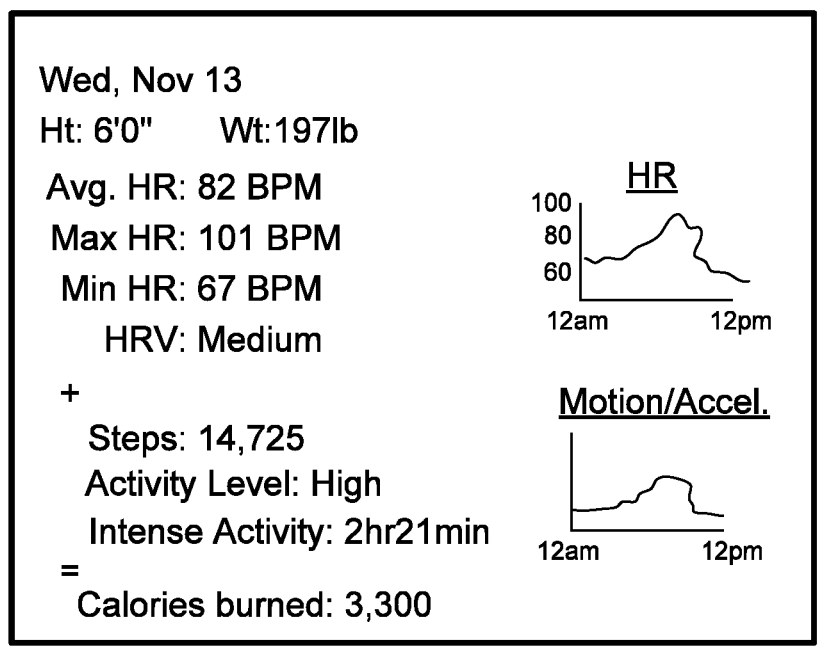
FIG. 14 illustrates a representative conformal cardiac sensor system for providing an indication of a subject's energy expenditure in accord with aspects of the present disclosure.

Turning next to FIG. 14, there is show an example of a conformal cardiac sensor system operable to assess and provide an indication of energy expenditure (e.g., via feedback component 109 of FIG. 1B). The cardiac sensor system is configured to measure heart rate and/or motion data. The cardiac sensor system then analyzes the data to determine an indication of energy expenditure of the subject. For example, the analysis may include determining an aggregate dataset of heart rate, heart rate variability, and motion data to provide a more comprehensive caloric computation (e.g., calories burned). Results of such analysis can provide a more accurate indication of energy expenditure than devices that account for only one of these metrics. As shown in FIG. 14, a user interface or other display of the conformal cardiac sensor system is used to indicate analysis information related to resting average heart rate, maximum and minimum heart rate, HRV, number of steps, and/or indication of activity level (movement).

Figure 15:
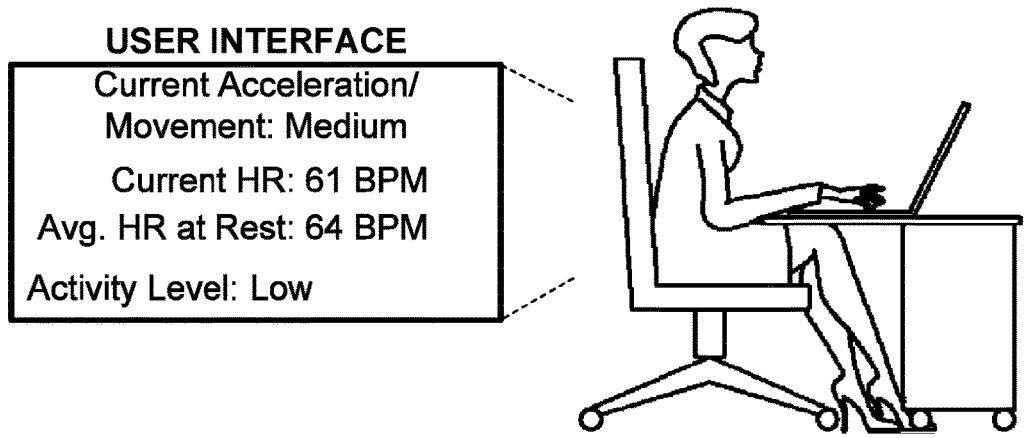
FIG. 15 illustrates a representative conformal cardiac sensor system configured to provide an indication of a subject's activity level in accord with aspects of the present disclosure.

Presented in FIG. 15 is an example of a conformal cardiac sensor system configured to assess and provide an indication of activity level (e.g., via feedback component 109 of FIG. 1B). The cardiac sensor system is configured to analyze the cardiac and motion data to determine an indication of activity level of the subject. For example, the analysis may include determining an aggregate dataset of heart rate, heart rate variability and motion data to provide a more comprehensive indication of activity level. The results of this analysis can provide a more accurate indication of activity level than devices that account for only one of these metrics. Shown in FIG. 15 is a user interface or other display device of a conformal cardiac sensor system that is used to indicate analysis information related to average heart rate, current heart rate, and/or indication of activity level (movement). In the example of FIG. 15, the subject is engaging in low-level activity, i.e., writing or typing quickly while the rest of his/her body is at rest. In this example, the conformal cardiac sensor system is configured to record measurements of the subject's movement in conjunction with heart rate (which is relatively low in this example). Based on the analysis of data indicative of these measurements, the system determines that the user is inactive. The user interface or other display can be used to alert the subject of the level of inactivity. In a medical context, the alert may indicate to the user a level of activity to be reached in order to meet, e.g., a medical prescribed level of activity.

Figure 16:
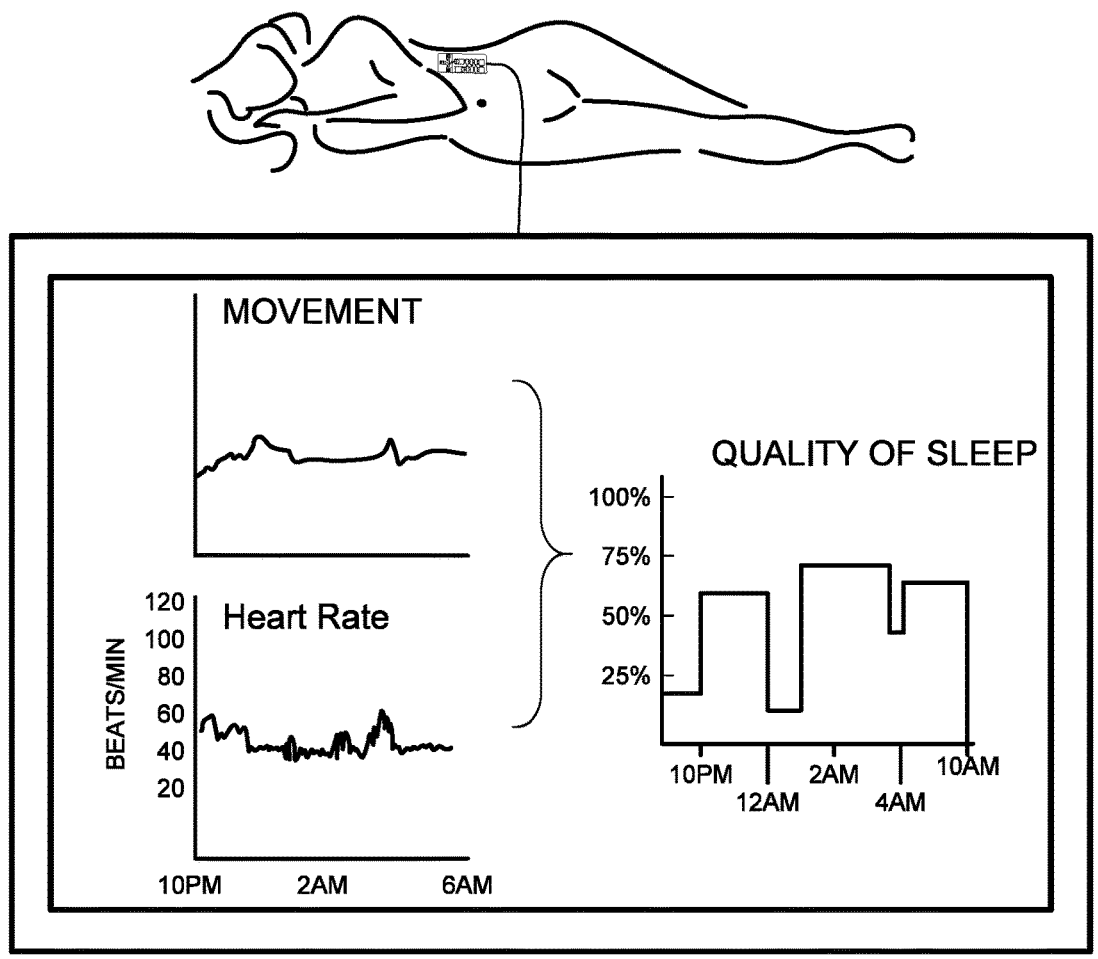
FIG. 16 illustrates a representative conformal cardiac sensor system for providing an indication of a subject's quality of sleep in accord with aspects of the present disclosure.

FIG. 16 is illustrative of a representative conformal cardiac sensor systems operable to assess and provide an indication of a subject's quality of sleep (e.g., via feedback component 109 of FIG. 1B). The cardiac sensor system in this example is configured to analyze measurement data indicative of heart rate and/or movement to determine the indication of quality of sleep. For example, the analysis may include determining an aggregate dataset of heart rate, heart rate variability, and motion data to report a more comprehensive indication of sleep quality. Analysis results help to provide a more accurate indication of activity level than devices that account for only a single metric. For example, the system may be configured to compare data indicative of two or more metrics to determine when the subject is simply moving in their sleep and not interrupting rapid eye movement (REM) sleep, or when the subject's movement is actually interrupting REM sleep. Interrupted REM sleep may hamper the quality of the subject sleep. Similar to those shown in FIGS. 11-15, the system of FIG. 16 includes a graphical user interface or other display device to provide a graphical representation of heart rate, movement, and/or a comprehensive indication of the quality of sleep.

Figure 17:
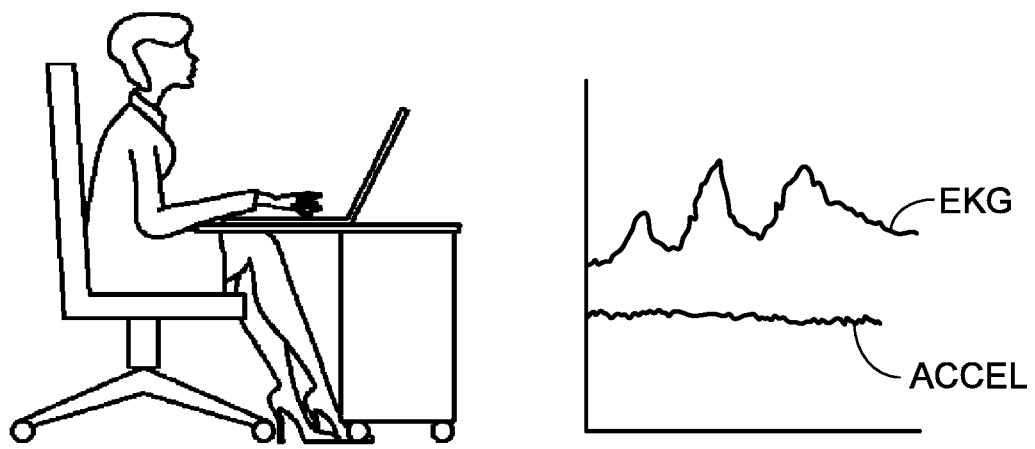
FIG. 17 illustrates a representative conformal cardiac sensor system for providing an indication of a subject's anxiety and/or stress in accord with aspects of the present disclosure.

Looking next at FIG. 17, there is shown a conformal cardiac sensor system that is configured to assess and provide an indication of anxiety and/or stress of a test subject (e.g., via feedback component 109 of FIG. 1B). The cardiac sensor system is configured to analyze measurement data indicative of heart rate (including ECG data) and/or movement to determine the indication of anxiety and/or stress. For example, the analysis may include determining an aggregate dataset of heart rate, heart rate variability and motion data, an aggregate dataset of heart rate, heart rate variability and motion data to determine anxiety rates and/or stress. By way of non-limiting example, heart beats associated with anxiety or stress traits can be characterized by anatomizing periods of inactivity (as indicated by accelerometer data) that are associated with a rise in heart rate above a certain amount or percentage (as indicated by heart rate data) and evaluating the quality of that heart beat. As depicted in FIG. 17, a widely varying heart rate (here, represented by ECG data) as compared to low-varying movement (here, represented by accelerometer data). Such analysis result may provide a more accurate indication of anxiety and/or stress.

Figure 18:
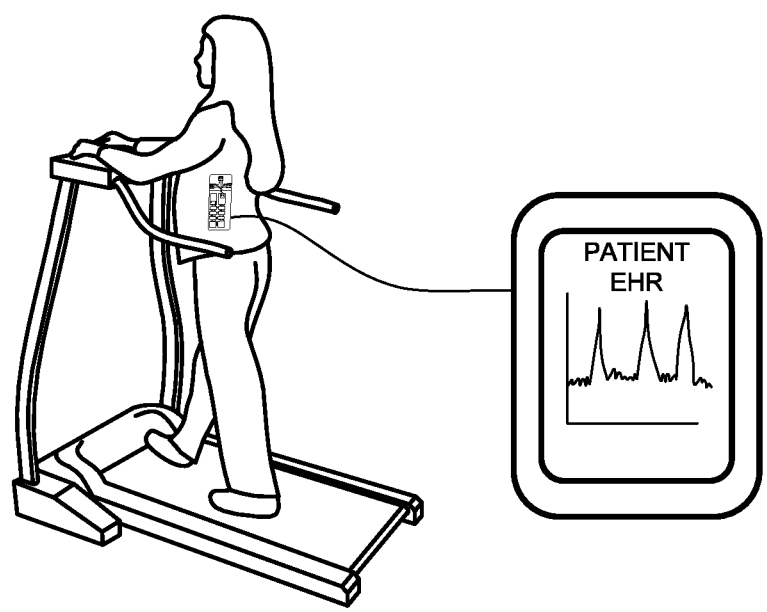
FIG. 18 illustrates a representative conformal cardiac sensor system configured to provide an indication of a subject's heart plasticity and/or abnormality in accord with aspects of the present disclosure.

FIG. 18 shows an example of a conformal cardiac sensor system operable to provide an indication of heart plasticity and/or heart abnormality and, optionally, outputting an indication thereof (e.g., via feedback component 109 of FIG. 1B). The cardiac sensor system may be configured to analyze the heart rate data to determine the indication of heart plasticity and/or abnormality of the subject. For example, the analysis may include detecting arrhythmia, tachycardia, fibrillation and/or bradycardia during controlled testing conditions and/or environments. If the subject's activity is controlled, the data gathered can be analyzed to discern the impact of the activity on the sinus arrhythmia and the physical impact to the heart. As shown in FIG. 18, a graphical user interface or other electronic display device of the conformal cardiac sensor system is used in conjunction with the sensor unit to monitor and display the subject's performance and/or heart rate data remotely. In an example, the data gathered may be provided to a third party, e.g., a health or medical practitioner or provider. The conformal cardiac sensor system may include remote sensing capabilities, such that a third party is able to remotely monitor the subject's performance and/or heart rate data. For example, the data or analysis information may be sent to the subject's electronic health record(s).

Figure 19:
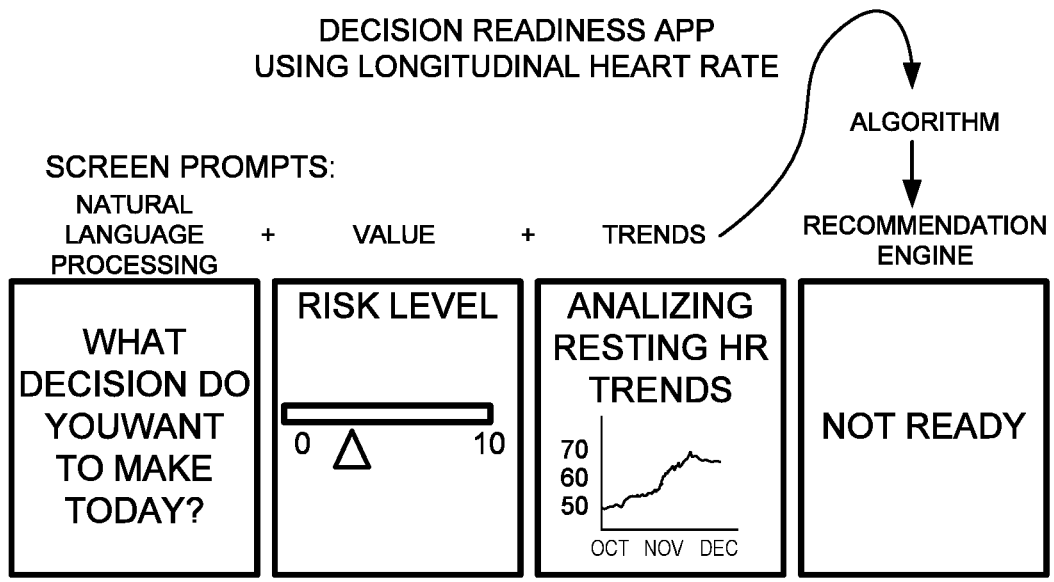
FIG. 19 illustrates a representative conformal cardiac sensor system configured to provide heart rate monitoring in accord with aspects of the present disclosure.

FIG. 19 shows yet another representative conformal cardiac sensor system that is configured to provide heart rate monitoring and, optionally, outputting an indication thereof (e.g., via feedback component 109 of FIG. 1B). According to this implementation, information related to the heart rate monitoring is used to inform the timing and/or improve the quality of a subject's decision making capability based on an analysis of the subject's condition. For example, a subject's decision making capability may be impaired if the subject is under stress and/or anxiety. The cardiac sensor system may be configured to analyze heart rate data and/or accelerometer data to provide heart rate monitoring. For example, analysis of the heart rate and/or accelerometer data is used to provide the subject or a third party with an indication of, e.g., time periods when the subject is under abnormal circumstances causing stress and/or anxiety. In an example, the cardiac sensor system is configured to provide an indication to a user to execute or withhold decision making at points of high levels of stress and/or anxiety (e.g., exceed predetermined threshold level), as indicated by the data analysis. For example, the subject may be a businessperson making a decision of great magnitude for his/her organization. Based on an analysis of the subject's levels of stress and/or anxiety, the subject may determine that the decision making should be performed in isolation from the potential stressors (including any external stressors). FIG. 19 shows examples of screen prompts on a graphical user interface (or other electronic display device) of a conformal cardiac sensor system in a decision readiness application. The system may include an example recommendation engine. The recommendation engine may perform an algorithm (and associated methods), using the gathered data and/or analysis information, to provide the indication of decision making readiness. The example recommendation engine may be configured to indicate whether a user is ready or not ready to make a decision, based on the data analysis. The system may be configured to use a series of inputs, including user input text or other data, user input risk value, and longitudinal heart rate trends, to provide the indication of the quality of the subject's decision making capability. As depicted in the example of FIG. 19, the indication may be displayed as a sliding scale of risk level, an indication of readiness for decision making, and/or an analysis of trends.

Figure 20:
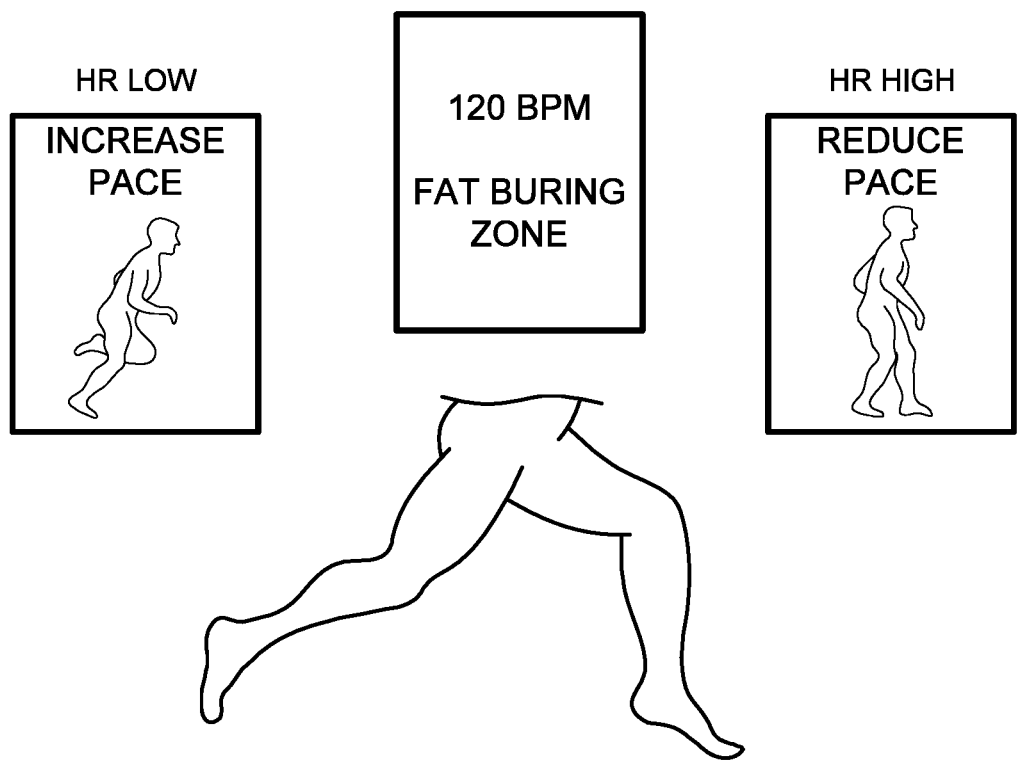
FIG. 20 illustrates a representative conformal cardiac sensor system configured to provide an indication of the effect on a subject of an activity type in accord with aspects of the present disclosure.

With reference to FIG. 20, there is shown a conformal cardiac sensor system for providing an indication of the effect of an activity type and, optionally, outputting an indication thereof (e.g., via feedback component 109 of FIG. 1B). As a non-limiting example, information related to heart rate monitoring may be used to indicate if the activity is serving as an aerobic exercise type or an anaerobic exercise type. For example, during physical exertion, the cardiac sensor system may be configured to determine whether the subject's fat reserves or glucose reserves are being utilized (an indication of whether or not the Krebs Cycle is activated). The physical exertion may be associated with exercise and/or general activity. Non-limiting examples of the physical exertion include running and/or walking on a treadmill, or biking on a stationary bike. FIG. 20 shows examples of screens on a user interface (or other display) of the conformal cardiac sensor system, that provide information during exercise based on the user's goal in weight loss. For example, based on measurements of heart rate data, the user interface (or other display) may provide recommendations for the user to maintain a certain heart rate to stay in a fat burning zone. As another example, based on measurements of heart rate data, the user interface (or other display), it may be determined that the heart rate is too low, and the system provides a prompt to the user to increase exercise pace. If it is determined that the heart rate is too high, the system may provide a prompt to the user to reduce exercise pace.

Figure 21:
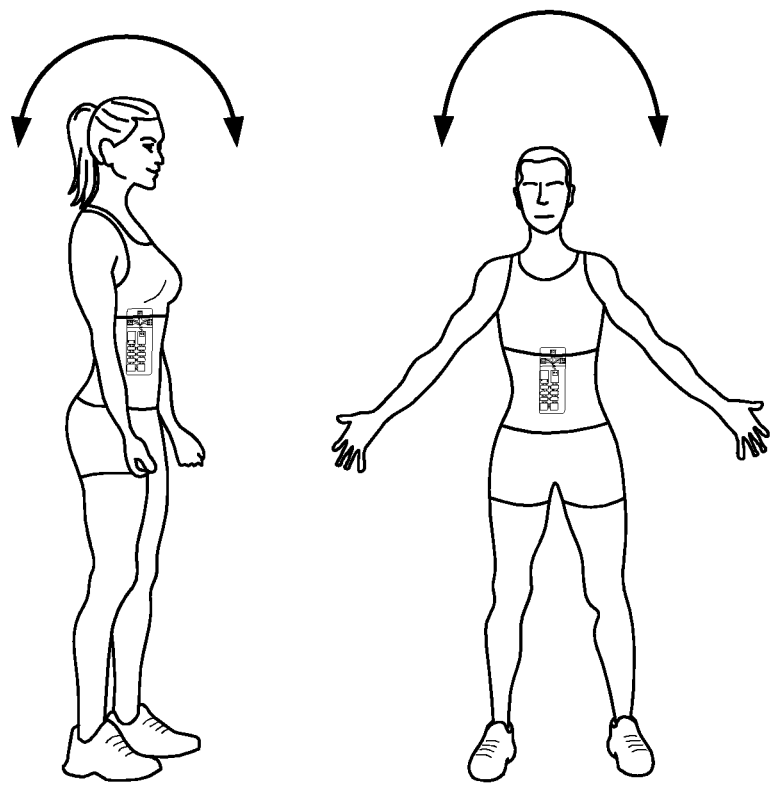
FIG. 21 shows a representative conformal cardiac sensor system for detection of a subject's fall or other rapid movement in accord with aspects of the present disclosure.

Next, FIG. 21 shows an example conformal cardiac sensor system that is operable for detection of a fall or other rapid movement. The example conformal cardiac sensor system can include an ECG, an accelerometer, and a trigger. In an example implementation, the conformal cardiac sensor system can be configured to monitor a subject's condition. Once there is an indication that there may have been a fall or other rapid movement, e.g., determined based on accelerometer data, the trigger can cause the system to activate the ECG measurement component(s). Such ECG measurements can be analyzed to provide an indication of the subject's condition. In an example, the system can be configured to issue an alert (e.g., via feedback component 109 of FIG. 1B) if the ECG data indicates that the subject may have experienced an adverse effect from the all or other rapid movement. In an example, elderly care or invalid care can be improved by using a conformal cardiac sensor system that includes fall or rapid movement detection sensors in conjunction with ECG electrodes to monitor the vital signs and activities of subjects. In an example, the conformal cardiac sensor system can be configured to capture of physiological data related to the subject and/or communicate of this information to the subject or a third party. As a non-limiting example, the third party can be the subject's doctor, or caregiver, or other medical or health practitioner. In an example, the system can be configured to transmit an alert or other indication to a third party when the subject experiences the fall or rapid movement. In an example, the conformal cardiac sensor systems can be configured as a wearable patch that is substantially mechanically invisible (i.e., least cumbersome), and mounted to the subject to promote a high level of adherence. In an example, the conformal cardiac sensor system can be configured to provide data sets of a least amount of false positives or negatives.

As depicted in the example of FIG. 21, the conformal cardiac sensor system may be configured to determine the type of fall or rapid movement based on the data measurement, e.g., accelerometer data. For example, a fall can occur along either the sagittal or coronal planes. A fall along the sagittal plane can occur forward or backward, whereas falls along the coronal plane are lateral falls, i.e., to the right to left. An example conformal cardiac sensor system that includes a tri-axis accelerometer, and is disposed proximate to the chest or other portion of the torso, can be used to detect sudden falls or other rapid movement, impact and/or recovery. In an example, during a recovery phase, it can be beneficial to track the vital signs of a subject for quick assessment of the subject's status (for example, for ambulatory assessment). Non-limiting examples of the vital signs include heart rate and/or ECG.

In a non-limiting example, any of the example conformal cardiac sensor system can be maintained in sleep mode when no measurements are being made. If the accelerometer measurement indicates that a threshold or other specified value is exceeded, potentially indicating a fall event or other rapid movement, the microcontroller can be triggered to be turned "ON", along with an ECG recording sensor. In an example a communication component, such as but not limited to a Bluetooth® module, also may be triggered. The ECG measurements can be taken until either the ECG recording sensor is turned "OFF" or the power source loses energy below a threshold value (e.g., a battery runs out). The ECG measurements may be stored locally on a memory of the system age and/or communicated to an external storage (e.g., using data streaming) until the ECG recording sensor is turned "OFF" or the power source loses energy below a threshold value.

Figure 22:
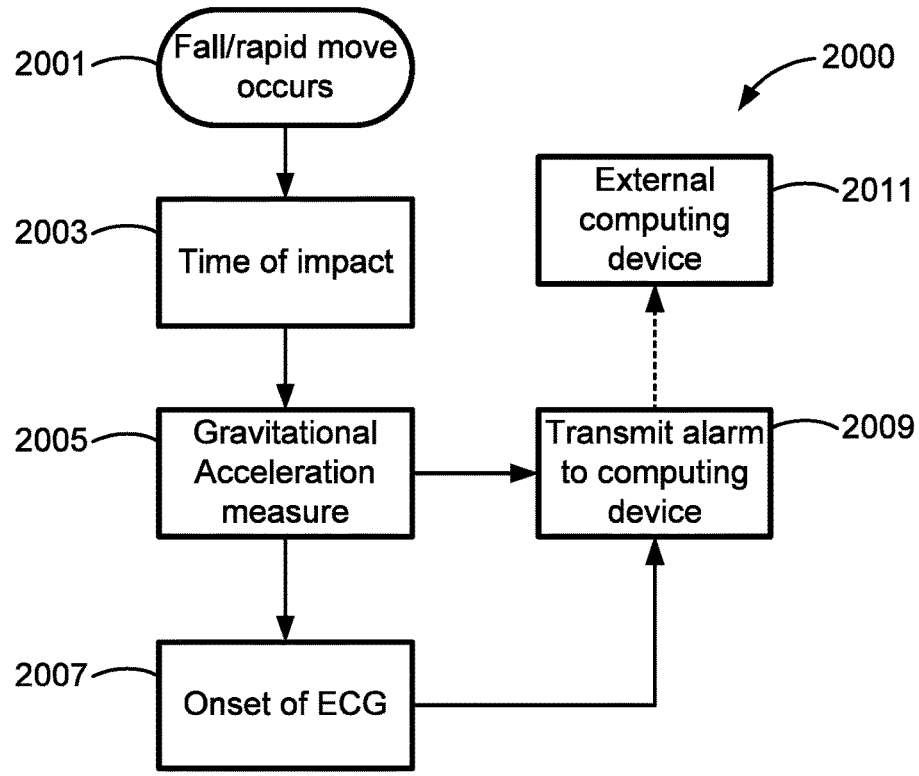
FIG. 22 is a flowchart illustrating an example of a sequence of operation of the components of an example conformal cardiac sensor system in accord with aspects of the present disclosure.

FIG. 22 is a flowchart illustrating a non-limiting example of an algorithm or sequence of operations or a method 2000 of the components of an example conformal cardiac sensor system. The method presented in FIG. 22 can be carried out, for example, by one or more or all of the conformal cardiac sensor devices, apparatuses and systems disclosed hereinabove and below. At block 2001, a fall or a rapid/uncontrolled movement occurs. Responsive to detection of a fall or other rapid/uncontrolled movement, a time of impact can be recorded at block 2003 and accelerometer measurements may be taken (gravitational measures) at block 2005. If an acceleration measurement is above a threshold, the method 2000 proceeds to block 2007 with the onset of ECG measurement recording can be initiated. Data indicative of the acceleration measure and/or the ECG measurement may be stored to a memory or transmitted to an external computing device (as depicted in FIG. 22 at block 2009). In another example, the system can be configured to transmit an alarm or other form of alert, based on the acceleration measure and/or the ECG measurement, to an external computing device, as seen at block 2011.

Figure 23:
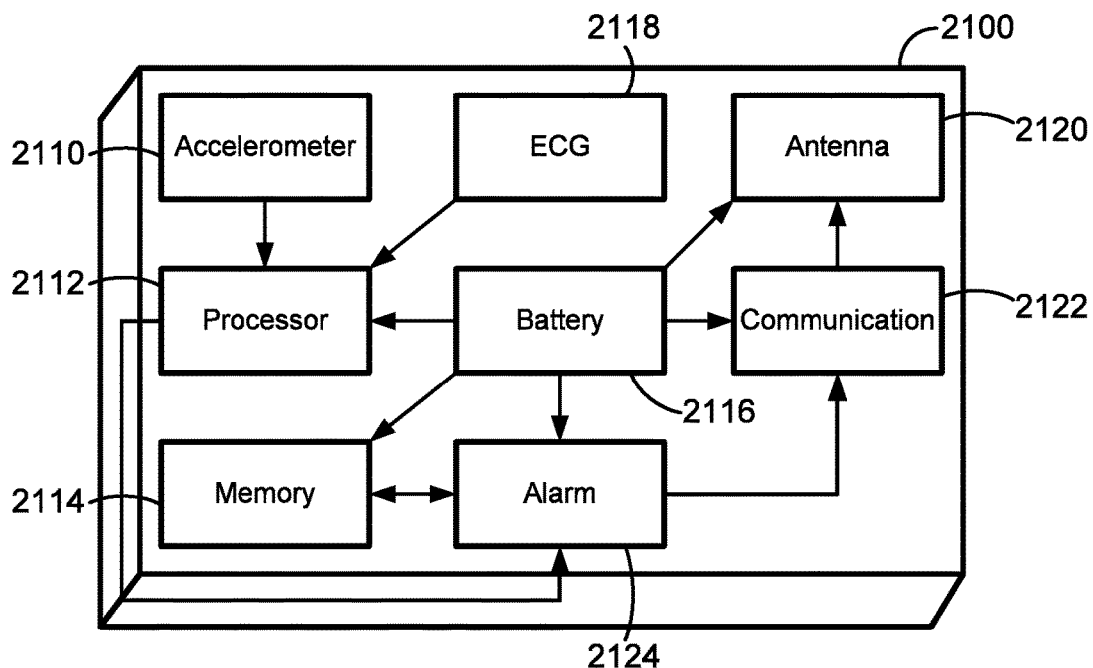
FIG. 23 is a schematic illustration of an example layout of a conformal cardiac sensor system in accord with aspects of the present disclosure.

Illustrated in FIG. 23 is an example layout of components of an example conformal cardiac sensor system 2100 that can be used to perform any of the example methods and operations and algorithms described herein. The example conformal cardiac sensor system 2100 includes an accelerometer 2110, a processor 2112, a memory 2114, a battery 2116, an ECG component 2118, an antenna 2120, a communication component 2122 and an alarm component 2124.

Figure 24:
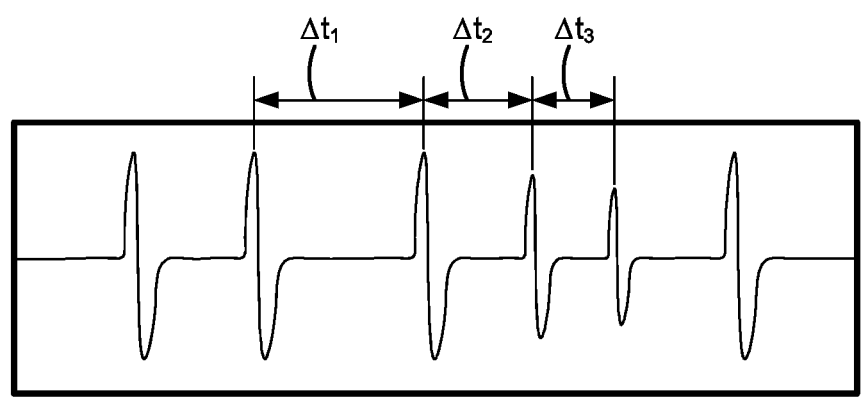
FIG. 24 is a graphical illustration showing some example measurements that can be taken using an electrocardiogram (ECG) component of an example conformal cardiac sensor system in accord with aspects of the present disclosure.

FIG. 24 shows some representative measurements that can be taken using an ECG component of an example conformal cardiac sensor system. The measurements show a wave pattern of electrical signals indicative of cardiac activity. The indicated interval ($\Delta t1$, $\Delta t2$, $\Delta t3$) can be analyzed to provide an indication of heart rate, HRV, or the information related to cardiac activity which can optionally be output to the user (e.g., via feedback component 109 of FIG. 1B).

In another example, the example conformal cardiac sensor systems can be used for monitoring heart rate variability in a subject having Parkinson's disease and, optionally, output an indication thereof (e.g., via feedback component 109 of FIG. 1B). In this example, the conformal cardiac sensor systems may be mounted to the chest or other portion of the torso of the subject. In an example, the conformal cardiac sensor system may be placed directly on the sternum. Parkinson's disease can cause dysfunction of the autonomic cardiovascular system, which can be detected based on analysis of data indicative of heart rate variability. This dysfunction can be more pronounced in subjects with more severe forms of Parkinson's disease. The example conformal cardiac sensor system can be configured to monitor the R-R variability, where the R-R is derived based on a measure of the time interval between QRS deflections in the ECG measurements. In an example, it may be determined based on the analysis results that the Parkinson's subject is experiencing abnormal movement or breathing. In the event of determination of abnormal movement or breathing, an alert or other indication may be displayed on a display of the system or communicated externally. In an example, the alert or other indication may be transmitted to an external computing device, such as but not limited to a smartphone. The example conformal cardiac sensor system can be configured such that detection of abnormal movement or breathing causes the system to in turn trigger the recording of ECG measurements.

Figure 25:
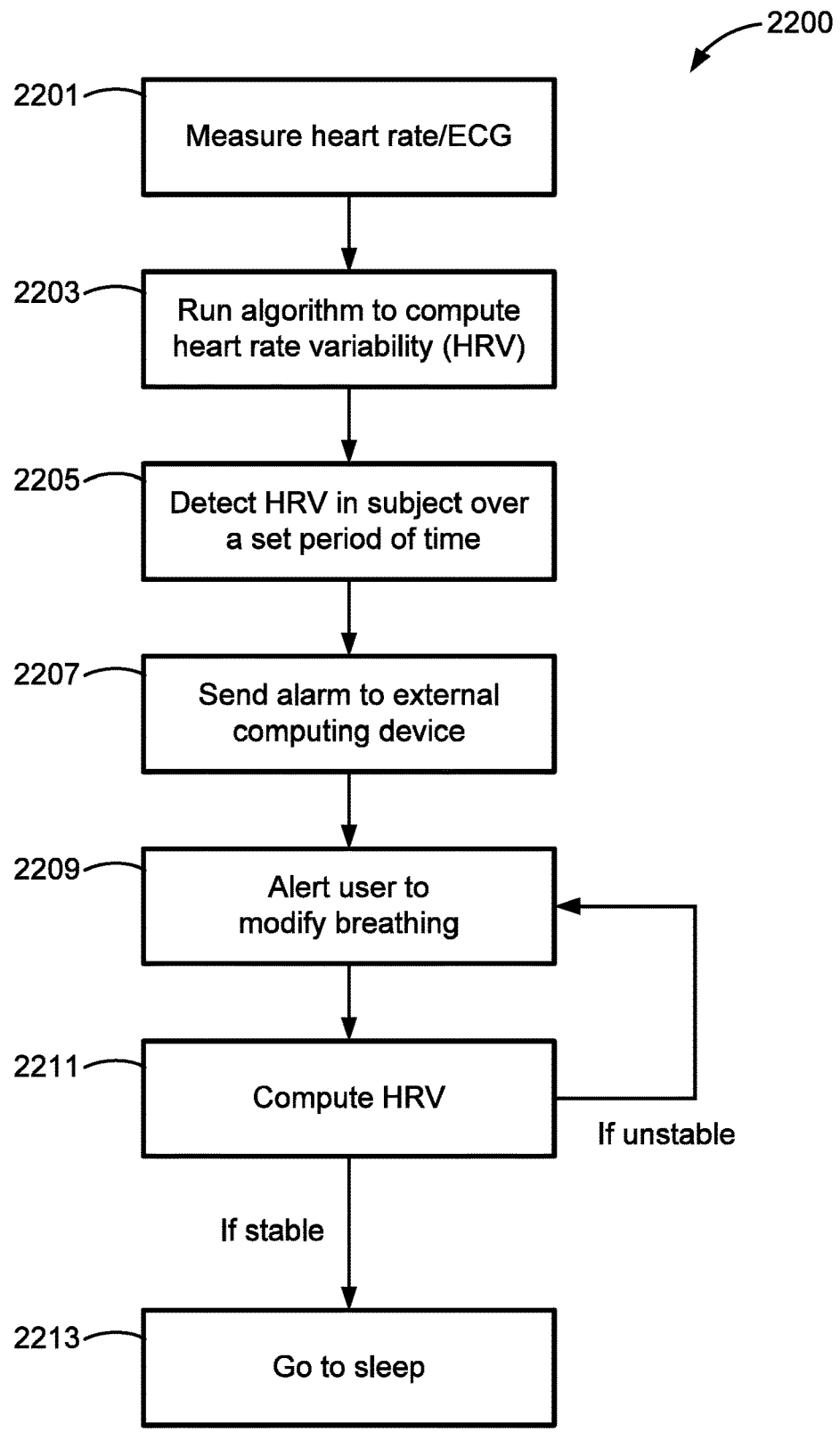
FIG. 25 is a flowchart illustrating a representative implementation of a conformal cardiac sensor system in accord with aspects of the present disclosure.

FIG. 25 is a flowchart of an example implementation or method 2200 of a conformal cardiac sensor system. The method presented in FIG. 25 can be carried out, for example, by one or more or all of the conformal cardiac sensor devices, apparatuses and systems disclosed hereinabove and below. At block 2201, heart rate/ECG measurements are taken of a subject to which the conformal cardiac sensor system is coupled. An algorithm (and associated methods) is run to compute the heart rate variability at block 2203. The measurement and determination of HRV is conducted over a set period of time, e.g., at block 2205. An alarm is sent at block 2207 to an external computing device if the data analysis indicates abnormal breathing. At block 2209, the alert is also provided to a user to modify the breathing of the subject. The HRV is computed in a feedback loop at block 2211. If the data analysis indicates that the breathing is unstable, the user is once again alerted to modify breathing and the HRV is computed once again. If the data analysis and HRV computation indicates that the breathing is stable, the conformal cardiac sensor system is allowed to return to a dormant mode (e.g., to go to a sleep mode) at block 2213. In an example, the procedure of the feedback loop may be performed with administration, e.g., of a pharmaceutical drug, biologic, or other therapy, to the subject. If the computed HRV indicates that the HRV is stable, the administration may be discontinued. In another example, no administration is performed until the system determines that the HRV is stable.

In another example, the example conformal cardiac sensor systems can be used for monitoring heart rate variability in Parkinson's disease to provide a potential alert of conditions that can lead to heart failure (e.g., via feedback component 109 of FIG. 1B). A HRV decrease in a Parkinson's disease subject can be used as an indicator of reduced motor activity. A decrease in HRV may be used as a marker of cardiovascular dysautonomia. An example conformal cardiac sensor system can be configured to perform continuous motor activity monitoring (e.g., using recorded and/or standardized motor activity monitoring) and ECG activity monitoring. The data can be analyzed to provide an indication of motor complications in tandem with electrocardiogram activity. As an example, analysis of data gathered can be used to indicate sudden changes in heart rate or lack of variability. In Parkinson's subjects, such data or analysis results can be tracked (including being stored or transmitted) during medication cycles to determine proper dosage and to reduce risks of heart failure in the Parkinson's subject.

In another example, the example conformal cardiac sensor systems can be used as a cardiac arrhythmia sensing device. In this example, the conformal cardiac sensor system may be used as a cardiac monitor for identifying suspected arrhythmias in a subject based on cardiac data gathered and, optionally, output an indication thereof (e.g., via feedback component 109 of FIG. 1B). In a difficult-to-diagnose subject, continual or longer-term monitoring of cardiac rhythm can be beneficial. The example conformal cardiac sensor system can be configured to detect the presence of atrial arrhythmias, including asymptomatic episodes, or to monitor the amount of time a subject is in atrial fibrillation (AF) to assess whether medical treatment should be administered.

In an example, a subject may be administered, e.g., a pharmaceutical drug or biologic or other therapy (e.g., via therapeutic component 108 of FIG. 1B). The example conformal cardiac sensor system can be configured to detect heart palpitations or murmur side effects induced by the substance being administered. The example conformal cardiac sensor system can be disposed on a torso or other portion of a subject, and used to capture ECG data, continually, continuously or at regular intervals, during an actual episode. Information based on the measurements may be analyzed, including any such information stored in a memory or transmitted, to determine whether the episodes are caused by abnormal rhythms, such as but not limited to a Holter counter.

In an example, the example conformal cardiac sensor system may be configured to determine an effect of regulating heart rate on BP/hypertension using continuous monitoring: a subject with pre-hypertension can be at risk of hypertension and cardiovascular diseases. Efficient interventions may not be accomplished if continuous monitoring of irregular heart rate is not well characterized. Studies indicate that heart rate variability-biofeedback (HRV-BF) increases HRV and baroreflex sensitivity (BRS), as well as reduces related pathological symptoms. Such a result suggests the potentially beneficial effects of HRV-BF on prehypertension. However, little is known about these effects. These effects can be investigated using the example conformal cardiac sensor system according to the principles herein, by configuring the system to track heart rate variability and, optionally, output an indication thereof (e.g., via feedback component 109 of FIG. 1B). The effective outcome of tracking HRV is to elucidate the mechanism of pre-hypertension, which can be strongly correlated with HRV. These effects suggest that HRV-BF, a novel behavioral neurocardiac intervention, could enhance reduce BP, by improving the cardiac autonomic tone, and facilitate BP adjustment for individuals with prehypertension.

Figure 26:
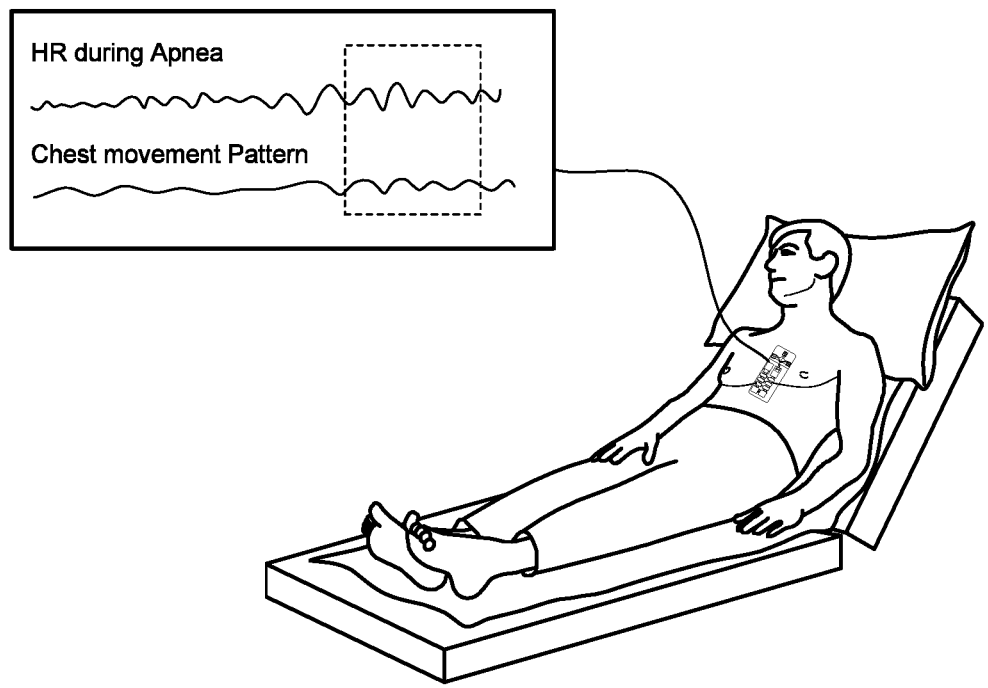
FIG. 26 shows a representative use of a conformal cardiac sensor system to track sleep disordered breathing in accord with aspects of the present disclosure The present disclosure is susceptible to various modifications and alternative forms, and some representative embodiments have been shown by way of example in the drawings and will be described in detail herein. It should be understood, however, that the inventive aspects are not limited to the particular forms illustrated in the drawings. Rather, the disclosure is to cover all modifications, equivalents, and alternatives falling within the spirit and scope of the invention as defined by the appended claims.

In the example of FIG. 26, the example conformal cardiac sensor system can be used to track sleep disordered breathing and, optionally, output an indication thereof (e.g., via feedback component 109 of FIG. 1B). When a subject with sleep-disordered breathing has a breathing disorder event, there can an autonomic arousal associated with a brief awakening. The subject may then resume normal breathing, and fall back to sleep. This repeated awakening can be associated with a repeated increase in heart rate, which returns to baseline when the subject falls back asleep. An example conformal cardiac sensor system can be configured to track these events by measuring R-R intervals, based on QRS detection algorithms (used to model the combination of three of the graphical deflections in the ECG). This measurement can be coupled with accelerometer measurements (e.g., indicating changes in chest movements) induced by breathing, can be correlated with the onset of sudden events of sleep apnea. The information obtained based on this data analysis can be used for continuous monitoring of a subject with sleep apnea during their sleep cycles. The low profile of the conformal cardiac sensor system makes it attractive for use and adherence to a portion of a subject with sleep apnea.

An example conformal cardiac sensor system can be used for determining heart rate or activity. An example conformal cardiac sensor system can include an accelerometer component and an ECG component. The system may also include optical sensor components and/or ECG components, e.g., where the system is disposed proximate to the chest, to provide measures for use in the analysis In an example implementation, the conformal cardiac sensor system can be configured to determine a subject's heart rate variability based on the sensor measured data values and output an indication thereof (e.g., via feedback component 109 of FIG. 1B). The information representative of heart rate variability can be used as an indicator of subject fatigue or readiness.

An example conformal cardiac sensor system herein can be used to determine an individual's overall cardiac readiness and output an indication thereof (e.g., via feedback component 109 of FIG. 1B). For example, a determination of high variability of an individual's cardiac readiness can be used as an indication that the subject is in good or better physical fitness than an average individual; a determination of low variability can be taken as an indication that the individual is at a worse physical fitness level than an average individual.

In an example implementation, the conformal cardiac sensor system can be configured to detect a pattern of cardiac activity (including heart rate) that is indicative of a specific cardiac event. For example, the conformal cardiac sensor system can be configured to determine the occurrence of the specific event by comparing cardiac sensor measurements of a patient to a standard for the cardiac event. The standard can be a simulated signal curve or a composite signal based on prior recorded measurement at previous incidents of the specific event, e.g., recordings from the same subject and/or other subject experiencing the specific event.

In an example implementation, the conformal cardiac sensor system can be configured to measure heart rate variability and analyze the data to provide an indicator (e.g., via feedback component 109 of FIG. 1B) of overall physical fitness of a subject for specific type of conditioning, such as endurance for a physical activity. An optical sensor component or ECG component of the system can be used to provide additional data measures for use in the analysis. In this example, the cardiac sensor may be configured to pattern match to each individual subject's condition, such that deviations from a set of measurement profiles can be used as indicators of loss of desired physical conditioning.

For example, the cardiac sensor can be configured to determine a baseline for a subject's heart rate variability as a point of comparison to alert a users (including a subject, or a third party with consent, such as a coach or medical practitioner) if the subject's measurements deviate from an desired range of norms. For example, the cardiac sensor can be configured to determine values for VO2 max (also referred to as maximal oxygen consumption, maximal oxygen uptake, peak oxygen uptake or maximal aerobic capacity), based on the cardiac sensor measurements. The VO2 max provides an indication of the maximum capacity of a subject's body to transport and use oxygen during incremental exercise, and can be used as a measure of the physical fitness of the subject.

In an example implementation, the conformal cardiac sensor system can be configured to measure heart rate, coupled with measures of motion, analyze the results, and provide an indicator of exertion and/or intensity of a subject (e.g., via feedback component 109 of FIG. 1B). For example, the analysis can be used to provide an indicator of a subject body's cardiovascular demands and capabilities.

In an example implementation, the conformal cardiac sensor system can be configured to measure heart rate, coupled with measures of motion, and provide an indicator of the subject's energy expenditure (e.g., via feedback component 109 of FIG. 1B), resulting in a more accurate calorie computation as a result of more robust data sets. In an example, the sensor can be configured to combine measures of heart rates, hear rate variability and accelerometry.

In an example implementation, the conformal cardiac sensor system can be configured to measure heart rate, coupled with measures of motion, to provide an indicator of a subject's activity level (e.g., via feedback component 109 of FIG. 1B). For example, through analysis of sensor measurement data, the subject's precise level of activity can be estimated. For example, if a user's measured value of acceleration is intense and the measured values for heart rate are not increasing, it may be determined that the user is almost complete rest but also engaging in very low-exertion activity, e.g., writing, or typing.

In an example implementation, the conformal cardiac sensor system can be configured to measure heart rate, coupled with measures of motion, to provide an indicator of a subject's quality of sleep (e.g., via feedback component 109 of FIG. 1B). For example, comparisons of accelerometer measurement data and heart rate measurement data can be used to determine if a subject is simply moving during the night without interruption of REM sleep or actually experiencing interruption of REM sleep, and as a result losing quality of rest and/or sleep.

In an example implementation, the conformal cardiac sensor system can be configured to measure heart rate, and based on analysis of the results, provide an indication of subject level of anxiety (e.g., via feedback component 109 of FIG. 1B). For example, the system can be configured to cross-reference heart rate data with data from the accelerometer to determine whether there is a significant variation in a subject's activity, and whether there is a significant increase in heart rate. Based on this analysis, the system can determine the quality of the subject's heart beat, to detect heart beat consistent with indication of changing levels of anxiety. The data may also be analyzed to determine heart rate for an indicator of stress.

In an example implementation, the conformal cardiac sensor system can be configured to measure heart rate and use an analysis of the results for detection of heart plasticity and abnormalities, including arrhythmia, tachycardia, fibrillation, and bradycardia. Feedback can be provided to a user (e.g., via feedback component 109 of FIG. 1B) regarding such conditions. An optical sensor component or ECG component of the system can be used to provide additional data measures for use in the analysis. The example system can be implemented under controlled scenarios, since some uncontrolled events may impact heart rate and potentially cause the analysis to indicate the uncontrolled event rather than the abnormality condition. For example, the user's activity may have an impact of sinus arrhythmia, or a physical impact to the heart.

In an example implementation, the conformal cardiac sensor system can be configured to measure heart rate and provide information that can assist in decision making regarding the timing of heart activity and/or quality of heart function. For example, analysis of heart rate and accelerometry measurement data may be used to provide a user with an indication of periods of time that the user (or user's heart) is under abnormal circumstances, and when the individual should consider waiting before making a decision, e.g., in a military, highly physical, or stressful business situation.

In an example implementation, the conformal cardiac sensor system can be configured to provide an indication (e.g., via feedback component 109 of FIG. 1B) of the subject's regime during physical activity, whether the physical activity causes the subject to be in an aerobic regime or anaerobic regime. An optical sensor component or ECG component of the system can be used to provide additional data measures for use in the analysis. For example, an anaerobic regime may be more desirable, since this is when fat is being burned, as opposed to glucose (aerobic regime), during activity. For example, the system can be implemented to determine a subject's condition under constant physical exertion, such as but not limited to, running/walking on a treadmill, or biking on a stationary bike.

In an example implementation, the conformal cardiac sensor system can be configured to maintain a low-power status at a time that no measurement is being performed. In an example, the conformal cardiac sensor system can be configured with a low-power on-board energy supplying component (e.g., a low-power battery). In an example, the conformal cardiac sensor system can be configured with no on-board energy component, and energy may be acquired through inductive coupling or other form of energy harvesting. In these example implementations, the cardiac sensor component(s) may be maintained substantially dormant, in a low-power state, or in an OFF state, until a triggering event occurs. For example, the triggering event can be that the body part or object, to which the system is coupled of disposed on, undergoes motion (or where applicable, muscle activity) above a specified threshold range of values or degree. Examples of such motion could be movement of an arm or other body part, such as but not limited to a bicep or quadriceps movement during physical exertion, a fall (e.g., for a geriatric patient), or a body tremor, e.g., due to an epileptic incident, a Palsy, or Parkinson's. Other examples of such motion could be movement of the object, e.g., a golf club swing, movement of a ball, etc. In another example, the conformal cardiac sensor system may include a near-field component (NFC), and the triggering event may be registered using the NFC component. In other examples, the triggering event may be a sound or other vibration, a change in light level (e.g., a LED) or a magnetic field, temperature (e.g., change in external heat level or blood rushing to an area), or an EEG, a chemical or a physiological measure (e.g., environment pollen or pollution level, or blood glucose level). In an example, the triggering event may be initiated at regular time intervals. The system can be configured such that occurrence of the triggering event causes triggering of the microcontroller; the microcontroller then be configured to cause activation of the ECG, the accelerometer and/or the EMG component, or other sensor component, of the conformal cardiac sensor system to take a measurement.

In an example implementation, the conformal cardiac sensor system may include one or more components (e.g., therapeutic component 108 of FIG. 1B) for administering or delivering an emollient, a pharmaceutical drug or other drug, a biologic material, or other therapeutic material. In an example, the components for administering or delivery may include a nanoparticle, a nanotube, or a microscale component. In an example, the emollient, pharmaceutical drug or other drug, biologic material, or other therapeutic material may be included as a coating on a portion of the conformal sensor system that is proximate to the body part. On occurrence of a triggering event (such as any triggering event described hereinabove), the conformal cardiac sensor system can be configured to trigger the delivery or administering of the emollient, drug, biologic material, or other therapeutic material. The occurrence of the triggering event can be a measurement of the ECG, the accelerometer, and/or the EMG or other sensor component. On the triggering event, the microcontroller can be configured to cause activation of the one or more components (e.g., therapeutic component 108 of FIG. 1B) for the administering or delivery. The delivery or administering may be transdermally. In some examples, the amount of material delivered or administered may be calibrated, correlated or otherwise modified based on the magnitude of the triggering event, e.g., where triggering event is based on magnitude of muscle movement, a fall, or other quantifiable triggering event. In some examples, the system can be configured to heat a portion of the body part, e.g., by passing a current through a resistive element, a metal, or other element, that is proximate to the portion of the body part. Such heating may assist in more expedient deliver or administering of the emollient, drug, biologic material, or other therapeutic material to the body part, e.g., transdermally.

In an example implementation, the conformal cardiac sensor system may include one or more components (e.g., therapeutic component 108 of FIG. 1B) for administering or delivering insulin, insulin-based or synthetic insulin-related material. In an example, the insulin, insulin-based or synthetic insulin-related material may be included as a coating on a portion of the conformal sensor system that is proximate to the body part. On occurrence of a triggering event (such as any triggering event described hereinabove), the conformal cardiac sensor system can be configured to trigger the delivery or administering of the insulin, insulin-based or synthetic insulin-related material. The occurrence of the triggering event can be a measurement of the ECG, accelerometer, and/or the EMG or other sensor component. On the triggering event, the microcontroller can be configured to cause activation of the one or more components for the administering or delivery of the insulin, insulin-based or synthetic insulin-related material. The delivery or administering may be transdermally. The amount of material delivered or administered may be calibrated, correlated or otherwise modified based on the magnitude of the triggering event, (e.g., blood glucose level).

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be examples and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that inventive embodiments may be practiced otherwise than as specifically described. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments of the invention may be implemented in any of numerous ways. For example, some embodiments may be implemented using hardware, software or a combination thereof. When any aspect of an embodiment is implemented at least in part in software, the software code may be executed on any suitable processor or collection of processors, whether provided in a single device or computer or distributed among multiple devices/computers.

Also, the technology described herein may be embodied as a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

The indefinite articles "a" and "an," as used herein in the specification, unless clearly indicated to the contrary, should be understood to mean "at least one."

The phrase "and/or," as used herein in the specification, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

While particular embodiments and applications of the present disclosure have been illustrated and described, it is to be understood that the present disclosure is not limited to the precise construction and compositions disclosed herein and that various modifications, changes, and variations can be apparent from the foregoing descriptions without departing from the spirit and scope of the invention as defined in the appended claims.

What is claimed:

1. A conformal cardiac sensor device for analyzing cardiac activity of a user, the conformal cardiac sensor device comprising:
    at least one flexible substrate configured to couple to the user;
    at least one heart sensor component embedded on or within the at least one flexible substrate, the at least one heart sensor component being configured to directly contact a portion of skin of the user, measure electrical activity indicative of cardiac activity of the user, and output a signal indicative thereof;
    at least one biometric sensor component embedded on or within the at least one flexible substrate, the at least one biometric sensor component being configured to measure physiological activity indicative of cardiac activity of the user and output a signal indicative thereof;
    at least one microprocessor embedded on or within the at least one flexible substrate, the at least one microprocessor being communicatively coupled to the at least one heart sensor component and the at least one biometric sensor component and operable to execute microprocessor executable instructions for controlling the measurement of electrical and physiological activity indicative of cardiac activity of the user; and
    at least one wireless communication component embedded on or within the at least one flexible substrate and operable to transmit data indicative of the measurements obtained by the at least one heart sensor component and the at least one biometric sensor component.

2. The conformal cardiac sensor device of claim 1, further comprising at least one therapeutic component embedded on or within the at least one flexible substrate, the at least one therapeutic component being configured to provide medicinal treatment to the user based, at least in part, on the measurements obtained by the at least one heart sensor component and the at least one biometric sensor component.

3. The conformal cardiac sensor device of claim 2, wherein the at least one therapeutic component is configured to administer to the user an emollient, a pharmaceutical drug or other drug, a biologic material, or other therapeutic material, or any combination thereof.

4. The conformal cardiac sensor device of claim 3, wherein the emollient, pharmaceutical drug or other drug, biologic material, or other therapeutic material are delivered to the user in response to a detected occurrence of a predetermined triggering event.

5. The conformal cardiac sensor device of claim 4, wherein the emollient, pharmaceutical drug or other drug, biologic material, or other therapeutic material are delivered to the user transdermally.

6. The conformal cardiac sensor device of claim 4, wherein an amount of the emollient, pharmaceutical drug or other drug, biologic material, or other therapeutic material delivered to the user is calibrated, correlated or otherwise modified based on a magnitude of the detected occurrence of the predetermined triggering event.

7. The conformal cardiac sensor device of claim 1, further comprising at least one feedback component embedded on or within the at least one flexible substrate, the at least one feedback component being configured to analyze the measurements obtained by the at least one heart sensor component and the at least one biometric sensor component and provide diagnostic information or other physiological information to the user based on the analyzed measurements.

8. The conformal cardiac sensor device of claim 7, wherein the at least one feedback component is configured to display to the user an indication of the user's overall fitness, VO2 max, cardiovascular demand, energy expenditure, activity level, quality of sleep, stress level, heart plasticity or abnormality, or disordered breathing, or any combination thereof.

9. The conformal cardiac sensor device of claim 1, wherein the least one heart sensor component includes an electromyography (EMG) component, an electrocardiogram (EKG) component, or an electroencephalogram (EEG) component, or any combination thereof.

10. The conformal cardiac sensor device of claim 1, wherein the least one biometric sensor component includes an accelerometer module, a gyroscope module, a muscle activation measurement module, or any combination thereof.

11. The conformal cardiac sensor device of claim 1, further comprising at least one power supply embedded on or within the at least one flexible substrate and operable to power the heart sensor component, the biometric sensor component, the microprocessor and the wireless communication component.

12. The conformal cardiac sensor device of claim 1, further comprising at least one memory device embedded on or within the at least one flexible substrate and storing the microprocessor executable instructions.

13. The conformal cardiac sensor device of claim 1, wherein the heart sensor component comprises a plurality of conformal electrodes embedded on or within the at least one flexible substrate, wherein the plurality of conformal electrodes is configured to directly contact the portion of skin of the user.

14. The conformal cardiac sensor device of claim 1, wherein the at least one flexible substrate is a stretchable polymeric patch surrounding the at least one heart sensor component, the at least one biometric sensor component, the at least one microprocessor, and the at least one wireless communication component.

15. A conformal cardiac sensor assembly for analyzing cardiac activity of an individual, the conformal cardiac sensor assembly comprising:
- a flexible substrate operable to attach to a portion of the individual;
- a power supply attached or coupled to the flexible substrate;
- a microprocessor attached or coupled to the flexible substrate and operable to execute microprocessor executable instructions;
- a sensor component attached or coupled to the flexible substrate and configured to measure an electrical variable or a physiological variable, or both, indicative of cardiac activity of the individual; and
- a therapeutic component attached or coupled to the flexible substrate and configured to provide medicinal treatment to the individual based, at least in part, on the measurements obtained by the sensor component.

16. A conformal cardiac sensor system for monitoring cardiac activity of a user, the conformal cardiac sensor system comprising:
- one or more memory devices storing microprocessor executable instructions;
- one or more microprocessors electrically coupled to the one or more memory devices and operable to execute the microprocessor executable instructions;
- one or more first sensor devices electrically coupled to the one or more microprocessors and operable to obtain one or more first measurements indicative of cardiac activity of the user;
- one or more second sensor devices electrically coupled to the one or more microprocessors and operable to obtain one or more second measurements indicative of cardiac activity of the user;
- one or more wireless communication components electrically coupled to the one or more microprocessors and operable to transmit data indicative of the measurements obtained by the one or more first and one or more second sensor devices; and
- one or more power supplies electrically coupled to and operable to power the one or more memory devices, the one or more microprocessors, the one or more first and second sensor devices, and the one or more wireless communication components.

17. The conformal cardiac sensor system of claim 16, further comprising one or more therapeutic components configured to provide medicinal treatment to the user based, at least in part, on the measurements obtained by the one or more first and second sensor devices.

18. The conformal cardiac sensor system of claim 17, wherein at least one of the one or more therapeutic components is configured to administer to the user an emollient, a pharmaceutical drug or other drug, a biologic material, or other therapeutic material, or any combination thereof.

19. The conformal cardiac sensor system of claim 16, further comprising one or more feedback components configured to analyze the measurements obtained by the one or more first and second sensor devices and provide diagnostic information or other physiological information to the user based on the analyzed measurements.

20. The conformal cardiac sensor system of claim 16, wherein the feedback component is configured to display to the user an indication of the user's overall fitness, VO2 max, cardiovascular demand, energy expenditure, activity level, quality of sleep, stress level, heart plasticity or abnormality, or disordered breathing, or any combination thereof.

* * * * *